US011077183B2

(12) United States Patent
Tang et al.

(10) Patent No.: US 11,077,183 B2
(45) **Date of Patent: *Aug. 3, 2021**

(54) CD40 LIGAND FUSION PROTEIN VACCINE

(71) Applicant: MicroVAX, LLC, Warrenton, VA (US)

(72) Inventors: Yucheng Tang, San Diego, CA (US); Albert B. Deisseroth, Potomac, MD (US)

(73) Assignee: MicroVAX, LLC, Warrenton, VA (US)

( * ) Notice: Subject to any disclaimer, the term of this patent is extended or adjusted under 35 U.S.C. 154(b) by 818 days.

This patent is subject to a terminal disclaimer.

(21) Appl. No.: 15/393,543

(22) Filed: Dec. 29, 2016

(65) Prior Publication Data

US 2017/0182147 A1 Jun. 29, 2017

Related U.S. Application Data

(63) Continuation of application No. 11/593,458, filed on Nov. 6, 2006, now Pat. No. 9,533,036.

(60) Provisional application No. 60/734,136, filed on Nov. 7, 2005, provisional application No. 60/755,885, filed on Jan. 4, 2006, provisional application No. 60/789,270, filed on Apr. 4, 2006, provisional application No. 60/793,206, filed on Apr. 19, 2006, provisional application No. 60/853,184, filed on Oct. 20, 2006.

(51) Int. Cl.

| | |
|---|---|
| ***A61K 39/145*** | (2006.01) |
| ***A61K 39/39*** | (2006.01) |
| ***A61K 39/12*** | (2006.01) |
| ***C07K 14/005*** | (2006.01) |
| ***C07K 14/705*** | (2006.01) |
| ***A61K 39/00*** | (2006.01) |
| ***A61K 39/385*** | (2006.01) |

(52) U.S. Cl.

CPC ............ *A61K 39/145* (2013.01); *A61K 39/12* (2013.01); *A61K 39/39* (2013.01); *C07K 14/005* (2013.01); *C07K 14/70575* (2013.01); *A61K 39/385* (2013.01); *A61K 2039/5256* (2013.01); *A61K 2039/53* (2013.01); *A61K 2039/545* (2013.01); *A61K 2039/55* (2013.01); *A61K 2039/575* (2013.01); *A61K 2039/585* (2013.01); *A61K 2039/6031* (2013.01); *C07K 2319/02* (2013.01); *C07K 2319/06* (2013.01); *C07K 2319/33* (2013.01); *C12N 2710/10034* (2013.01); *C12N 2710/10043* (2013.01); *C12N 2710/10343* (2013.01); *C12N 2710/20034* (2013.01); *C12N 2760/16122* (2013.01); *C12N 2760/16134* (2013.01)

(58) Field of Classification Search

None

See application file for complete search history.

(56) References Cited

PUBLICATIONS

World health Organization: Biologicals—Infuenza, Nov. 15, 2018. Accessed online at https://www.who.int/biologicals/vaccines/influenza/en/, 4 pages.

N. M. Bouvier et al.: "The Biology of Influenza Viruses," Vaccine, Sep. 12, 2008; 26 (Suppl4), 10 pages.

*Primary Examiner* — Patricia Duffy

(74) *Attorney, Agent, or Firm* — Jacob Frank; Glenn Snyder

(57) ABSTRACT

Provided are methods of generating an immune response to any of various antigens including foreign antigens such as infectious agent antigens. In general, the method comprises administering an expression vector encoding a transcription unit encoding a secretable fusion protein, the fusion protein containing the foreign antigen and CD40 ligand and also administering the encoded fusion protein. In another approach, an immune response to the foreign antigen is elicited using the encoded fusion protein without administering the vector. The invention methods may be used to immunize an individual against an infectious agent such as influenza virus. Methods of obtaining an immune response in older individuals also is described.

17 Claims, 33 Drawing Sheets

Specification includes a Sequence Listing.

FIG. 1

(Amino Acid sequence of (H5N1)M2; GenBank Accession NO AF036358)

1 MSLLTEVETLTRNGWGCRCSDSSDPLVVAASIIGILHLILWILDRLFFKC

51 IYRRFKYGLKRGPSTEGVPESMREEYRQEQQNAVDVDDGHFVNIELE (SEQ ID NO:1)

FIG. 2

(Amino Acid SEQUENCE OF H5HA; GenBank ACCESSION NO AF036356)

1 DQICIGYHANNSTEQVDTIMEKNVTVTHAQDILERTHNGKLCDLNGVKPL

51 ILRDCSVAGWLLGNPMCDEFINVPEWSYIVEKASPANDLCYPGNFNDYEE

101 LKHLLSRINHFEKIQIIPKSSWSNHDASSGVSSACPYLGRSSFFRNVVWL

151 IKKNSAYPTIKRSYNNTNQEDLLVLWGIHHPNDAAEQTKLYQNPTTYISV

201 GTSTLNQRLVPEIATRPKVNGQSGRMEFFWTILKPNDAINFESNGNFIAP

251 EYAYKIVKKGDSTIMKSELEYGNCNTKCQTPMGAINSSMPFHNIHPLTIG

301 ECPKYVKSNRLVLATGLRNTPQRERRRKKRGLFGAIAGFIEGGWQGMVDG

351 WYGYHHSNEQGSGYAADKESTQKAIDGVTNKVNSIINKMNTQFEAVGREF

401 NNLERRIENLNKKMEDGFLDVWTYNAELLVLMENERTLDFHDSNVKNLYD

451 KVRLQLRDNAKELGNGCFEFYHKCDNECMESVKNGTYDYPQYSEEARLNR

501 EEISGVKLESMGTYQILSIYSTVASSLALAIMVAGLSLWMCSNGSLQCRICI (SEQ ID NO:2)

FIG. 3

(Amino Acid SEQUENCE OF M2; GenBank ACCESSION NO AAA43276)

1 MSLLTEVETPIRNEWGCRCNDSSDPLVVAASIIGILHLILWILDRLFFKC

51 IYRFFEHGLKRGPSTEGVPESMREEYRKEQQSAVDADDSHFVSIELE(SEQ ID NO:3)

FIG. 4

(Amino Acid SEQUENCE OF H3HA; GenBank ACCESSION NO V01085)

1 MKTIIALSYIFCLALGQDLPGNDNSTATLCLGHHAVPNGTLVKTITDDQI

51 EVTNATELVQSSSTGKICNNPHRILDGIDCTLIDALLGDPHCDVFQNETW

101 DLFVERSKAFSNCYPYDVPDYASLRSLVASSGTLEFITEGFTWTGVTQNG

151 GSNACKRGPGSGFFSRLNWLTKSGSTYPVLNVTMPNNDNFDKLYIWGIHH

201 PSTNQEQTSLYVQASGRVTVSTRRSQQTIIPNIGSRPWVRGLSSRISIYW

251 TIVKPGDVLVINSNGNLIAPRGYFKMRTGKSSIMRSDAPIDTCISECITP

301 NGSIPNDKPFQNVNKITYGACPKYVKQNTLKLATGMRNVPEKQTRGLFGA

351 IAGFIENGWEGMIDGWYGFRHQNSEGTGQAADLKSTQAAIDQINGKLNRV

401 IEKTNEKFHQIEKEFSEVEGRIQDLEKYVEDTKIDLWSYNAELLVALENQ

451 HTIDLTDSEMNKLFEKTRRQLRENAEEMGNGCFKIYHKCDNACIESIRNG

501 TYDHDVYRDEALNNRFQIKGVELKSGYKDWILWISFAISCFLLCVVLLGF

551 IMWACQRGNIRCNICI (SEQ ID NO:4)

FIG. 5

(Nucleic Acid SEQUENCE ENCODING FRAGMENT OF HA and FRAGMENT OF M2)

A)

5′- AAAAGTTCTT GGTCCAATCA TGATGCCTCA TCAGGGGTGA GCTCAGCATG
TCCATACCTT GGGAGGTCCT CCTTTTTCAG AAATGTGGTA TGGCTTATCA
AAAAGAACAG TGCATACCCA ACAGCTACTA GACCCAAAGT AAACGGGCAA
AGTGGAAGAA TGGAGTTCTT CTGGACAATT TTAAAG-3′ (SEQ ID NO:5)

B)

5′- ATGAGCCTTC TAACCGAGGT TGACACGCTT ACCAGAAACG GATGGGGGTG
CGATGCAGCG ATTCAAGTGAT-3′ (SEQ ID NO:6)

FIG. 19A

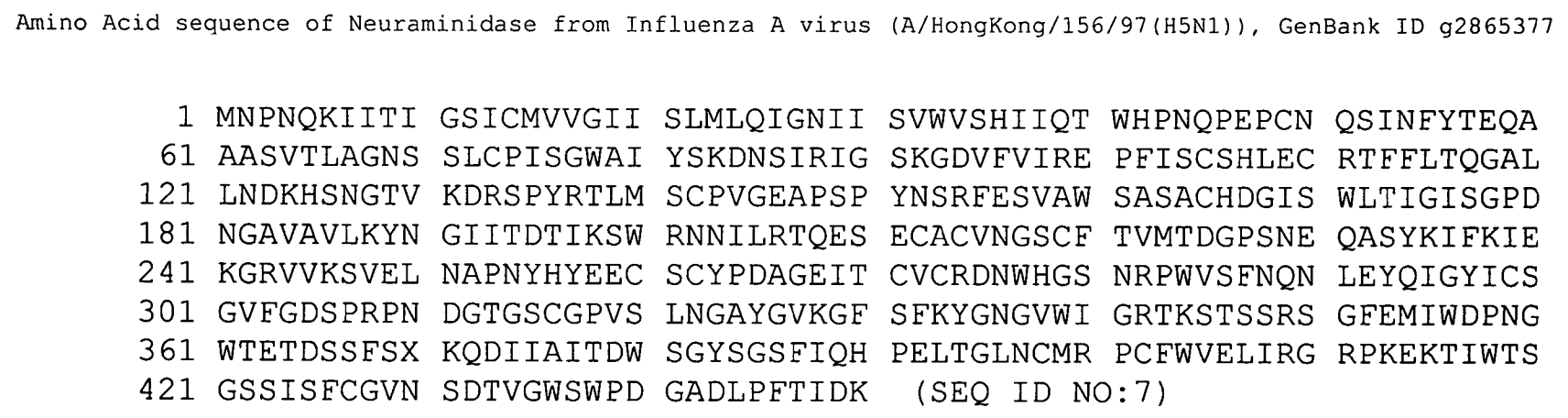

Amino Acid sequence of Neuraminidase from Influenza A virus (A/HongKong/156/97(H5N1)), GenBank ID g2865377

```
  1 MNPNQKIITI GSICMVVGII SLMLQIGNII SVWVSHIIQT WHPNQPEPCN QSINFYTEQA
 61 AASVTLAGNS SLCPISGWAI YSKDNSIRIG SKGDVFVIRE PFISCSHLEC RTFFLTQGAL
121 LNDKHSNGTV KDRSPYRTLM SCPVGEAPSP YNSRFESVAW SASACHDGIS WLTIGISGPD
181 NGAVAVLKYN GIITDTIKSW RNNILRTQES ECACVNGSCF TVMTDGPSNE QASYKIFKIE
241 KGRVVKSVEL NAPNYHYEEC SCYPDAGEIT CVCRDNWHGS NRPWVSFNQN LEYQIGYICS
301 GVFGDSPRPN DGTGSCGPVS LNGAYGVKGF SFKYGNGVWI GRTKSTSSRS GFEMIWDPNG
361 WTETDSSFSX KQDIIAITDW SGYSGSFIQH PELTGLNCMR PCFWVELIRG RPKEKTIWTS
421 GSSISFCGVN SDTVGWSWPD GADLPFTIDK  (SEQ ID NO:7)
```

FIG. 19B

```
   1 agcaaaagca ggagtttaaa atgaatccaa atcagaagat aataaccatt ggatcaatct
  61 gtatggtagt tgggataatc agcttgatgt tacaaattgg aaacataata tcagtatggg
 121 tcagccacat aattcaaact tggcacccaa accagcctga accatgcaat caaagcatca
 181 atttttacac tgagcaggct gcagcttcag tgacattagc gggcaattcc tctctctgcc
 241 ctattagtgg atgggctata tacagcaagg acaatagtat aagaattggt tccaaagggg
 301 atgtgtttgt tataagagaa ccattcatct catgttccca tttggaatgc agaacctttt
 361 tcttgaccca aggagcccta ttgaatgaca agcattctaa tgggaccgtc aaagacagga
 421 gcccctatag aactttaatg agctgtcctg ttggtgaggc tccttcccca tacaactcaa
 481 ggtttgagtc tgttgcttgg tcggcaagtg cttgccatga tggcattagt tggctaacaa
 541 ttggaatttc cggtccggat aatggggctg tggctgtgtt gaaatacaat ggcataataa
 601 cagacaccat caagagttgg aggaacaaca tactgaggac gcaagagtct gaatgtgcat
 661 gtgtgaatgg ttcttgtttt actgtaatga cagatggacc gagtaatgaa caggcctcat
 721 acaagatttt caagatagaa aaggggaggg tagtcaaatc agttgagttg aacgccccta
 781 attatcatta cgaggaatgc tcctgttatc ctgatgctgg cgaaatcaca tgtgtgtgca
 841 gggataattg gcatggctcg aaccgaccat gggtgtcttt caatcagaat ctggagtatc
 901 aaataggata tatatgcagt ggggttttcg gagacagtcc acgccccaat gatgggacag
 961 gcagttgtgg tccagtgtct cttaacggag cgtatggagt aaaagggttt tcatttaaat
1021 acggcaatgg tgtttggatc gggagaacca aaagcactag ttccaggagc ggttttgaaa
1081 tgatttggga tccaaatggg tggaccgaaa cagacagtag cttctcgntg aagcaagaca
1141 tcatagcaat aactgattgg tcaggataca gcgggagttt tattcaacat ccagaactga
1201 caggattaaa ttgcatgaga ccttgcttct gggttgaact aatcagaggg aggcccaaag
1261 agaaaacaat ctggactagt gggagcagta tatctttctg tggtgtaaat agtgacactg
1321 tgggttggtc ttggccagac ggtgctgatt tgccattcac cattgacaag tagttsgttc
1381 aaaaaact  (SEQ ID NO:8)
```

FIG. 20

```
MERTVLLLATVSLVKSDQICIGYHANNSTEQVDTIMEKNVTVTHAQDILE 50
RTHNGKLCDLNGVKPLILRDCSVAGWLLGNPMCDEFINVPEWSYIVEKAS 100
PANDLCYPGNFNDYEELKHLLSRINHFEKIQIIPKSSWSNHDASSGVSSA 150
CPYLGRSSFFRNVVWLIKKNSAYPTIKRSYNNTNQEDLLVLWGVHHPNDA 200
AEQTKLYQNPTTYISVGTSTLNQRLVPEIATRPKVNGQSGRMEFFWTILK 250
PNDAINFESNGNFIAPEYAYKIVKKGDSTIMKSELEYGNCNTKCQTPMGA 300
INSSMPFHNIHPLTIGECPKYVKSNRLVLATGLRNTPQRERRRKKRGLFG 350
AIAGFIEGGWQGMVDGWYGYHHSNEQGSCYSADKESTQKAIDGVTNKVNS 400
IINKMNTQFEAVGREFNNLERRIENLNKKMEDGFLDVWTYNAELLVLMEN 450
ERTLDFHDSNVKNLYDKVRLQLRDNAKELGNGCFEFYHKCDNECMESVKN 500
GTYDYPQYSEEARLNREEISGVKLESMGTYQILSIYSTVASSLALAIMVA 550
GLSLWMCSNGSLQCRICI*  (SEQ ID NO:9)
```

FIG. 21

MKTIIALSYIFCLVFAQDLPGNDNNSTATLCLGHHAVPNGTLVKTITNDQIEVTNATELVQSS

STGKICNNPHRILDGINCTLIDALLGDPHCDGFQNEKWDLFVERS*KAFSNCYPYDVPDY*ASLR

SLVASSGTLEFINEGFNWTGVTQNGGSSACKRGPDSGFFSRLNWLYKSGSTYPVQNVTMPNND

NSDKLYIWGVHHPSTDKEQTNLYVQASGKVTVSTKRSQQTIIPNVGSRPWVRGLSSRISIYWT

IVKPGDILVINSNGNLIAPRGYFKMRTGKSSIMRSDAPIGTCSSECITPNGSIPNDKPFQNVN

KITYGACPKYVKQNTLKLATGMRNVPEKQTRGIFGAIAGFIENGWEGMIDGWYGFRHQNSEGT

GQAADLKSTQAAIDQINGKLNRVIEKTNEKFHQIEKEFSEVEGRIQDLEKYVEDTKIDLWSYN

AELLVALENQHTIDLTDSEMNKLFEKTRRQLRENAEDMGNGCFKIYHKCDNACIGSIRNGTYD

HDVYRDEALNNRFQIKGVELKSGYKDWILWISFAISCFLLCVVLLGFIMWACQKGNIRCNIC (SEQ ID NO:10)

FIG. 22

```
  1 MNPNQKIITI GSVSLTIATI CFLMQIAILV TTVTLHFKQY ECSSPPNNQV MLCEPTIIER
 61 NITEIVYLTN TTIEKEICPK LAEYRNWSKP QCKITGFAPF SKDNSIRLSA GGDIWVTREP
121 YVSCDPDKCY QFALGQGTTL NNRHSNDTVH DRTPYRTLLM NELGVPFHLG TKQVCIAWSS
181 SSCHDGKAWL HVCVTGHDEN ATASFIYDGR LVDSIGSWSK KILRTQESEC VCINGTCTVV
241 MTDGSASGRA DTKILFIEEG KIVHISPLSG SAQHVEECSC YPRYPGVRCV CRDNWKGSNR
301 PIVDINVKDY SIVSSYVCSG LVGDTPRKND SSSSSHCLNP NNEEGGHGVK GWAFDDGNDV
361 WMGRTISEKF RSGYETFKVI EGWSKPNSKL QINRQVIVDR GNRSGYSGIF SVEGKSCINR
421 CFYVELIRGR KQETEVWWTS NSIVVFCGTS GTYGTGSWPD GADINLMPI
```
(SEQ ID NO:11)

CD40 LIGAND FUSION PROTEIN VACCINE

CROSS-REFERENCE TO RELATED APPLICATIONS

This application is a continuation of U.S. patent application Ser. No. 11/593,458, filed on Nov. 6, 2006, which claims priority and the benefit of U.S. Provisional Application No. 60/734,136 filed Nov. 7, 2005, U.S. Provisional Application No. 60/755,885 filed Jan. 4, 2006, U.S. Provisional Application No. 60/789,270 filed Apr. 4, 2006, U.S. Provisional Application No. 60/793,206 filed Apr. 19, 2006, and U.S. Provisional Application No. 60/853,184 filed Oct. 20, 2006, the disclosures of which are all hereby incorporated herein by reference in their entireties.

STATEMENT OF GOVERNMENT SPONSORED RESEARCH

This invention was made with government support under ARMY/MRMC Grant Nos. DAMD17-03-1-0554 and DAMD17-99-1-9457, and Grant No. R43 CA108051. The government has certain rights in this invention.

FIELD OF THE INVENTION

The present invention relates generally to the field of vaccines. In particular, the present invention relates to the use of fusion proteins of CD40 ligand and an antigen in developing immunity to foreign proteins or infectious agents.

BACKGROUND OF THE INVENTION

The following discussion of the background of the invention is merely provided to aid the reader in understanding the invention and is not admitted to describe or constitute prior art to the present invention.

Influenza is an acute contagious illness often characterized by inflammation of the respiratory tract, fever, chills, muscular pain, prostration and maliase and is caused by the Orthomyxoviridae family of influenza viruses. Infection can cause mild to severe illness, and at times can lead to death.

Influenza viruses are classified into three types: Types A, B, and C. Type A influenzas have been responsible for pandemics, spreading over a wide geographic area and affecting a large proportion of the population. Type A influenza viruses are known to infect many animals including birds and mammals (e.g., humans, dogs, horses, cattle, sheep, pigs and seals). In contrast, type B influenzas tend usually to infect only humans. Type A and B influenzas are responsible for the increased flu-related illnesses, hospitalizations and deaths that occur each year. Type C influenzas tend to be the least worrisome. Infection in humans may cause mild respiratory distress or no symptoms at all.

Type A influenza viruses are further classified by strain. The strain name is determined by identifying differences between two antigenic proteins, hemagglutinin ("HA") and neuraminidase ("NA"), both present on the viral surface. Rapid alterations in the sequence of these two proteins (termed "antigenic shift") are mainly responsible for the yearly changes in immunogenicity and the requirement for new vaccines each year. Examples of antigenic shift and the concomitant strain change are clear: between 1918 and 1957, the H1N1 strain was dominant; between 1957 and 1968, the H2N2 strain was dominant; then, since 1968, the H3N2 virus dominated. Most recently, in 1997, the H5N1 strain of avian influenza was shown to infect humans. In addition to antigenic shift, the antigenic properties of influenza viruses can also change more slowly via "antigenic drift," the slow, gradual process of viral evolution. Antigenic variation (drift) of HA sequences is noted, for example, in human trials with the escape of viral strains from vaccine induced immunity.

One cause of the rapid sequence changes associated with "antigenic shift" is the formation of reassortant viral strains. The pig can be infected by both human and avian influenza strains, and an exchange of RNA stands between human and avian strains can occur within the pig. These "reassortant" viruses may infect the human species causing a yearly epidemic of influenza. Thus, the rapid changes in the HA and NA proteins resulting from antigenic shift render old influenza viral vaccines ineffective.

Hemagglutinin ("HA"), one of the proteins affected by antigenic shift, is an antigenic glycoprotein found on the surface of influenza viruses. HA functions to secure the virus to the target cells by binding to N-acetyl neuraminic acid or sialic acid on host cell receptors. HA is composed of two subunits, HA1 and HA2. HA2 is the viral membrane anchoring domain, while HA1 is responsible for binding host cell receptors. As noted above, HA is highly mutable and variations, mainly in HA1, are a key source of viral antigen variability conferring the ability to evade the immune system. There are currently between 16 and 20 different HA varieties known, H1, H2 and H3 have been the dominant human influenza subtypes, while the H5 and H7 subtypes have been prevalent for avian species.

Neuraminidase ("NA") is also presented on the viral surface and functions to catalyze the removal of terminal sialic acid residues of glycosyl groups, thus destroying potential receptors for hemagglutinin. It is probable that neuraminidase is required to prevent viral aggregation and to promote more efficient spreading of the virus from cell to cell. The neuraminidase protein sequence is also highly variable; there are currently nine different neuraminidase varieties known. Accordingly, changes in this protein sequences also play a role in antigenic shift.

Another viral protein present on the viral influenza surface is the Matrix protein 2 ("M2"), an ion channel protein that selectively allows protons to enter the virus. After the virus enters a cell, an influx of protons is key in the removal of the viral protein coat. The M2 protein is homotetramer comprised of three domains: a 23 amino-acid region present on the outside of the virus (extra cellular domain), a 54 amino acid region that is inside the virus (cytoplasmic domain) and a 19 amino-acid transmembrane domain. M2 is expressed at low levels on the viral surface but is present at high levels on influenza infected cells. The M2 protein sequence is stable compared to hemagglutinin or neuraminidase. In fact, the 23-amino acid extra cellular domain of M2 is well conserved in many known influenza strains (some exceptions include A/PR/8/34, A/Brevig and Mission/1/8). Although this protein is not immunogenic normally, it has been shown that chimeric molecules made from the extra cellular domain of the M2 and "adjuvant proteins" such as the hepatitis B core protein induce a potent immune response (Virology 2005 337:149-161; Infection and Immunity 2002 70:6860-70), The intranasal administration of the M2HB core particle, along with adjuvants (such as a detoxified enterotoxin adjuvant), protected 2-4 month old BalbC mice from challenge with human influenza virus (Virology 2005 337:149-161). M2, which is important in determining host range (J. Virology 1999 73:3366-3374), is present at such low levels in the virus that antibodies are not generated. HA has been the target for vaccines since the antibodies to H5 have been shown to prevent influenza viral infection.

A commercial human vaccine against the H5N1 strain of influenza has not yet been developed, although the H5 strain of avian influenza virus was seen to infect human directly in 1997; 6/18 infected people died. Since that time, outbreaks have occurred in 2003 in Hong Kong (2 deaths in 3 cases), and in Vietnam/Thailand in 2004 (28 deaths in 39 infected cases (Kash J C et al., Journal of Virology 78: 9499-9511 (2004); Apisarnthanarak A, et al., Emerg. Infect. Dis. 10 (2004)). In 2005, 79/150 H5N1 infected human beings died. Over 99% of the sequences of the infecting H5N1 virsus are avian, suggesting direct transmission from the poultry to human beings (Science 2001 293:1840-1842; J. Virology 2000 74:1443-1450). When the avian influenza viruses acquire the capability of directly jumping from birds to humans, there is a potential for a pandemic. For this to occur, the virus must be able to be transmitted in aerosols from person to person. A transition from avian:human to human: human transmission resulting in a pandemic was documented for the first time in 1918 in an H1N1 strain. The result was more than 600,000 deaths in the USA and 40 million worldwide (J. Virology 2004 78: 9499-9511). Statistics show that most of the deaths were restricted to younger individuals living in crowded conditions (soldiers involved in World War I).

The H5N1 strain has been reported to infect humans (J. Virology 2000 74:1443-1450). It is estimated that if this virus acquires the capability of spreading from human to human, there impact in the USA will be over 200,000 deaths, over 700,000 hospitalizations, over 40 million outpatient visits, and an economic impact of over 100 billion dollars (Infect. Dis. 1999 5:659-671). The recent apparent trend for increased reporting deaths of individuals believed infected with the avian flu virus has created concern among governments around the world (J. Virology 2004 78:9499-9511; J. Emere, Infect. Dis. 2004 10; Virology 2003 208:270-278; Eur. J. Biochem. 1999 260:166-175).

The testing of vaccine efficacy for the H5N1 avian flu has been carried out in mice and ferrets, but the virulence of the various human strains in ferrets is closer to that seen in humans (J. Virology 2005 79:2191-2198). The pathogenicity of the various strains has been correlated with the HA protein structure (Id). After the 1997 cases in Hong Kong, two strategies for vaccines against the H5N1 strains were tested. First, it was discovered that a subunit H5 vaccine did not appear to be immunogenic in humans (J. Infect. Dis. 2005 191:1213-1215; Vaccine 2003 21:1687-1693). However, the addition of MF59 adjuvant increased the antibody response (PNAS USA 2005 102:12915-12920). In a second approach, a multivalent vaccine (H3N1 and H5N1) was used but this proved equally ineffective (Virology 1999 73:2094-2098).

Recently, an HA DNA vaccine was shown to protect mice from the H5N1 strain (clintrials.gov/ct/gui/sho/NCT00110279;jsessionid=743259FCCOA680603EA), and there is currently a clinical trial to evaluate the immune response to H9N2 avian flu in humans (Vaccine 2002 20:1099-1105). The H9N2 study involves a cold-adapted resorted attenuated viral vaccine which is administered by intramuscular injection. It is hoped that this study will provide insight into an H5N1 immune response. Additionally, an intramuscularly administered vaccine from baculovirus expressing H5 HA was tested in 147 adults. A 23% antibody response was observed after a single injection and 52% response after two injections (*Lancet* 2004 357:1937-1943).

The elderly are especially at risk with respect to influenza infection, and vaccination against influenza is recommended for older individuals to prevent the potentially deadly complications of infection such as pneumonia or bronchitis. One cause of increased risk in the elderly is the decrease in function of the immune system with age. For example, there is a decrease in the number of naïve, antigen unexposed CD4 and CD8 T cells. Additionally, the ratio of the naïve to memory CD8/CD4 cells decreases as the chronological age increases. Further, CD4 cells become impaired, acquiring both quantitiative and functional defects, such as diminished levels of the CD40 ligand (CD40L) on the surface of CD4 cells as well as a temporal retardation of the rate at which CD40 ligand (CD40L) is expressed on the surface of the CD4 cells following activation. Accordingly, the amount of antibody that an elderly system is able to generate will be lower following infection or conventional vaccination.

Testing has shown that current methods of vaccination are, at best, only moderately effective. Usually, three strains of the human influenza virus are grown up in eggs, purified and then chemically inactivated. Using the induction of neutralizing antibodies in the vaccinated individuals as an endpoint for response, the response to the vaccine is in the 65-70% range (*Lancet* 2004 357:1937-1943). The response is 4-fold less in individuals vaccinated after age 55.

Vaccines have been described that include an expression vector encoding a fusion protein that includes an antigen fused to CD40 ligand. See, e.g., U.S. Patent Application Publication US 2005-0226888 (application Ser. No. 11/009,533) titled "Methods for Generating Immunity to Antigen," filed Dec. 10, 2004.

SUMMARY OF THE INVENTION

According to the present invention there are provided methods of generating an immune response to a fusion protein having CD40 ligand and a foreign antigen. In some embodiments the fusion protein is administered as an expression vector containing DNA encoding the fusion protein. In other embodiments, the fusion protein is directly administered as a protein. Vaccination regimens wherein vector and protein are administered are also provided.

Thus, in a first aspect, there are provided new vaccines for protecting against infection by influenza viruses. An immune response to an influenza antigen is achieved by administering an expression vector encoding a secretable fusion protein which includes an influenza antigen and CD40 ligand.

The influenza antigen may be any influenza antigen to which an immune response may be generated in an individual or animal. In preferred embodiments, the influenza antigen is an mammalian influenza virus antigen (such as a human influenza antigen) or an avian influenza virus antigen. In further embodiments, the influenza antigen may be a combination of mammalian and avian influenza virus antigens, such as a combination of human and avian influenza virus antigens. The influenza antigen is preferably an influenza viral protein, or fragment thereof, which comprises at least one antigenic determinant.

In a preferred embodiment, the influenza antigen of the fusion protein is the matrix protein 2 ("M2") ion channel protein. The M2 protein, which is a tetrameric 23 amino acid long type III transmembrane protein involved in tropism of the virus, is barely detectable on the influenza virus but is expressed at high levels on influenza virus infected cells. In contrast to the HA protein, the M2 has a stable sequence from year to year among different influenza strains.

It is believed that the invariant nature of the M2 antigen when fused to CD40 ligand in the present vaccine design, will provide a "universal" influenza vaccine that, unlike current vaccines, will be effective against different strains of influenza resulting from antigenic drift. This is especially important in that there may not be time to prepare a vaccine against a known unique HA antigen for the avian influenza virus once a pandemic occurs, as there is each year for the human influenza reassorted virus.

In one embodiment, the M2 antigen of the fusion protein lacks all or substantially all of the M2 transmembrane domain. Preferably, the M2 antigen of the fusion protein includes all of the extracellular domain of M2 or at least an antigenic fragment of the extracellular domain of M2.

In other embodiments, the influenza antigen may be a chimeric influenza antigen having at least one antigenic determinant from at least two viral influenza proteins. Such different antigens may be variants of the same antigen (e.g. hemagglutinins from different virus strains, e.g. from H5N1, H2N2, H3N2 or H1N1 strains) or a chimeric influenza antigen having at least one antigenic determinant from at least two different viral influenza proteins (e.g. HA and M2).

In some embodiments, the influenza antigen may be a viral protein or fragment thereof. For example, the viral protein or fragment may be a hemagglutinin ("HA"), a neuraminidase ("NA"), an M2 or any combination of HA, NA or M2. The influenza antigen may comprise: an extracellular domain or domain fragment of the viral antigen (e.g., HA, NA or M2); a cytoplasmic domain or domain fragment; or a combination of extracellular and cytoplasmic sequences from the same protein. In some embodiments, the influenza antigen may be a protein chimera having any immunogenic combination of different influenza proteins (e.g., any combination of hemagglutinin, neuraminidase or M2 proteins or fragments thereof). The influenza protein May be from any strain for which protection is sought. In some embodiments, the influenza antigen may be from an H5N1, H3N2, H1N1 or H2N2 influenza strain. In some embodiments the influenza antigen is a chimeric of HA and M2 proteins or fragments thereof. In other embodiments, the influenza antigen is a chimeric of HA and M2 extracellular domain regions from one or more influenza strains (e.g., from H5N1, H3N2, H1N1 or H2N2).

As used herein an "antigen" is any foreign material that is specifically bound by the combining site of an antibody or by the combining site of a T cell antigen receptor. Antigens may also be immunogens if they are able to trigger an immune response, or haptens if not.

As used herein, "antigenic determinant" refers to a single antigenic site or epitope on a complex antigenic molecule or particle, a minimal portion of a molecule that interacts with an antibody or T cell receptor. Antigenic determinants may be linear or discontinuous.

The fusion protein encoding an influenza antigen may be administered before, concurrently or after administration of the vector. Preferably, the fusion protein is administered after the vector. The sequence of the influenza antigen encoded by the vector and that present in the fusion protein may be identical or may be different. If different, the two preferably have at least one antigenic determinant in common.

In one approach, the sequence encoding the influenza antigen in the fusion protein transcription unit is 5' to sequence encoding the CD40 ligand. In another approach, the sequence encoding the CD40 ligand in the fusion protein transcription unit o sequence encoding the influenza antigen. In a preferred embodiment, the CD40 ligand lacks all or a portion of its transmembrane domain.

In another aspect, the invention provides methods of immunizing an individual against infection by an influenza virus. The method includes administering an expression vector which includes a transcription unit encoding a secretable fusion protein that contains an influenza antigen associated and CD40 ligand. A fusion protein that encodes an influenza antigen associated with the virus and CD40 ligand may also be administered before, concurrently or after administration of the vector. Preferably, the fusion protein is administered after the vector. In this approach, the influenza antigen which is encoded by the vector is chosen to cross-react with the influenza virus for which protection is being sought. The immune response generated by this approach is both cell mediated and humoral (i.e. antibody response). The antibody response can neutralize infectious influenza virus.

In preferred embodiments, the expression vector may be a viral expression vector or a non-viral expression vector; the expression vector may be an adenoviral vector; the vector may be advantageously administered subcutaneously; the vector may be administered on a subsequent occasion(s) to increase the immune response; a signal sequence may be placed upstream of the fusion protein for secretion of the fusion protein; immunity against the antigen may he long lasting and involve generation of cytotoxic $CD8^+$ cells against antigen expressing cells and the production of antibody to the antigen; the transcription unit may include sequence that encodes a linker between the antigen and the CD40 ligand; suitable linkers may vary in length and composition; the expression vector may include a human cytomegalovirus promoter/enhancer for controlling transcription of the transcription unit; and the CD40 ligand may be a human CD40 ligand.

In a further aspect, the invention provides methods of effectively immunizing older individuals by administering an expression vector encoding a secretable fusion protein which includes an antigen and CD40 ligand. Older individuals which may realize an improved immune response using the methods of the invention as compared to other immunization methods are at least 50 years of age, or even at least 55 years of age or even yet at least 60 years of age.

The achievement of improved immune responses with the invention methods as compared to other immunization approaches are applicable to any of various antigens which are fused to CD40 ligand. Such antigen include cancer antigens (tumor associated or tumor specific) or infectious agent antigens. Infectious agent antigens may be bacterial, viral, fungal, protozoan, and the like. Viral antigens may be an influenza antigen as described above. The viral antigen may be from a human papilloma virus. The viral antigen may be the E6 or E7 protein of human papilloma virus.

It is believed that traditional vaccination is poorly effective in older individuals because the expression level of the CD40 ligand (CD40L) on the surface of CD4 cells following activation is greatly reduced in older individuals as compared to young, healthy individuals. On the basis of this functional CD4 defect alone, it is believed that the levels of antibodies that will be made following the conventional vaccination with recombinant antigen and inactivated viral particle vaccines, even with adjuvants, will be lower in older individuals as compared to younger individuals. It is further believed that poor immune responses in older individuals may be due in part to the diminished expression of CD40L by CD4 cells. The administration of an expression vector in accordance with the methods of the invention is believed to result in in vivo activation and antigen loading of dendritic cells (DCs) following release of the fusion protein from vector infected cells. The loading of DC with the CD40 ligand from the fusion protein bypasses the CD4 cell of older individuals which are deficient in CD40L. It has been found that two sc injections of this vaccine vector induces an immune response that last for over a year and which is independent of CD4 cells.

In yet another aspect, the invention provides a vector and the fusion protein encoded thereby along the lines described herein for generating an immune response in an individual against an influenza antigen.

In still another aspect, there is provided a method of increasing the immune responsiveness of an individual having CD4 T cells exhibiting reduced levels of CD40 ligand as compared to young, healthy individuals to vaccination against a cancer antigen or an infectious agent antigen. The method is accomplished by administering to the individual an effective amount of an expression vector having a transcription unit encoding a secretable fusion protein, having a cancer or infectious agent antigen and CD40 ligand.

In a further aspect, there are provided methods of immunizing individuals above the age of 50 against foreign antigens. Such methods are particularly suited for generating immunity to influenza in older individuals, which represent the majority group for which influenza A as well as avian influenza protection is needed.

In another aspect, the invention provides a method of generating an immune response in an individual against a foreign antigen. This method is accomplished by administering to the individual an effective amount of a fusion protein without administering an expression vector encoding the fusion protein, wherein the administering is repeated, and wherein the fusion protein contains the antigen and CD40 ligand. The foreign antigen may be from an infectious agent such as influenza. The foreign antigen of the fusion protein may be glycosylated or non-glycosylated. The immune response generated-.by this approach may be both cell mediated and humoral (i.e. antibody response). The antibody response can neutralize infectious influenza virus.

Abbreviations used herein include "Ad" (adenoviral); "sig" (signal sequence and "ecd" (extra cellular domain); "sc" (subcutaneous).

These and other embodiments are described in detail below.

BRIEF DESCRIPTION OF THE DRAWINGS

FIG. 1 shows an amino sequence of an M2 protein from an H5N1 influenza virus (GenBank Accession No. AF036358, SEQ ID NO:1).

FIG. 2 shows an amino sequence of an HA protein (without the N-terminal 16 amino acid signal peptide) from an H5N1 influenza virus (GenBank Accession No. AF036356, SEQ ID NO:2).

FIG. 3 shows an amino sequence of an M2 protein from an H3N2 influenza virus (GenBank Accession No. AAA43276, SEQ ID NO:3)

FIG. 4 shows an amino sequence of an HA protein from an H3N2 influenza virus (GenBank Accession No. V01085, SEQ ID NO:4).

FIG. 5 shows a nucleotide sequences encoding A) a fragment of an HA protein from an H5N1 influenza virus, and B) a fragment of an M2 protein from an H5N1 influenza virus. (SEQ ID NOs:5 and 6, respectively)

FIG. 19 depicts an exemplary amino acid sequence of neuraminidase H5N1 (FIG. 19A) and the encoding nucleotide sequence (FIG. 19B) of GenBank ID No. g2865377 (SEQ ID NO:7 and SEQ ID NO:8, respectively).

FIG. 20 depicts an exemplary amino acid sequence of an HA from H5N1 (SEQ ID NO:9; GenBank ID g2865380). Underlined are residues reported to be involved in receptor binding.

FIG. 21 depicts an exemplary precursor HA molecule from strain H3N2 (GenBank Accession No. V01086; SEQ ID NO:10). Underlined and italicized sequence is involved in receptor binding or represents an epitope against which neutralizing antibodies have been generated.

FIG. 22 depicts an exemplary amino acid sequence of neuraminidase from influenza A virus strain A/Memphis/31/98 (H3N2), GenBank ID g30385699 (SEQ ID NO: 11). Residues reported to be mutated in known escape mutants are shown underlined in bold. The extracellular domain is shaded.

DETAILED DESCRIPTION OF THE INVENTION

Figure 6:
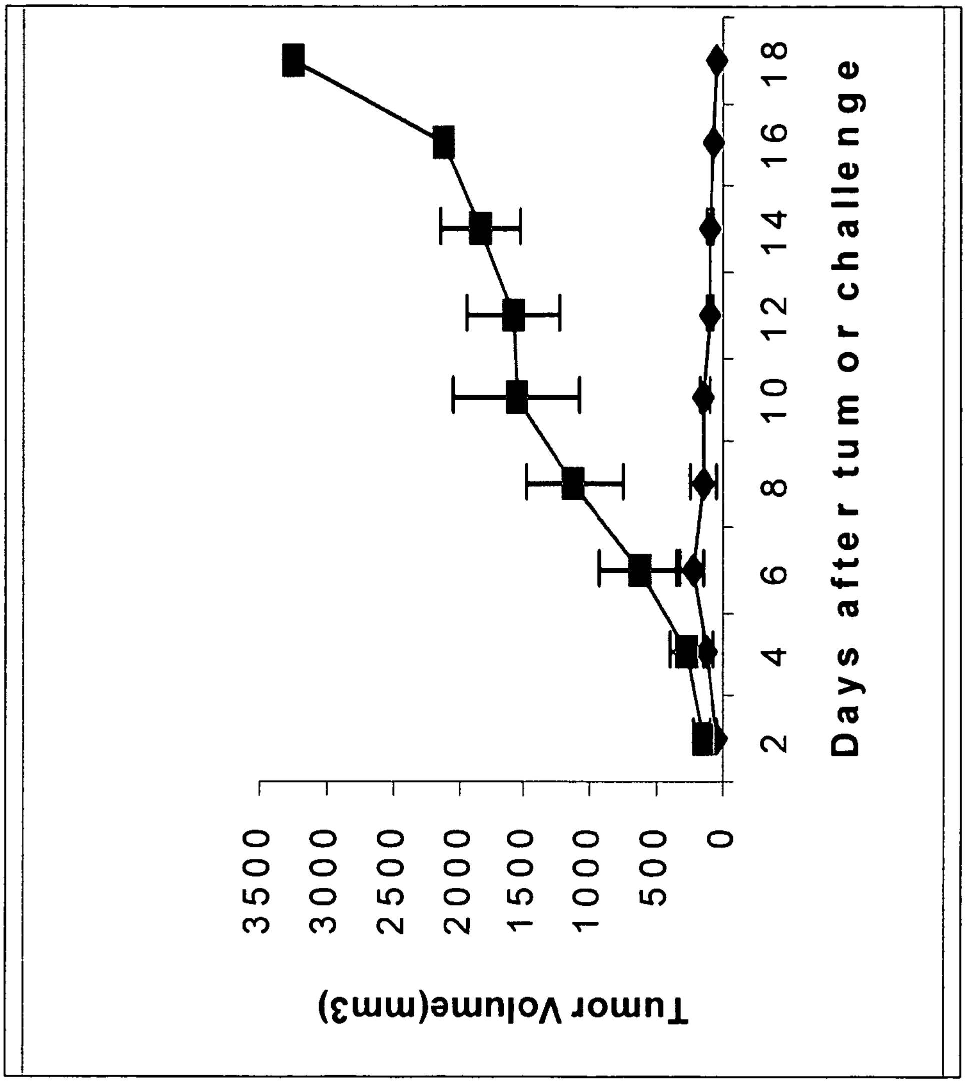
FIG. 6 depicts the growth of E7-positive TC-1 and E7-negative EL-4 cells in Ad-sig-E7/ecdCD40L vector vaccinated mice. E7-positive TC-1 cells (diamonds); E7-negative EL-4 cells (squares).

In accordance with one aspect of the invention, a method is provided for generating an immune response against an influenza antigen using an expression vector and/or the fusion protein encoded thereby. The vector includes a transcription unit encoding a secretable fusion protein containing the influenza antigen and CD40 ligand. In a preferred embodiment, the transcription unit includes from the amino terminus, a secretory signal sequence, the influenza antigen, a linker and a secretable form of CD40 ligand. In preferred embodiments, the secretable form of CD40 ligand lacks all or substantially all of its transmembrane domain.

In a preferred approach, the individual is first administered the vector on one or more occasions to generate a primary immune response. A fusion protein having the influenza antigen and CD40 ligand protein is also administered in an effective amount after administration of vector to boost the immune response to the antigen above that obtained with vector administration alone.

The term "in an effective amount" in reference to administering the fusion protein is an amount that generates an increased immune response over that obtained using the expression vector alone. A time interval between administrations is generally required for optimal results. An increase in the immune response may be measured as an increase in T cell activity or antibody production. Generally, at least one week between vector administration and protein boosting is effective although a shorter interval may be possible. An effective spacing between administrations may be from 1 week to 12 weeks or even longer. Multiple boosts may be given which may be separated by from 1-12 weeks or even longer periods of time.

The use of the fusion protein to boost the immune response avoids having to repetitively administer the expression vector which might generate hypersensitivity to multiple injections. The antigen portion of the fusion protein is preferably the fusion protein which is encoded by the transcription unit of the expression vector used in the initial administration. However, the antigen portion of the fusion protein may differ from the encoded antigen provided that there is at least one shared antigenic determinant or epitope common to the antigen of the expression vector and that of the fusion protein used for boosting.

The fusion protein may be produced in a variety of cell systems. In certain embodiments, the antigen is desired to be glycosylated. In these embodiments, if the foreign protein contains a glycosylation signal, a cell system that produces glycosylated proteins can be used, such as a eukaryotic cell, preferably a mammalian cell, Exemplary cell systems include CHO cells, COS cells, and MDCK cells. Avian cells may also be used when avian-specific glycosylation is desired. In some embodiments, glycosylation of the foreign protein portion of the fusion protein may be avoided by producing the fusion protein synthetically or by using a non-glycosylation system such as a bacterial expression system.

The fusion protein may be prepared in a mammalian cell line system, which is complementary to the vector. For example, in the case of adenovirus, the cell line system can be 293 cells that contain the Early Region 1 (E1) gene and can support the propagation of the E1-substituted recombinant adenoviruses. When the adenoviral vectors infect the production cells, the viral vectors will propagate themselves following the viral replication cycles. However, the gene of interest that is carried by the viral vector in the expression cassette will express during the viral propagation process. This can be utilized for preparation of the fusion protein encoded by the vector in the same system for production of the vector. The production of both the vector and the fusion protein will take place simultaneously in the production system. The vector and protein thus produced can be further isolated and purified via different processes.

The fusion protein may also be prepared in non-mammalian cells, such as bacterial cells. For example, cDNA encoding the fusion protein can be subcloned into a vector such as pTriEx Hygro (Novagen, Inc.) and transfected into *E. coli* (e.g., Rosetta cells from Novagen, Inc.) where the fusion protein is produced. Other non-mammalian cells include yeast, algae, insect, and plant cells.

The fusion protein may be administered parenterally, such as intravascularly, intravenously, intraarterially, intramuscularly, subcutaneously, or the like. Administration can also be orally, nasally, rectally, transdermally or inhalationally via an aerosol. The protein boost may be administered as a bolus, or slowly infused. The protein boost is preferably administered subcutaneously.

The fusion protein boost may be formulated with an adjuvant to enhance the resulting immune response. As used herein, the term "adjuvant" means a chemical that, when administered with the vaccine, enhances the immune response to the vaccine. An adjuvant is distinguished from a carrier protein in that the adjuvant is not chemically coupled to the immunogen or the antigen. Adjuvants are well known in the art and include, for example, mineral oil emulsions (U.S. Pat. No. 4,608,251, supra) such as Freund's complete or Freund's incomplete adjuvant (Freund, Adv. Tuberc. Res. 7:130 (1956); Calbiochem, San Diego Calif.), aluminum salts, especially aluminum hydroxide or ALHYDROGEL (approved for use in humans by the U.S. Food and Drug Administration), muramyl dipeptide (MDP) and its analogs such as [$Thr^1$]-MDP (Byers and Allison, Vaccine 5:223 (1987)), monophosphoryl lipid A (Johnson et al., Rev. Infect. Dis. 9:S512 (1987)), and the like, The fusion protein can be administered in a microencapsulated or a macroencapsulated form using methods well known in the art. Fusion protein can be encapsulated, for example, into liposomes (see, for example, Garcon and Six, J. Immunol. 146:3697 (1991)), into the inner capsid protein of bovine rotavirus (Redmond et al., Mol. Immunol. 28:269 (1991)) into immune stimulating molecules (ISCOMS) composed of saponins such as Quil A (Morein et al., Nature 308:457 (1984)); Morein et al., in Immunological Adjuvants and Vaccines (G. Gregoriadis al. eds.) pp. 153-162, Plenum Press, NY (1987)) or into controlled-release biodegradable microspheres composed, for example, of lactide-glycolide copolymers (O'Hagan et al., Immunology 73:239 (1991); O'Hagan et al., Vaccine 11:149 (1993)).

The fusion protein also can be adsorbed to.the surface of lipid microspheres containing squalene or squalane emulsions prepared with a PLURONIC block-copolymer such as L-121 and stabilized with a detergent such as TWEEN 80 (see Allison and Byers, Vaccines: New Approaches to Immunological Problems (R. Ellis ed.) pp. 431-449, Butterworth-Hinemann, Stoneman N.Y. (1992)). A microencapsulated or a macroencapsulated fusion protein can also include an adjuvant.

The fusion protein also may be conjugated to a carrier or foreign molecule such as a carrier protein that is foreign to the individual to be administered the protein boost. Foreign proteins that activate the immune response and can be conjugated to a fusion protein as described herein include proteins or other molecules with molecular weights of at least about 20,000 Daltons, preferably at least about 40,000 Daltons and more preferably at least about 60,000 Daltons. Carrier proteins useful in the present invention include, for example, GST, hemocyanins such as from the keyhole limpet, serum albumin or cationized serum albumin, thyroglobulin, ovalbumin, various toxoid proteins such a tetanus toxoid or diphtheria toxoid, immunoglobulins, heat shock proteins, and the like.

Methods to chemically couple one protein to another (carrier) protein are well known in the art arid include, for example, conjugation by a water soluble carbodiimide such as 1-ethyl-3-(3dimethylaminopropyl)carbodiimide hydrochloride, conjugation by a homobifunctional cross-linker having, for example, NHS ester groups or sulfo-NHS ester analogs, conjugation by a heterobifunctional cross-linker having, for example, and NHS ester and a maleimide group such as sulfosuccinimidyl-4-(N-maleimidomethyl) cyclohexane-1-carboxylate and, conjugation with gluteraldehyde (see, for example, Hermanson, Bioconjugate Techniques, Academic Press, San Diego, Calif. (1996)); see, also, U.S. Pat. Nos. 4,608,251 and 4,161,519).

The term "vector" which contains a transcription unit (aka. "expression vector") as used herein refers to viral and non-viral expression vectors that when administered in vivo can enter target cells and express an encoded protein. Viral vectors suitable for delivery in vivo and expression of an exogenous protein are well known and include adenoviral vectors, adeno-associated viral vectors, retroviral vectors, herpes simplex viral vectors, and the like. Viral vectors are preferably made replication defective in normal cells. See U.S. Pat. Nos. 6,669,942; 6,566,128; 6,794,188; 6,110,744; 6,133,029.

As used herein, the term "cells" is used expansively to encompass any living cells such as mammalian cells, plant cells, eukaryotic cells, prokaryotic cells, and the like.

The term "adenoviral expression vector" as used herein, refers to any vector from an adenovirus that includes exogenous DNA inserted into its genome which encodes a polypeptide. The vector must be capable of replicating and being packaged when any deficient essential genes are provided in trans. An adenoviral vector desirably contains at least a portion of each terminal repeat required to support the replication of the viral DNA, preferably at least about 90% of the full FUR sequence, and the DNA required to encapsidate the genome into a viral capsid. Many suitable adenoviral vectors have been described in the art. See U.S. Pat. Nos. 6,440,944 and 6,040,174 (replication defective E1 deleted vectors and specialized packaging cell lines). A preferred adenoviral expression vector is one that is replication defective in normal cells.

"Adenoviral expression vectors" may include vectors that have been modified to better target and infect specific cell types (e.g., fibroblasts and dendritic cells), or that have been modified to avoid neutralization by pre-existing, high-titer antibodies, such as the antibodies circulating in humans against Ad5 and Ad2.

Adeno-associated viruses represent a class of small, single-stranded DNA viruses that can insert their genetic material at a specific site on chromosome 19. The preparation and use of adeno-associated viral vectors for gene delivery is described in U.S. Pat. No. 5,658,785.

Non-viral vectors for gene delivery comprise various types of expression vectors (e.g., plasmids) which are combined with lipids, proteins and other molecules (or combinations of thereof) in order to protect the DNA of the vector during delivery. Fusigenic non-viral particles can be constructed by combining viral fusion proteins with expression vectors as described. Kaneda, *Curr Drug Targets* (2003) 4(8):599-602. Reconstituted HVJ (hemagglutinating virus of Japan; Sendai virus)-liposomes can be used to deliver expression vectors or the vectors may be incorporated directly into inactivated HVJ particles without liposomes. See Kaneda, *Curr Drug Targets* (2003) 4(8):599-602. DMRIE/DOPE lipid mixture are useful a vehicle for non-viral expression vectors. See U.S. Pat. No. 6,147,055. Polycation-DNA complexes also may be used as a non-viral gene delivery vehicle. See Thomas et al., *Appl Microbial Biotechnol* (2003) 62(1):27-34.

The term "transcription unit" as it is used herein in connection with an expression vector means a stretch of DNA that is transcribed as a single, continuous mRNA strand by RNA polymerase, and includes the signals for initiation and termination of transcription. For example, in one embodiment, a transcription unit of the invention includes nucleic acid that encodes from 5' to 3,' a secretory signal sequence, an influenza antigen and CD40 ligand. The transcription unit is in operable linkage with transcriptional and/or translational expression control elements such as a promoter and optionally any upstream or downstream enhancer element(s). A useful promoter/enhancer is the cytomegalovirus (CMV) immediate-early promoter/enhancer. See U.S. Pat. Nos. 5,849,522 and 6,218,140.

The term "secretory signal sequence" (aka. "signal sequence," "signal peptide," leader sequence," or leader peptide") as used herein refers to a short peptide sequence, generally hydrophobic in charter, including about 20 to 30 amino acids which is synthesized at the N-terminus of a polypeptide and directs the polypeptide to the endoplasmic reticulum. The secretory signal sequence is generally cleaved upon translocation of the polypeptide into the endoplasmic reticulum. Eukaryotic secretory signal sequences are preferred for directing secretion of the exogenous gene product of the expression vector. A variety of suitable such sequences are well known in the art and include the secretory signal sequence of human growth hormone, immunoglobulin kappa chain, and the like. In some embodiments the endogenous tumor antigen signal sequence also may be used to direct secretion.

The term "antigen" as used herein refers broadly to any antigen to which a human, mammal, bird or other animal can generate an immune response. "Antigen" as used herein refers broadly to a molecule that contains at least one antigenic determinant to which the immune response may be directed. The immune response may be cell mediated or humoral or both.

As is well known in the art, an antigen may be protein in nature, carbohydrate in nature, lipid in nature, or nucleic acid in nature, or combinations of these biomolecules. As is well known in the art, an antigen may be native, recombinant or synthetic. For example, an antigen may include non-natural molecules such as polymers and the like. Antigens include both self antigens and non-self antigens. "Self" antigens include antigens encoded by the host's genome. Self antigens include those variant sequences that arise through natural recombination events in the host genome. For example, the variable regions of immunoglobulin genes recombine in many combinations to produce a large diversity in immunoglobulins. Other self antigens may include proteins that are overexpressed or underexpressed in disease states such as cancer. For example, various mucin isoforms are overexpressed in certain cancer types.

"Foreign" antigens, as used herein refer to non-self antigens. Foreign antigens may be the products of or encoded by the genome of other organisms. For example, a foreign antigen to a mammal can be an antigen encoded by an infectious agent such as a microbe. Infectious agent antigens may be bacterial, viral, fungal, protozoan, and the like.

The term "influenza virus" as used herein refers to any of the influenza virus Types A, B and C that can infect mammals or birds. "Influenza" as used herein refers to an acute contagious influenza virus infection that is generally characterized by fever, chills, muscular pain, prostration and that generally involves the respiratory system with symptoms such as inflammation of the respiratory tract.

The term "hemagglutinin" ("HA") is a major glycoprotein that comprises over 80% of the envelope proteins present in the influenza virus particle. Heinagglutinin binds to sialic acid-containing receptors on the cell surface, bringing about the attachment of the virus particle to the cell. Hemagglutinin also is responsible for penetration of the virus into the cell cytoplasm by mediating the fusion of the membrane of the endocytosed virus particle with the endosomal membrane. Low pH in endosomes induce an irreversible conformational change in HA2, releasing the fusion hydrophobic peptide.

The term "hemagglutinin" refers to the full length protein and fragments thereof which share at least one antigenic determinant with full length hemagglutinin. "Hemagglutinin" as used herein may be native, recombinant or synthetic and may be post-transitionally modified such as by glycosylation and/or palmitoylation. There are currently at least sixteen different known subtypes of hemagglutinin characterized antigenicly, termed H1 through H16.

Hemagglutinin is synthesized as a precursor of about 566 amino acids. An exemplary amino sequence of an HA from an H5N1 virus is shown in FIG. 2 and an HA from an H3N2 virus is shown in FIG. 4. The sequence of various hemagglutinins are found in protein and nucleotide databases such as SwissProt and GenBank. See, e.g., Swiss Prot accession nos. P03437, P03441, P19694, P19695, P12581, P07976, P07977, P09345, GenBank accession no. AF036356 (H5N1 virus); and V01085 (H3N2 virus). These databases notate the various functional domains of the HA protein. For example, SwissProt accession no. P03437 discloses a sequence of an H3 hemagglutinin. This molecule is synthesized as a 566 aa precursor. Amino acids 1-16 represent a 16 aa signal sequence; 17-530 represents a 514 aa extracellular domain; 531-551 represents a 21 aa transmembrane domain; and 552-566 represents a 15 aa cytoplasmic domain. Nucleotide sequence encoding the extracellular domain of an HA is shown in FIG. 5*a*. The 566 amino acid precursor is exported to the cell membrane of influenza virus where it gets cleaved into the HA1 and HA2 subunits. The HA 1 subunit represents 17-344 of the HA precursor while the HA2 subunit represents 345-566 of the HA precursor. The HA molecule has a large extracellular domain of about 500 aa. A posttranslational cleavage by host-derived enzymes generates 2 polypeptides that remain linked by a disulfide bond. Thus, the larger N-terminal fragment HA1 which includes about 320-330 aa forms a membrane-distal globular domain (or head) of about 170 amino acids that contains the receptor-binding site and most antigenic determinants recognized by virus-neutralizing antibodies. The smaller C-terminal portion HA2 which includes about 180 aa (excluding transmembrane and cytoplasmic domain) forms a stem-like structure that anchors the globular domain to the cellular or viral membrane. The hinge region is located between the stem and globular domain.

Sixteen HA subtypes have been currently identified among influenza A viruses; three of these (H1, H2, H3) have been associated with classic influenza isolates, and 3 (H5, H7, H9) have been associated with recent sporadic human isolates. Influenza B viruses possess only 1 HA subtype. Thus, the sequence for each HA and the positions of the various functional domains of the HA can differ and are easily determined by one skilled in the art.

In some embodiments, the antigen is the entire extracellular domain of HA. Alternatively, smaller regions of the extracellular domain may serve as the antigen for invention vaccines. In choosing an antigen, one of skill in the art would recognize that one could select an antigen that is recognized by MHC class II molecules to elicit an antibody ("humoral") response or an antigen that is recognized by MHC class I molecules to illicit a cytotoxic T cell ("cellular") response. In preferred embodiments, a region of the viral protein is chosen that encompasses antigens recognized by both MHC I and MHC II. Such a region may be a contiguous stretch of amino acids from the native protein or may include discontinuous regions linked together.

In addition, antigenic regions of the HA molecule have been identified through the production of antibodies, some of which are neutralizing. The literature identifies four sites (A through D) on the HA molecule that tend to elicit antibody responses. Sites A, B, and D can be found on the head portion of the HA molecule, while site C is on the hinge (Nature 1981 289:373-8).

In one example, fragments of HA from the H5N1 strain of influenza are used as the influenza antigen. The sequence set forth in SEQ ID NO:9 represents an exemplary amino acid sequence of a precursor HA molecule from strain H5N1 (GenBank ID g2865380). The extracellular domain of this sequence is from about amino acid 17 to 530. In some embodiments, the entire extracellular domain is used as the influenza antigen. In other embodiments, one or more fragments of the extracellular domain of HA are used. Preferred fragments of the extracellular domain of SEQ ID NO:9 are shown below. Further, there are a number of epitopes predicted to bind MHC class I or MHC class II molecules within this region. Exemplary predicted MHC class I epitopes and MHC class II epitopes are underlined and italicized, respectively, in the sequences below.

(SEQ ID NO: 12)
NHFEKIQIIPKSSWSNHDASSGVSSACPYLGRSSFFRNVVWLIKKNSAYP

TIKRSYNNTNQEDLLVLWGVHHPNDAAEQTKLYQNPTTYISVGTSTLNQR

LVPEIATRPKVNGQSGRMEFFWTILKPNDAINFESN;

(SEQ ID NO: 13)
NHFEKIQIIPKSSWSNHDASSGVSSACPYLGRSSFFRNVVWLIKKNSAYP

TIKRSYNNTNQ;

(SEQ ID NO: 14)
IQIIPKSSWSNHDASSGVSSACPYLGRSSFFRNVVWLIKKNSAYPTIKRS

Y;

(SEQ ID NO: 15)
KSSWSNHDASSGVSSACPYLGRSSFFRNVVWLIKKNSAYPT;

(SEQ ID NO: 16)
TLNQRLVPEIATRPKVNGQSGRMEFFWTILKPNDAINFESN (SEQ ID NO: 17)
LVPEIATRPKVNGQSGRMEFFWTILKPNDAI;
or (SEQ ID NO: 18)
ATRPKVNGQSGRMEFFWTILK.

Additional antigen sequences are possible and may be identified with any of a number of computer programs known in the art for that purpose. For example, "SYFPEITHI is a publicly available database for MHC ligands and peptide motifs is supported by DFG-Sonderforschungsbereich, 510 and the European Union: EU BIOMED CT95-1627, BIOTECH CT95-0263, and EU QLQ-CT-1999-00713 (www.syfpeithi.de/Scripts/MHCServer.dll/EpitopePrediction.htm).

In further embodiments the focus of the influenza antigen one could design an antigen that is dominated by portions of the HA receptor binding site which elicit neutralizing antibodies (i.e., antibodies that prevent host infection by, for example, the blocking of HA binding to the HA receptor). For example, neutralizing antibodies to H5N1 (GenBank ID g2865380, SEQ ID NO:9) have been described in the literature to react mainly with (amino acid residues Y91, W149, E186, and L190 and sequences SGVSS (SEQ ID NO:19, corresponding to amino acid residues 129-133) and NGQSG (SEQ ID NO:20, corresponding to amino acid residues 220-224) (Science 279:393-6, 1998, FIG. 1). These residues are shown in FIG. 20 as underlined residues. Thus, an influenza antigen may include mainly the two sites SGVSS (SEQ ID NO:19) and NGQSG (SEQ ID NO: 20). As is known in the art, the receptor binding site can vary from HA molecule to HA molecule from different strains and even within a strain.

An exemplary "influenza antigen" includes a protein fragment representing the receptor binding region of HA from an H5N1 virus, repressing amino acids 134-205 (see FIG. 2).

Combinations of two or more of the above fragments i nay be used as the antigen. Such fragments may be joined by a linker or may be immediately adjacent to each other. One example of a combination of two fragments is (SEQ ID NO: 21)
KSSWSNHDASSGVSSACPYLGRSSFFRNVVWLIKKNSAYPTATRPKVNGQ

SGRMEFFWTILK, which represents SEQ ID NO:15 immediately adjacent and upstream of SEQ ID NO:18. One skilled in the art would recognize that these fragments could be joined with SEQ ID NO:18 upstream of SEQ ID NO:15 as well.

In another example, fragments of HA from the H3N2 strain of influenza are the influenza antigen. The sequence set forth in SEQ ID NO:10 and shown in FIG. 21 represents an exemplary amino acid sequence of a precursor HA molecule from strain H3N2 (GenBank ID Accession No. V01086). The extracellular domain of this sequence is from about amino acid 17 to 530. The extracellular domain of this sequence is from about amino acid 17 to 530. In some embodiments, the entire extracellular domain is used as the antigen in invention vaccines. In other embodiments, one or more fragments of the extracellular domain of HA are used. Preferred fragments of the extracellular domain of SEQ ID NO:10 are shown below.

Preferred fragments of the extracellular domain of SEQ ID NO:10 are shown below.

(SEQ ID NO: 22)
TITNDQIEVTNATELVQSSSTGKICNNPHRILDGINCTLIDALLGDPHCD

GFQNEKWDLFVERSKAFSNCYPYDVPDYASLRSLVASSGTLEFINEGFNW

TGVTQNGGSSACKRGPDSGFFSRLNWLYKSGSTYPVQNVTMPNNDNSDKL

YIWGVHHPSTDKEQTNLYVQASGKVTVSTKRSQQTIIPNVGSRPWVRGLS

SRISIYWTIVKPGDILVINSNGNLIAPRGYFK.

SEQ ID NO:22 comprises antigenic regions recognized by MHC class I molecules. The following sequences represent exemplary MHC class I epitopes.

(SEQ ID NO: 23)
TITNDQIEV;

(SEQ ID NO: 24)
ILDGINCTLIDA;

(SEQ ID NO: 25)
LFVERSKAF;

(SEQ ID NO: 26)
PYDVPDYASLRSLVASSG;

(SEQ ID NO: 27)
WLYKSGSTY

-continued (SEQ ID NO: 28)
NNDNSDKLY;
and (SEQ ID NO: 29)
STDKEQTNLY.

SEQ ID NO:22 comprises antigenic regions recognized by MHC class H molecules. The following sequences represent exemplary MHC class II epitopes.

(SEQ ID NO: 30)
TELVQSSSTGKICNN;

(SEQ ID NO: 31)
PHRILDGINCTLIDA;
and (SEQ ID NO: 32)
VPDYASLRSLVASSG.

Further preferred fragments include those residues reported to be involved in receptor binding of a precursor HA molecule from strain H3N2 (SEQ ID NO:10). Such residues are shown in FIG. 21 as underlined residues. Thus, preferred fragments include, for example, EFINEG (SEQ ID NO:33). A further preferred fragment is KAFSNCYPYDVPDY (SEQ ID NO:34) which has been shown to be an epitope against which neutralizing antibodies have been generated (Int Arch Allergy Immunol 2002 127:245-50).

One of skill in the art would recognize one could join two or more of the above sequences to form an antigen. Further one could extend the sequence of any of the fragments by, for example, 5 amino acids or more preferably, 10 amino acids, on either end or both ends.

The term neuraminidase ("NA") as used herein refers to a glycoprotein found on the surface of influenza viruses. Neuraminidase catalyses the removal of terminal sialic acid residues of glycosyl groups, thereby destroying potential receptors for HA. It is believed that neuraminidase ensures the efficient spread of the virus by dissociating the mature virions from the neuraminic acid containing glycoproteins. Thus, NA-specific antibodies inhibit the release of newly formed virus from infected host cells and thereby limit the spread and shedding of virus during infection.

The term "neuraminidase" refers to the full length protein and fragments thereof which share at least one antigenic determinant with full length neuraminidase. "Neuraminidase" as used herein may be native, recombinant or synthetic and may be post-translationally modified such as by glycosylation. There are currently at least nine neuraminidase sub-types.

Neuraminidase is synthesized as a precursor of about 469 amino acids. The sequence of various NA are found in protein and nucleotide databases such as Swiss-Prot and GenBank. See, e.g., Swiss-Prot accession nos P06818, P26143, Q9Q0U7, P06820, GenBank accession no. AF028708 (H5N1 virus), and AB124658 (H3N2 virus). These databases annotate the various functional domains of the NA protein. For example, SwissProt accession no. P06818 discloses a sequence of an N2 Neuraminidase from influenza A virus (strain A/Bangkok/1/79). This molecule is synthesized as a 469 aa precursor. Amino acids 1-6 represent a 6 aa cytoplasmic domain; 7-35 represent a 29 aa transmembrane domain; and 36-469 represents a 434 aa extracellular domain. The extracellular domain consists of a 55 aa hypervariable stalk region (amino acid residues 36 through 90) and a 379 aa head region (amino acid residues 91 through 469). The sequence for each NA and the positions of the various functional domains of the NA can differ and are easily determined by one skilled in the art.

In some embodiments, the influenza antigen is from the neuraminidase protein In preferred embodiments, the entire extracellular domain of neuraminidase is used as the influenza antigen. Alternatively, fragments of the extracellular domain may also be selected as the influenza antigen. In such fragments, one of skill in the art can use any of a number of computer software programs for choosing antibody epitopes or antigens for MHC class I or MHC class II molecules, known in the art and discussed above. In preferred embodiments the antigen is focused around regions of the neuraminidase protein known in the art to be antigenic and, more particularly, regions which include residues of known escape mutants. "Escape mutants" as used herein are proteins which have a mutation in an antigenic region such that an antibody that previously bound to that region will no longer bind. In this way, such mutants escape or evade an immune response. In other embodiments, one or more fragments of the extracellular domain of NA are used.

In one example, the influenza antigen is neuraminidase from influenza virus A/Memphis/31/98, H3N2. An exemplary sequence NA from H3N2 is set forth in SEQ ID NO:11 (GenBank ID No, g30385699) and is shown in FIG. 22. The extracellular domain of SEQ ID NO:11 is indicated in FIG. 22 (shaded region) and is the influenza antigen in some embodiments. Furthermore, several escape mutants have been described in the literature. For example, Gulati and coworkers describe escape mutants with mutations at amino acid positions 198, 199, 220, and 221 (underlined and in bold in FIG. 22) (J Virol 2002 76(23):12274-80). Preferred fragments of SEQ ID NO:11 are shown below.

QCKITGFAPFSKDNSIRLSAGGDIWVTREPYVSCDPDKCYQFALGQGTTL

NNRHSNDTVHDRTPYRTLLMNELGVPFHLGTKQVCIAWSSSSCHDGKAWL

HVCVTGHDENATASFIYDGRLVDSIGSWSKKILRTQESECVCINGTCTVV

MTDGSASGRADTKILFIEEGKIVHISPLSGSAQHVEECSCYPRYPGVRCV

CRDNWKGSNRPIVDINVKDYSIVSSYVCSGLVGDTPRKNDSSSSSHCLNP

NNEEGGHGVKGWAFDDGNDVWMGRTISEKFRSGYETFKVIEGWSKPNSKL

QINRQVIVDRGNRSGYSGIFSVEGKSCINRCFYVELIRGRKQETEVWWTS

NSIVVFCGTSGTYGTGSWPDGADINLMPI (SEQ ID NO: 35, corresponds to the head region of NA);

AWLHVCVTGHDENATASFIYDGRLVDSIGSWSKKILRTQESECV (SEQ ID NO: 36);

CVTGHDENATASFIYDGRLVDSIGSWSKKILRTQ (SEQ ID NO: 37);
and

DENATASFIYDGRLVDSIGSWSKK (SEQ ID NO: 38).

The term Matrix protein 2 ("M2") as used herein refers to an integral membrane protein expressed on the surface of the influenza virus and the infected cells. M2 is expressed at high levels of influenza virus infected cells, and compared to hemagglutinin and neuraminidase has a stable sequence from year to year among different influenza strains. Although this protein is not typically immunogenic, it has been shown that chimeric molecules made from the extracellular domain of M2 and "adjuvant proteins" such as the hepatitis B core protein induce a potent immune response. (Virology 2005 337:149-161; Infection and Immunity 2002 70:6860-70).

M2 is synthesized as a precursor of about 109 amino acids. An exemplary amino sequence of an M2 from an H5N1 virus is shown in FIG. 1 and an M2 from an H3N2 virus is shown in FIG. 3. The sequence of various M2 are found in protein and nucleotide databases such as SwissProt and GenBank. See, e.g., Swiss Prot accession nos. P13881, P13882, P03493, Q80DN6, P08383, P0C0X4, P21430, P03491, GenBank accession no. AF036358 (H5N1 virus); and AAA43276 (H3N2 virus). These databases annotate the various functional domains of the M2 protein. For example, SwissProt accession no. P21430 (influenza A virus) discloses a sequence of an M2. This molecule is synthesized as a 97 aa precursor. Amino acids 1-22 represent a 22 aa extracellular domain; 23-43 represents a 21 aa transmembrane domain; and 44-97 represents an 54 aa cytoplasmic domain. Nucleotide sequence encoding the extracellular domain of an M2 is shown in FIG. 5*b*. The sequence for each M2 and the positions of the various functional domains of the M2 can differ and are easily determined by one skilled in the art. For example, M2 from Influenza B virus has a very short 4 aa extracellular domain.

The term "influenza antigen" as used herein refers to any part, portion or region of an influenza virus protein that can elicit an immune response in mammals or birds. Influenza antigens can be native, recombinant or synthetic. An "influenza antigen" may be include epitopes derived from a single viral type or strain or from multiple viral types or strains. An "influenza antigen" may be a fission protein of epitopes from the same or different viral types or strains, An "influenza antigen" as used herein may include the HA, NA or M2 protein, or fragments thereof containing one or more epitopes; an "influenza antigen" may contain the entire extracellular domain of HA, NA or M2, the cytoplasmic domain of HA, NA or M2 and/or any immunogenic combination of these proteins or domains.

An exemplary extracellular domain of M2 from Hong Kong/485/97(H5N1) matrix protein 2 (GenBank Accession No:AJ278648)

```
(SEQ ID NO: 39)
MSLLTEVDTLTRNGWGCRCSDSSD,
```

which is encoded by the nucleotide sequence

```
(SEQ ID NO: 40)
5'-ATG AGC CTT CTA ACC GAG GTT GAC ACG CTT ACC AGA

AAC GGA TGG GGG TGC AGA TGC AGC GAT TCA AGT GAT-

3'.
```

A further example of an M2 antigen Influenza A virus (A/New York/522/1997(H3N2) CY006508) is

```
(SEQ ID NO: 41)
5'-ATGAGCC TTCTAACCGA GGTCGAAACACC TATCAGAAACGA AT

GGGGGT GCAGATGCAA CGATTCAAGT GAC-3'.
```

The above sequence encodes the following sequence, corresponding to amino acids 1-24 of the M2 protein,

```
(SEQ ID NO: 42)
MSLLTEVETPIRNEWGCRCNDSSD
```

Another example of an influenza antigen is a chimeric protein having a segment of an HA and a segment of an M2 protein (e.g. from an H5N1 or H3N2 virus). In one example of a chimeric influenza antigen is the following sequence which encodes an HA-M2 chimera from H5N1.

```
(SEQ ID NO: 43)
5'-AAAAGTTCTTGGTCCAATCATGATGCCTCATCAGGGGTGAGCTC

AGCATGTCCATACCTTGGGAGGTCCTCCTTTTTCAGAAATGTGGTATGGC

TTATCAAAAAGAACAGTGCATACCCAACAGCTACTAGACCCAAAGTAAAC

GGGCAAAGTGGAAGAATGGAGTTCTTCTGGACAATTTTAAAG GATATC

ATGA GCCTTCTAAC CGAGGTTGAC ACGCTTACCAGAAACGGATGGG

GGTGCAGATG CAGCGATTCAAGTGAT-3'.
```

In the above exemplary sequence the HA and M2 fragments are joined by an optional 2 amino acid linker (nucleotides encoding the linker are underlined in the sequence above). The HA fragment precedes the linker and the M2 fragment follows the linker. One of skill in the art would recognize that the order of these fragments could be reversed with the M2 fragment preceding the HA fragment. An exemplary nucleotide sequence encoding such a fragment is below.

```
(SEQ ID NO: 44)
5'-ATGAGCCTTCTAACCGAGGTTGACACGCTTACCAGAAACGGATGGGG

GTGCAGATGCAGCGATTCAAGTGATAAAAGTTCTTGGTCCAATCATGATG

CCTCATCAGGGGTGAGCTCAGCATGTCCATACCTTGGGAGGTCCTCCTTT

TTCAGAAATGTGGTATGGCTTATCAAAAAGAACAGTGCATACCCAACAGC

TACTAGACCCAAAGTAAACGGGCAAAGTGGAAGAATGGAGTTCTTCTGGA

CAATTTTAAAG-3'.
```

Another example of a chimeric influenza antigen includes fragments of HA and M2 (underlined) from H3N2 and is as follows,

```
(SEQ ID NO: 45)
TITNDQIEVTNATELNQSSSTGKICNNPHRILDGINCTLIDALLGDPHCD

GFQNEKWDLFVERSKAFSNCYPYDVPDYASLRSLVASSGTLEFINEGFNW

TGVTQNGGSSACKRGPDSGFFSRLNWLYKSGSTYPVQNVTMPNNDNSDKL

YIWGVHHPSTDKEQTNLYVQASGKVTVSTKRSQQTIIPNVGSRPWVRGLS

SRISIYWTIVKPGDILVINSNGNLIAPRGYFKMSLLTEVETPIRNEWGCR

CNDSSD.
```

Other chimeras can be constructed from fragments of neuraminidase and M2 or HA. For example, the following sequence consists of the head region of neuraminidase and a the extracellular domain of M2 (underlined), both from H3N2.

```
(SEQ ID NO: 46)
QCKITGFAPFSKDNSIRLSAGGDIWVTREPYVSCDPDKCYQFALGQGTTL

NNRHSNDTVHDRTPYRTLLMNELGVPFHLGTKQVCIAWSSSSCHDGKAWL

HVCVTGHDENATASFIYDGRLVDSIGSWSKKILRTQESECVCINGTCTVV

MTDGSASGRADTKILFIEEGKIVHISPLSGSAQHVEECSCYPRYPGVRCV
```

-continued

CRDNWKGSNRPIVDINVKDYSIVSSYVCSGLVGDTPRKNDSSSSSHCLNP

NNEEGGHGVKGWAFDDGNDVWMGRTISEKFRSGYETFKVIEGWSKPNSKL

QINRQVIVDRGNRSGYSGIFSVEGKSCINRCFYVELIRGRKQETEVWWTS

NSIVVFCGTSGTYGTGSWPDGADINLMPIMSLLTEVETPIRNEWGCRCND

SSD.

One of skill in the art would recognize that fragments from different proteins of different strains of influenza viruses may be combined to form an antigen. In some embodiments. M2 comprises one of the two fragments. In the following example, a fragment of HA from H5N1 is combined with an M2 fragment (underlined) from H3N2, (SEQ ID NO: 47)

KSSWSNHDASSGVSSACPYLGRSSFFRNVVWLIKKNSAYPTATRPKVNGQ

SGRMEFFWTILK MSLLTEVETPIRNEWGCRCNDSSD.

As used herein, an "influenza antigen-CD40L" means an influenza protein linked to CD40L. For example, this may be an H3N2 or H5N1 HA antigen linked to CD40L; an H3N2 or H5N1 HA-M2 chimeric antigen linked to CD40L; or an H3N2 or H5N1 M2 linked to CD40L. Although the above examples list H3N2 and H5N1, an "influenza antigen" as used herein refers to antigens expressed by an influenza virus and includes proteins or fragments from other Type A, B or C influenza viruses.

A secretable form of an antigen is one that lacks all or substantially all of its transmembrane domain, if present in the mature protein. For example, in the case of a hemagglutinin, the transmembrane domain, if present, is generally about 19-21 amino acids in length and functions to anchor the hemagglutinin or a fragment of the hemagglutinin in the cell membrane. For example, in the case of the hemagglutinin disclosed in SwissProt accession no. P03437, a secretable form of this hemagglutinin in which the transmembrane domain has been deleted is missing residues 531-551 of the precursor protein. A hemagglutinin missing substantially all of the transmembrane domain is one where the domain comprises 6 residues or less of sequence at one end of the transmembrane domain, more preferably less than about 4 residues of sequence at one end of the transmembrane domain, even more preferably less than about 2 residues of sequence on one end of the transmembrane domain, and most preferably 1 residue or less on one end of the transmembrane domain. In a preferred embodiment, the vaccine vector transcription unit encodes a secretable form of a hemagglutinin lacking the entire transmembrane domain. A hemagglutinin that lacks substantially all of the transmembrane domain rendering the hemagglutinin secretable is one that contains no more than six residues of sequence on one end of the domain. The extracellular domain of a human HA is denoted herein as "ecdHA."

It should be understood that a hemagglutinin, neuraminidase or M2 protein which lacks a functional transmembrane domain (i.e., is in secretable form) may still include all or a portion of the cytoplasmic domain.

A source of DNA encoding the various hemagglutinins, neuraminidases or M2 antigens may be obtained from hemagglutinins, neuraminidases or M2 expressing cell lines using a commercial cDNA synthesis kit and amplification using a suitable pair of PCR primers that can be designed from the published DNA sequences. Hemagglutinin, neuraminidase or M2 encoding DNA also may be obtained by amplification from RNA or cDNA obtained or prepared from infected human or other animal tissues or cells, or from viral isolates. For DNA segments that are not that large, the DNA may be synthesized using an automated oligonucleotide synthesizer.

The term "linker" as used herein with respect to the transcription unit of the expression vector refers to one or more amino acid residues between the carboxy terminal end of the antigen and the amino terminal end of CD40 ligand. The composition and length of the linker may be determined in accordance with methods well known in the art and may be tested for efficacy. (See e.g. Arai et al., design of the linkers which effectively separate domains of a bifunctional fusion protein. *Protein Engineering,* Vol. 14, No. 8, 529-532, August 2001). The linker is generally from about 3 to about 15 amino acids long, more preferably about 5 to about 10 amino acids long, however, longer or shorter linkers may be used or the linker may be dispensed with entirely. Longer linkers may be up to about 50 amino acids, or up to about 100 amino acids. A linker of about 30 residues is preferred when the M2 or hemagglutinin antigen is N-terminal to the CD40 ligand. One example of a linker well-known in the art is a 15 amino acid linker consisting of three repeats of four glycines and a serine (i.e., $[Gly_4Ser]_3$).

The term "CD40 ligand" (CD40L) as used herein refers to a full length or portion of the molecule known also as CD154 or TNFS. CD40L is a type II membrane polypeptide having a cytoplasmic domain at its N-terminus, a transmembrane region and then an extracellular domain at its C-terminus. Unless otherwise indicated the full length CD40L is designated herein as "CD40L," "wtCD40L" or "wtTmCD40L." The form of CD40L in which the cytoplasmic domain has been deleted is designated herein as "ΔCtCD40L." The form of CD40L where the transmembrane domain has been deleted designated herein as "ΔTmCD40L." The form of CD40L where both the cytoplasmic and transmembrane domains have been deleted is designated herein as "ΔCtΔTmCD40L" or "ecdCD40L." The nucleotide and amino acid sequence of CD40L from mouse and human is well known in the art and can be found, for example, in U.S. Pat. No. 5,962,406 (Armitage et al.). Also included within the meaning of CD40 ligand are variations in the sequence including conservative amino acid changes and the like which do not alter the ability of the ligand to elicit an immune response to a mucin in conjunction the fusion protein of the invention.

Murine CD40L (mCD40L) is 260 amino acids in length. The cytoplasmic (Ct) domain of mCD40L extends approximately from position 1-22, the transmembrane domain extends approximately from position 23-46, while the extracellular domain extends approximately from position 47-260.

Human CD40L (hCD40L) is 261 amino acids in length. The cytoplasmic domain of hCD40L extends approximately from position 1-22, the transmembrane domain extends approximately from position 23-46, while the extracellular domain extends approximately from position 47-261, The phrase "CD40 ligand is missing all or substantially all of the transmembrane domain rendering CD40 ligand secretable" as used herein refers to a recombinant form of CD40 ligand that can be secreted from a cell. The transmembrane domain of CD40L which contains about 24 amino acids in length, functions to anchor CD40 ligand in the cell membrane. CD40L from which all of the transmembrane domain has been deleted is CD40 ligand lacking residues 23-46. CD40 ligand missing substantially all of the transmembrane domain is one that comprises 6 residues or less of the transmembrane domain, more preferably less than about 4 residues of transmembrane domain sequence, even more preferably less than about 2 residues of transmembrane domain sequence and most preferably 1 residue residues from the transmembrane domain sequence. Any transmembrane sequence that is present from the CD40L may be at one end of the domain or may constitute transmembrane domain sequence contributed by both ends. Thus, a CD40L that lacks substantially all of the transmembrane domain rendering the CD40L secretable is one that retains no more than six residues of sequence of the transmembrane domain. Such as CD40L would contain, in addition to the extracellular domain and optionally the cytoplasmic domain, no more than amino acids 41-46 or 23-28, or a combination totaling 6 residues or less from both ends of the transmembrane domain of CD40L. In a preferred embodiment, the vaccine vector transcription unit encodes a secretable form of CD40 containing less than 10% of the transmembrane domain. More preferably, CD40L contains no transmembrane domain.

It should be understood that a CD40L which lacks a functional transmembrane domain may still include all or a portion of the cytoplasmic domain. Likewise, a CD40L which lacks a functional transmembrane domain may include all or a substantial portion of the extracellular domain.

Expression vectors encoding a secretable fusion protein that includes an influenza antigen and CD40 ligand can be constructed in accordance with methods known in the art. See, e.g., U.S. Patent Application Publication US 2005-0226888 (application Ser. No. 11/009,533) titled "Methods for Generating Immunity to Antigen," filed Dec. 10, 2004, which is incorporated herein in its entirety including the drawings.

As used herein, an expression vector and fusion protein boost is administered as a vaccine to induce immunity to an influenza antigen. The expression vector and protein boost may be formulated as appropriate with a suitable pharmaceutically acceptable carrier. Accordingly, the vectors or protein boost may be used in the manufacture of a medicament or pharmaceutical composition. Expression vectors and the fusion protein may be formulated as solutions or lyophilized powders for parenteral administration. Powders may be reconstituted by addition of a suitable diluent or other pharmaceutically acceptable carrier prior to use. Liquid formulations may be buffered, isotonic, aqueous solutions. Powders also may be sprayed in dry form. Examples of suitable diluents are normal isotonic saline solution, standard 5% dextrose in water, or buffered sodium or ammonium acetate solution. Such formulations are especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, sodium citrate, and the like.

Alternately, expression vectors and the fusion protein may be prepared for oral administration. Pharmaceutically acceptable solid or liquid carriers may be added to enhance or stabilize the composition, or to facilitate preparation of the vectors. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. When a liquid carrier is used, the preparation may be in the form of a syrup, elixir, emulsion, or an aqueous or non-aqueous suspension.

Expression vectors and the fusion protein may be formulated to include other medically useful drugs or biological agents. The vectors also may be administered in conjunction with the administration of other drugs or biological agents useful for the disease or condition that the invention compounds are directed.

As employed herein, the phrase "an effective amount," refers to a dose sufficient to provide concentrations high enough to generate (or contribute to the generation of) an immune response in the recipient thereof. The specific effective dose level for any particular subject will depend upon a variety of factors including the disorder being treated, the severity of the disorder, the activity of the specific compound, the route of administration, the rate of clearance of the viral vectors, the duration of treatment, the drugs used in combination or coincident with the viral vectors, the age, body weight, sex., diet, and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990. For administration of vectors, the range of particles per administration typically if from about $1\times10^7$ to $1\times10^{11}$, more preferably $1\times10^8$ to $5\times10^{10}$, and even more preferably $5\times10^8$ to $2\times10^{10}$. A vector can be administered parenterally, such as intravascularly, intravenously, intraarterially, intramuscularly, subcutaneously, or the like, Administration can also be orally, nasally, rectally, transdermally or inhalationally via an aerosol. The vectors may be administered as a bolus, or slowly infused. The vector is preferably administered subcutaneously.

As described herein, vectors encoding influenza antigens can induce a protective cellular and humoral immunity against such antigens, including those to which tolerance had developed. Although not wishing to be bound by any theory, it is believed that the invention vaccines generate upon administration a continual local release of the fusion protein composed of the secretable form of the antigen linked to a secretory form of CD40 ligand. As demonstrated herein this facilitates DCs maturation, promoting the development of effective antigen-specific immunity. It is also demonstrated herein that the secretable fusion protein encoding the extracellular domain of H5N1 HA and the murine CD40L lacking a transmembrane and cytoplasmic domain (i.e. H5HA-ΔCtΔTmCD40L) produced from an adenoviral vector dramatically increased the number of CD8 T cells responsive to H5HA. Although not wishing to be bound by any theory, it is believed that subcutaneous injection of the Ad-sig-HSHA-ΔCtΔTmCD40L vector elicits a strong HA specific $CD8^+$ T cell-mediated immunity.

The immunity generated against the antigens using the invention methods is long lasting. As used herein, the term long lasting means that immunity elicited by the antigen encoded by the vector can be demonstrated for up to 6 months from the last administration, more preferably for up to 8 months, more preferably for up to one year, more preferably up to 1.5 years, and more preferably for at least two years.

In one embodiment, immunity to an influenza hemagglutinin can be generated by producing a fusion protein that comprises part of the extracellular domain of the hemagglutinin fused to the amino-terminal end of the CI)40 ligand from which the transmembrane and cytoplasmic domains were deleted. Construction of such vector is disclosed in the Examples. As was observed herein, subcutaneous administration of this adenoviral vector hemagglutinin vaccine induced a $CD8^+$ cytotoxic T cell lymphocyte dependent systemic immune response.

Although not wishing to be bound by any theory, it is believed that the cells infected in the vicinity of the site of subcutaneous injection of the vector release the antigen/CD40 ligand secretory which is taken up by antigen presenting cells (e.g. DCs) in the vicinity of the infected cells. The internalized influenza antigen would be digested in the proteosome with the resultant influenza antigen peptides trafficking to the endoplasmic reticulum where they would bind to Class I MHC molecules. Eventually, the DCs would present the influenza antigen on the surface in the Class I MHC molecule. Activated, influenza antigen-loaded antigen presenting cells would migrate to lymphocyte bearing secondary organs such as the regional lymph nodes or the spleen. During the two weeks of continuous release of the antigen/CD40 fusion protein, CD8 cytotoxic T cell lymphocytes competent to recognize and kill cells, which carried the antigens, would be expanded in the lymph nodes and spleen by the presence of the activated and antigen loaded dendritic cells. The continuous nature of the stimulation and the expansion of the influenza antigen specific cytotoxic T cells by the continuous release from the vector infected cells is believed to generate an immune response which would be greater in magnitude than is possible using a vector which carried an antigen/CD40 ligand which is non-secretory.

Methods to test the novel influenza vaccines, proteins and vaccination methods of the present invention may include in vitro and in vivo methods well known in the art, method as described herein, and may also involve methods utilizing mouse models and viruses that have been mouse adapted. For example, the laboratories of M. K. Sim and Vincent Chow at the National University of Singapore's School of Medicine have developed a mouse model for the study of the Ad-sig-H3N2/ecdCD40L vaccine against H3N2 influenza A virus. The A/Aichi/2/68 (H3N2) strain (Arch. Virol. 1983 75:17-27; Virology 1995 212:526-534) was mouse-adapted by passaging through several batches of 2 month old mice via intranasal administration. Briefly, influenza virus was initially administered intranasally to 6 week-old female BALB/c mice. Two days later, the animals were sacrificed, lung homogenates prepared and labeled as "passage-1 lung homogenate". A second batch of BALB/c mice was infected with 50 μL of passage-1 lung homogenate, and the process of passaging was repeated. The virus virulence and titer in each passage of lung homogenate was monitored by assaying its infectivity in Madin-Darby canine kidney (MDCK) cells, host cells which are permissive for influenza A virus replication. The influenza A virus titer increased progressively with each passage. Thus it is possible to adapt an H3N2 influenza virus to the Balb/C mouse strain.

In similar fashion, an H5N1 influenza virus may also be adapted to a mouse strain by passaging through several batches of 2 month old mice via intranasal administration, using the method of Chow described above. Briefly, the virus is initially administered intranasally to 6 week-old female BALB/c mice. Two days later, the animals are sacrificed, lung homogenates prepared and labeled as "passage-1 lung homogenate," A second batch of BALB/c mice is infected with 50 μL of passage-1 lung homogenate, and the process of passaging is repeated. The virus virulence and titer in each passage of lung homogenate is monitored by assaying its infectivity in host cells which are permissive for H5N1 virus replication.

In a further aspect, the invention provides methods of effectively immunizing older individuals by administering an expression vector encoding a secretable fusion protein which includes an antigen and CD40 ligand. Older individuals which may realize an improved immune response using the methods of the invention as compared to other immunization methods are at least 50 years of age, or even at least 55 years of age or even yet at least 60 years of age.

The invention methods are advantageous over traditional vaccination in providing increased immune responses in older individuals. The benefits of immunizing older individuals, at least 50 years of age, or event at least 55 years of age or even at least 60 years of age is afforded for antigens including cancer antigens (tumor associated or tumor specific) or infectious agent antigens. Infectious agent antigens may be bacterial, viral, fungal, protozoan, and the like. Viral antigens may be an influenza antigen as described above. The viral antigen may be from a human papilloma virus. The viral antigen may be the E6 or E7 protein of human papilloma virus.

The term "tumor associated antigen" (TAA) as used herein refers to a protein which is present on tumor cells, and on normal cells during fetal life (onco-fetal antigen), after birth in selected organs, or on many normal cells, but at much lower concentration than on tumor cells. A variety of TAA are described that can be used in the invention methods for immunizing older individuals are described in U.S. Patent Application Publication US 2005-0226888 (application Ser. No. 11/009,533) titled "Methods for Generating Immunity to Antigen," filed Dec. 10, 2004. The patent publication describes various mucin TAA including MUC1 and tandem repeats of the mucin VNTR region, and HER2 (neu). Other TAA include but are not limited to carcinoembryonic antigen, prostate specific antigen, CA 125, CA 15-3, and EFGr.

As used herein, tumor specific antigen (TSA) (aka, "tumor-specific transplantation antigen or TSTA) refers to a protein absent from normal cells. TSAs usually appear when an infecting virus has caused the cell to become immortal and to express a viral antigen(s). An exemplary viral TSA is the E6 or E7 proteins of HPV type 16. TSAs not induced by viruses include idiotypes the immunoglobulin idiotypes associated with B cell lymphomas or the T cell receptor (TCR) on T cell lymphomas.

The following examples serve to illustrate the present invention. These examples are in no way intended to limit the scope of the invention.

EXAMPLES

1. Construction of Adenoviral Expression Vectors (General Considerations)

Details for constructing adenoviral expression vectors containing a transcription unit encoding a fusion protein that includes an antigen fused to CD40 ligand can be found in U.S. Patent Application Publication US 2005-0226888 (application Ser. No. 11/009,533) titled "Methods for Generating Immunity to Antigen," filed Dec. 10, 2004. This publication describes the preparation of expression vector sig-ecdhMUC1-ΔCtΔTmCD40L, which encodes a signal sequence (from an Ig kappa chain) followed by the extracellular domain of human MUC1 which is connected via a linker to a fragment of the CD40 ligand (human or mouse), which contains the extracellular domain without the transmembrane or cytoplasmic domains. The fusion protein was engineered to be secreted from vector infected cells by the addition of the kappa chain signal sequence to the amino-terminal end of the fusion protein. As described therein, the transcription unit was introduced into the E1 gene region of the adenoviral vector backbone. After the adenoviral vector particles were generated in HEK 293 cells, the vector DNA was purified by cesium chloride gradient centrifugation. The presence of the signal peptide in the adenoviral vector was confirmed by restriction enzyme analysis and by DNA sequencing.

U.S. Patent Application Publication US 2005-0226888 also describes how to prepare a transcription unit that includes DNA encoding the signal sequence of the mouse IgG kappa chain gene upstream of DNA encoding human MUC-1 ("sig-ecdhMUC-1"). The transcription unit is formed with the assistance of pShuttle-ΔCtΔTmCD40L (no signal sequence and murine CD40L) as described in U.S. Patent Application Publication US 2005-0226888. Primers are used to encode spacer (linker) between the antigen and CD40L (a 10 residue spacer LENDAQAPKS; single letter code; SEQ ID NO:48). The sig-ecdhMUC 1/ΔCtΔTmCD40L encoding DNA was cut from the pCDNA3TOPO vector using HindIII-XbaI restriction and inserted into pShuttle-CMV (see Murphy et al., *Prostate* 38: 73-78, 1999) downstream of the CMV promoter. The plasmid is designated pShuttle-sig-ecdhMUC1-ΔCtΔTmCD40L and contains transcription unit sig-ecdhMUC1-ΔCtΔTmCD40L which encodes the mouse IgG kappa chain secretory signal followed by the extracellular domain of human MUC1 followed by a 10 amino acid linker with (LENDAQAPKS; SEQ ID NO:48) followed by murine CD40 ligand residues 52-260.

U.S. Patent Application Publication US 2005-0226888 also describes cloning the mouse HSF1 trimer domain which was added between the ecdhMUC1 (antigen) encoding DNA and ΔCtΔTm CD40L by PCR. The construction design includes use of a spacer on each end of the trimer segment. U.S. Patent Application Publication US 2005-0226888 also describes use of PCR to add a His tag encoding sequence added to the end of the ΔCtΔTm CD40L.

The recombinant adenoviral vectors were generated using the AdEasy vector system (Stratagene, San Diego, Calif.). Briefly the resulting plasmid pShuttle-sig-ecdhMUC1-ΔCtΔTmCD40L, and other control adenoviral vectors were linearized with Pme I and co-transformed into *E. coli* strain BJ5183 together with pAdEasy-1, the viral DNA plasmid. Recombinants were selected with kanamycin and screened by restriction enzyme analysis. The recombinant adenoviral construct was then cleaved with Pac I to expose its Inverted Terminal Repeats (ITR) and transfected into 293A cells to produce viral particles. The titer of recombinant adenovirus was determined by the Tissue culture Infectious Dose ($TCID_{50}$) method.

2. Production of the Fusion Protein and Vector

The influenza virus antigen fusion protein was produced directly from an adenoviral vector that carries the expression cassette of the fusion gene encoding the fusion protein. The production cells (e.g. 293 cell line) at 80% confluency in growth medium were infected with the viral vector at the ratio of 10-100 viral particles per cell. The infected cells were further cultured for 48-72 hours, when the viral vectors propagated in the cells and the tumor antigen fusion proteins were expressed in the cells and secreted into culture media. The infected cells were collected when 70-90% of them showed cytopathic effect (CPE). The cell culture media was collected separately. Cell lysates were prepared through 3-time freeze-and-thaw cycles. The viral particles were isolated via the standard procedure (see e.g., PNAS 2003 100:15101-15106; Blood 2004 104:2704-2713)). The tumor antigen fusion proteins were purified through affinity chromatograph from the collected cell media.

The fusion protein also were produced in bacterial cells as follows. The cDNA encoding the fusion protein was subcloned into the pTriEx-2 hygro Vectors (Novagen). Competent cells (Rosetta™ cells, Novagen Inc.) were transformed with the resulting plasmid. Following incubation of the cells in IPTG supplemented medium for 4 hours, a cell lysate was prepared using the CelLytic™ B Plus Kit (Sigma). The fusion protein was purified from the soluble fraction by HIS-select Nickel Affinity Gel (Sigma). Then, the protein was concentrated and desalted by centrifugation through an Ultrafree-15 Biomax-50 filter (Millipore) and eluted with PBS.

3. Construction of Adenoviral Vectors Encoding HPV E7-CD40 Ligand Fusion Protein.

E7 is a protein encoded by the human papilloma virus which appears on all HPV associated dysplastic and neoplastic cells. The transcription unit included DNA encoding the signal peptide from the HGH gene, upstream of DNA encoding the full-length HPV type 16 E7 protein, consisting of 98 amino acids and having the following amino acid sequence:

(SEQ ID NO: 49)
MHGDTPTLHEYMLDLQPETTDLYCYEQLNDSSEEEDEIDGPAGQAEPDRA

HYNIVTFCCKCDSTLRLCVQSTHVDIRTLEDLLMGTLGIVCPICSQKP.

The coding sequence for this E7 protein was upstream of the coding sequence of a 10 aa spacer, which was upstream of the coding sequence of the coding sequence of ΔCtΔTmCD44L in the transcription unit.

Construction of an adenoviral vector expressing a transcription unit fusion protein constituting E7 linked to a secretable form of CD40 ligand has been described See, e.g., U.S. Patent Application Publication US 2005-0226888 (application Ser. No. 11/009,533) titled "Methods for Generating Immunity to Antigen," filed Dec. 10, 2004. This approach is detailed below.

a) Construction of pShuttle-sp-ΔCtΔTmCD40L(No Signal Sequence).

Plasmid pDC406-mCD40L was purchased from the American Type Culture Collection. A pair of PCR primers (SEQ ID NOs:50 and 51) was designed to amplify the mouse CD40 ligand from position 52 to 260 (i.e., without the cytoplasmic and transmembrane domains) and include sequence encoding a linker (indicated as "+ spacer") at the 5' end of the amplicon.

Mouse ΔCtΔTmCD40L+ spacer forward primer (MCD40LSPF) (Xho I recognition site in bold and underlined; spacer sequence underlined (includes the Xho I site); CD40L sequence italicized):

(SEQ ID NO: 50)
5'-CCG CTCGAG AAC GAC GCA CAA GCA CCA AAA TCA

*AAG GTC GAA GAG GAA GTA AAC*-3'.

Mouse CD40L reverse primer (MCD40LR) (Xba I recognition site in bold and underlined)

```
                                        (SEQ ID NO: 51)
5'-CCC TCTAGA ATCAGAGTTTCACTAAGCCAA-3'.
```

The forward primer MCD40LSPF encoded a 10 residue spacer (LENDAQAPKS; single letter code; SEQ ID NO:48) to be located between the tumor antigen and the CD40 ligand (mCD40L) of the transcription unit. PCR was performed using the forward and reverse primers (SEQ ID NOs:50 and 51) and plasmid pDC406-mCD40L as the template under the following conditions: hold 3 min at 94° C.; cycle 94° C. for 45 sec, 55° C. for 45 sec, 72° C. for 70 sec (30 cycles); hold 7 min at 72° C.; and hold at 4° C. This PCR resulted in a fragment "spacer+ΔCtΔTmCD40L," which was inserted into the plasmid pShuttle-CM V (Murphy et al. Prostate 38:73-8, 1999) after restriction endonuclease digestion with Xba I (TCTAGA) and Xho I (CTCGAG). This vector is designated pShuttle-sp-ΔCtΔTmCD40L(no signal sequence).

A vector was produced that was otherwise the same except that it encoded full length CD40L rather than the truncated form. This vector was made using a CD40 forward primer that annealed to the starting codons of murine CD40L. This vector is designated pShuttle-mCD40L (no signal sequence).

b) Construction of pShuttle-E7-sp-ΔCtΔTmCD40L(no signal sequence).

pShuttle-E7-ΔCtΔTmCD40L (no signal sequence) was prepared by inserting HPV-16 E7 upstream of the CD40 ligand sequence as follows: Sequence encoding the full-length HPV-16 E7 protein was obtained by PCR amplifying from the HPV viral genome using the following primers:

```
HPV 16 E 7 forward primer
                                        (SEQ ID NO: 52)
5'-ATTT GCGGCCGC TGTAATCATGCATGGAGA-3';

HPV E7 reverse primer
                                        (SEQ ID NO: 53)
5-CC CTCGAG TTATGGTTTCTGAGAACAGAT-3'.
```

PCR was performed using the above primers and the HPV 16 viral genome as template under the following conditions: hold 3 min at 94° C.; cycle 94° C. for 40 sec, 58° C. for 40 sec, 72° C. for 40 sec (30 cycles); hold 7 min at 72° C.; and hold at 4° C. The resulting amplicon was HPV 16 E7 encoding DNA with Not I and Xho I restriction sites at the 5' and 3' ends, respectively. The E7 DNA was inserted into the pShuttle-sp-ΔCtΔTmCD40L(no signal sequence) vector between the CMV promoter and directly 5' to the spacer of the spacer-ΔCtΔTmCD401, sequence using the Not I (GCGGCCGC) and Xho I (CTCGAG) restriction sites. The resulting plasmid is designated pShuttle-E7-ΔCtΔTmCD40L(no signal sequence).

c) Construction of pShuttle-HGH/E7-sp-ΔCtΔTmCD40L.

The pShuttle-E7-sp-ΔCtΔTmCD40L(no signal sequence) vector was used for insertion of the HGH signal sequence, upstream of E7 to generate HGHIE7-sp-ΔCtΔTmCD40L, described as follows.

DNA encoding the human growth hormone signal sequence MATGSRTSLLLAFGLECLPWLQEGSA (single letter amino acid code) (SEQ ID NO:54) was prepared by annealing phosphorylated oligonucleotides (SEQ ID NOs: 55 and 56) to generate the full 26 amino acid HGH sequence with Bgl II and Not1 overhangs.

Growth hormone signal upper strand (coding sequence in italics

```
                                        (SEQ ID NO: 55)
5'-GATCT CCACC ATG GCT ACA GGC TCC CGG ACG TCC CTG

CTC CTG GCT TTT GGC CTG CTC TGC CTG CCC TGG CTT

CAA GAG GGC AGT GCC GGC -3'.
```

Growth hormone signal lower strand:

```
                                        (SEQ ID NO: 56)
3'-A GGTGG TAC CGA TGT CCG AGG GCC TGC AGG GAC GAG

GAC CGA AAA CCG GAC GAG ACG GAC GGG ACC GAA GTT

CTC CCG TCA CGG CCGCCGG-5'.
```

Synthetic HGH signal sequence was prepared by annealing the above upper and lower strand oligos. The oligos were dissolved in 50 μl $H_2O$ (about 3 mg/ml). 1 μl from each oligo (upper and lower strand) was added to 48 μl annealing buffer (100 mM potassium acetate. 30 mM HEPES-KOH pH 7.4, and 2 mM Mg-acetate) incubated for 4 minutes at 95° C., 10 minutes at 70° C. and slowly cooled to about 4° C. The annealed DNA was phosphorylated using T4 PNK (polynucleotide kinase) under standard conditions.

The HGH signal sequence with Bgl II and Not I overhangs was inserted via Bgl II and Not I into pShuttle-E7-sp-66 CtΔTmCD40L(no signal sequence) to yield pShuttle-HGH/E7-sp-ΔCtΔTmCD40L. Thus, the transcription unit HGH/E7-sp-ΔCtΔTmCD40L encodes the HGH secretory signal followed by the fill length HPV type 16 E7 followed by a 10 amino acid linker with (LENDAQAPKS; SEQ ID NO:48) followed by murine CD40 ligand residues 52-260.

d) Construction of pShuttle-K/E7-sp-ΔCtΔTmCD40L

A transcription unit that included DNA encoding the signal sequence of the mouse IgG kappa chain gene upstream of DNA encoding the fill length HPV type 16 E7 protein ("K/E7") was generated by PCR using HPV16 plasmid and the following primers:

```
(primer 1)
                                        (SEQ ID NO: 57)
5'-ACG ATG GAG ACA GAC ACA CTC CTG CTA TGG GTA CTG

CTG-3';

(primer 2)
                                        (SEQ ID NO: 58)
5'-TC CTG CTA TGG GTA CTG CTG CTC TGG GTT CCA GGT

TC-3';

(primer 3)
                                        (SEQ ID NO: 59)
5'-TG CTC TGG GTT CCA GGT TCC ACT GGT GAC ATG CAT

G-3';
```

-continued (primer 4)

(SEQ ID NO: 60)

5'-TGG GTT CCA GGT TCC ACT GGT GAC ATG CAT GGA G

AT ACA CCT AC-3';

and (primer 5)

(SEQ ID NO: 61)

5'-CCG CTC GAG TGG TTT CTG AGA ACA GAT GGG GCA

C-3.'.

K/E7 with the upstream kappa signal sequence was generated by four rounds of PCR amplification (1st round: primers 4+5; 2nd round: add primer 3; 3rd round: add primer 2; 4th round: add primer 1). The K/E7 encoding DNA was cloned into the pcDNA™ 3.1 TOPO vector (Invitrogen, San Diego, Calif.) forming pcDNA-K/E7.

A DNA fragment that contained coding sequence for the 10 aa spacer upstream of mouse CD40 ligand from which the transmembrane and cytoplasmic domain had been deleted (-sp-ΔCtΔTmCD40L) was generated from a mouse CD40 ligand cDNA plasmid, pDC406-mCD40L (American Type Culture Collection), using the following PCR primers:

(SEQ ID NO: 62)

5'-CCG CTCGAG *AAC GAC GCA CAA GCA CCA AAA AGC* AAG

GTC GAA GAG GAA GTA AAC CTT C-3';

and (SEQ ID NO: 63)

5'-CGCGCCGCGCGCTAG *TCTAGA* GAGTTTGAGTAAGCCAAAAGAT-GAG-3'

(high fidelity PCR kit, Roche).

Fragment sp-ΔCtΔTmCD40L was digested with Xba I and XhoI restriction endonucleases and then ligated into pcDNA-KIE7. The K/E7-sp-ΔCtΔTmCD40L fragment was cut from the pcDNA vector and inserted into the pShuttle plasmid using Hind III and Xba I sites (pShuttle K/E7-sp-ΔCtΔTmCD40L). Thus, the K/E7-sp-ΔCtΔTmCD40L fragment includes the kappa chain secretory signal followed by the full length HPV type 16 E7 followed by a 10 amino acid linker (LENDAQAPKS; SEQ ID NO:48) followed by murine CD40 ligand residues 52-260.

e) Construction of pShuttle-HGH/E7-CD40L.

Adenoviral vector encoding a fusion protein with E7 upstream of full length mouse CD40L (with no intervening linker) was made using primers to amplify full length mouse CD40L using PCR. The following primers were used:

forward primer:

(SEQ ID NO: 64)

5'-GAGAC CTCGAG CAGTCA GC ATGATAGA AACATACAGC

CAACCTTCCC-3';

-continued reverse primer:

(SEQ ID NO: 65)

5'-CGCGCCGCGCGC CCC TCTAGA TCA GAG TTT GAG TAA GCC

AAA AGA TGA G-3'.

Amplified DNA was initially subcloned into the pcDNA3-K/E7 vector with Xba I and XhoI restriction endonucleases. The full length CD40L gene or ΔCtΔTmCD40L was directionally cloned into the pShuttle plasmid with the Hind III and Xba I sites.

f) Construction of pShuttle-HGH/E7-sp-ΔCtΔTmCD40L (human).

A vector encoding an E7/human CD40 ligand fusion protein (pShuttle-HGH/E7-sp-ΔCtΔTmCD40L(human)) is described as follows. Primers for amplifying human ΔCtΔTMCD40L+ spacer using a human CD40 ligand cDNA template are set forth below.

Human ΔCtΔTmCD40L+ spacer forward primer (HCD40LSPF) (CD40L sequence italicized):

(SEQ ID NO: 66)

5'-CCGCTC GAG AAC GAC GCA CAA GCA CCA AAA TCA *GTG TAT CTT*

*CAT AGA AGG TTG GAC*-3';

Human CD40L reverse primer (HCD40LR)

(SEQ ID NO: 67)

5'-CCC TCTAGA TCAGAGTTTGAGTAAGCCAAAGGAC-3'.

PCR is performed using the above primers and the plasmid pDC406-hCD40L as template under the following conditions: hold 3 min at 94° C.; cycle 94° C. for 45 sec, 52° C. for 45 sec, 72° C. for 70 sec (30 cycles); hold 7 min at 72° C.; and hold at 4° C. This amplification results in the "-sp-ΔCtΔTmCD40L(human)" fragment, which encodes 44-261 of human CD40L and an amino terminal 10 aa spacer. The forward primer HCD40LSPF encodes a 10 residue spacer (LENDAQAPKS; single letter code; SEQ ID NO:48) to be located between the tumor antigen and the CD40 ligand (hCD40L) of the transcription unit. The "sp-ΔCtΔTmCD40L(human)" fragment is then inserted into the plasmid pShuttle-CMV (Murphy G P, el at Prostate 38: 73-78 (1999)) after restriction endonuclease digestion with Xba I (AAGCTT) and Xho I (CTCGAG). This vector is designated pShuttle-sp-ΔCtΔTmCD40L(human)(no signal sequence). Modification of pShuttle-sp-ΔCtΔTmCD40L(human)(no signal sequence) to include the HPV-16 E7 upstream of the human CD40 ligand sequence is accomplished essentially as described above for the murine CD40 ligand encoding vectors. The resulting plasmid is designated pShuttle-E7-sp-ΔCtΔTmCD40L(human)(no signal sequence) and is used for insertion of the HGH signal sequence upstream of E7 to generate HGH/E7-sp-ΔCtΔTmCD40L(human). Thus, the transcription unit HGH/E7-sp-ΔCtΔTmCD40L(human) encodes the HGH secretory signal, followed by the full length HPV type 16 E7, followed by a 10 amino acid linker (LENDAQAPKS; SEQ ID NO:48) followed by human CD40 ligand representing residues 44-261.

h) Recombinant Adenovirus

The recombinant adenoviral vectors were generated using the AdEasy vector system (Strategene, San Diego, Calif.). Briefly, the resulting plasmids pShuttle-HGH/E7-sp-ΔCtΔTmCD40L, pShuttle-FIGH/CD40L, pShuttle-HGH/

E7-CD40L, and pShuttle-HGH/E7 were linearized by Pme I digestion and then co-transformed into *E. coli* strain BJ5183 together with pAdEasy-1. Recombinants were selected with kanamycin and screened by restriction enzyme analysis. The recombinant adenoviral construct was then cleaved with Pac I, and transfected into 293A cells to produce viral particles. The titer of recombinant adenovirus was decided by the tissue culture infectious dose 50 ($TCID_{50}$) method.

4. Purification of Recombinant E7/ecdCD40L Protein in Bacterial System and E7 Assay Methods a) Purification of Recombinant E7/ecdCD40L Protein The E7/ecdCD40L fusion cDNAs were inserted into the expression vector pTri by XcmI and NotI sites. The expression bacterial cell line Rosetta (DE3) was transfected by pTri E7/ecdCD40L vectors and induced by IPTG for 3 hours at 37° C. The bacterial pallets were harvested and purified by His Selected Nickel Affinity Gel (Sigma).

b) Flow Cytometry Analysis of T Regulatory Cells

To quantify T regulatory cells, the CD4 T cells from lymph node, spleen or tumor nodule were respectively stained by two different kinds of markers, CD4CD25 and CD4FOXP3, with FITC- or PE-conjugated anti-mouse monoclonal antibodies (Pharmingen, eBiscience) for 30 min on ice, prior to immunostaining with labeled antibodies. The T cells were first incubated with a Fc-γ blocking antibody (anti-mouse CD16/CD32 antibody) to avoid the nonspecific binding of mAbs to Fc-γ receptors. The cells were then washed twice, fixed in 4% paraformaldehyde, and analyzed using a Becton Dickinson flow cytometer (FACS Calipur).

c) Tetramer Staining

PE-labeled H-2Db tetramer containing HPV16 E7 49-57 peptide (RAHYNIVIT) (SEQ ID NO: 68) was purchased from Beckman Coulter and used for the analysis of peptide specific CTL immunity. Ten days after immunization, 1×106 erythrocyte-depleted spleen cells were stained by 10 ul of tetramer together with 1/100 diluted fluorescein isothiocyanate (FITC)-anti mouse CD8a (clone53-6.7, BD Pharmingen) in 100 ul PBS supplemented with 3% FCS, incubated at room temperature for 30 minutes, and then washed with 3 ml of PBS. Following centrifugation, the cell pellet was resuspended in 500 ul of PBS/0.5% paraformaldehyde for FACS analysis. Tetramer positive and CD8+ cells are shown as a percentage of total spleen cells.

d) Cytokine Profile by ELISPOT Assays

The presence of E7-specific effector T cells in the immunized mice was also assessed by carrying out ELISPOT assays, as described previously. Briefly, splenocytes obtained from mice vaccinated with each of the different vectors were-restimulated in vitro by culture with the TC-1 cell line (responder-to-stimulator ratio=25/1) in the presence of 10 U/ml IL-2 for 48 hours. Re-stimulated splenocytes were then plated in 96-well nitrocellulose filter plates ($5\times10^4$ cells in 100 microliters). The wells were pre-coated with rat anti-mouse anti-IFN-antibody or anti-IL-4 antibody. After incubation for 24 hours at 37° C./5% $CO_2$, the plates were then washed with PBS, and the presence of cytokine-producing spleen cells was detected by incubation at 4° C. with biotinylated goat anti-rat secondary antibody, followed by 100 microliter/well of horseradish peroxidase avidin D. To this was added 150 microliter/well freshly prepared substrate buffer (0.4 mg/ml 3-amino-9-ethyl-carbazole in a total of 50 ml 0.05 mol/In sodium acetate buffer) and 20 microliter 30% $H_2O_2$. The stained spots corresponding to IFN producing cells or to 1L-4 producing cells, were enumerated under a dissecting microscope.

e) Cytotoxicity Assay

Mononuclear cells from the spleens of these mice were incubated with mitomycin C-treated TC-1 cells in RPMI 1640 medium, supplemented with 10% fetal bovine serum (FBS), 5 mM 2-mercaptoethanol, 2 mM glutamine, 1 mM pyruvate, and nonessential amino acids for 5 days. To perform the cytotoxicity assay, firstly TC-1 tumor cells/(target cells) were labeled with the red-fluorescent dye PKH26 (Sigma, St Louis, Mo.) according to the manufacturer's specifications. In brief, the target cells were washed in PBS then resuspended at $10^7$ cells/mi in solution. PKH26 dye was added to a final concentration of 2 μM, mixed and incubated at room temperature. After 5 min, the reaction was quenched with 3 volumes of FCS and the cells were washed an additional 3 times in RPMI/10%FCS medium then $5\times10^3$ labeled TC-1 cells were incubated with the stimulated splenic mononuclear cells (effector cells) at a different effector/target ratio for 4 hours at 37° C., in culture media containing 5% FBS. At the end of the incubation, mononuclear cell-mediated cytotoxicity was stained for intracellular Caspase-3 according to the manufacturer's protocol(BD PharMingen), double positive cells was determined by flow cytometry on live gated $PKE26^+$ cells.

f) In Vivo Efficacy Experiment in Mouse Model

Mice (5 or 10 per group) were challenged by subcutaneous injection of $5\times10^5$ TC-1 cells were injected subcutaneously. On the next day, the mice were vaccinated via SC injection with $1\times10^8$ PFU Ad-sig-E7/ecdCD40L. One week later, mice were boosted with the same adenoviral vector regimen as the first vaccination or followed by SC injections of the 10 ug recombinant E7/ecdCD40L protein every week. Tumor volumes were measured in centimeters by caliper. One month later, the tumor free mice were rechallenged by $1\times10^7$ TC-1 cells and the tumor volume was calculated as tumor volume=length×(width$^2$)/2 (this assumes an ellipitical shape).

g) Statistics

All parameters were analyzed using Student's t test, or ANOVA followed by Scheffé's procedure for multiple comparisons as post-hoc analysis; all data shown is presented as mean ±S.E. of the mean (S.E.).

5. Inducing Immunity Against a Viral Antigens in Young (Two Month Old) Mice with Ad-sig-E7JecdCD40L Vector.

Two sc injections (seven days apart), each 10 μg/mouse of the Ad-sig-E7/ecdCD40L adenoviral vector were given to six week old C57BLI6J mice which were evaluated for induction of resistance to engraftment of the E7 positive TC-1 cells (see PNAS 2003 100:15101-15106; Blood 2004 104:2704-2713). Injected mice were challenged with 500,000 E7 positive TC-1 cells and 500,000 E7 negative EL-4 cells implanted subcutaneously (at a different site than the adenoviral vector injection site) seven days following the last vaccination injection. The growth of E7 negative EL-4 cells (measured by tumor volume) was not suppressed in the Ad-sig-E7lecdCD40L injected mice, while E7-positive syngeneic TC-1 cell growth was completely suppressed in injected mice. FIG. 6. These results indicate that the Ad-sig-E7/ecdCD40L vector induces a specific immune response directed to the E7 viral antigen in young 2 month old animals.

Figure 7:
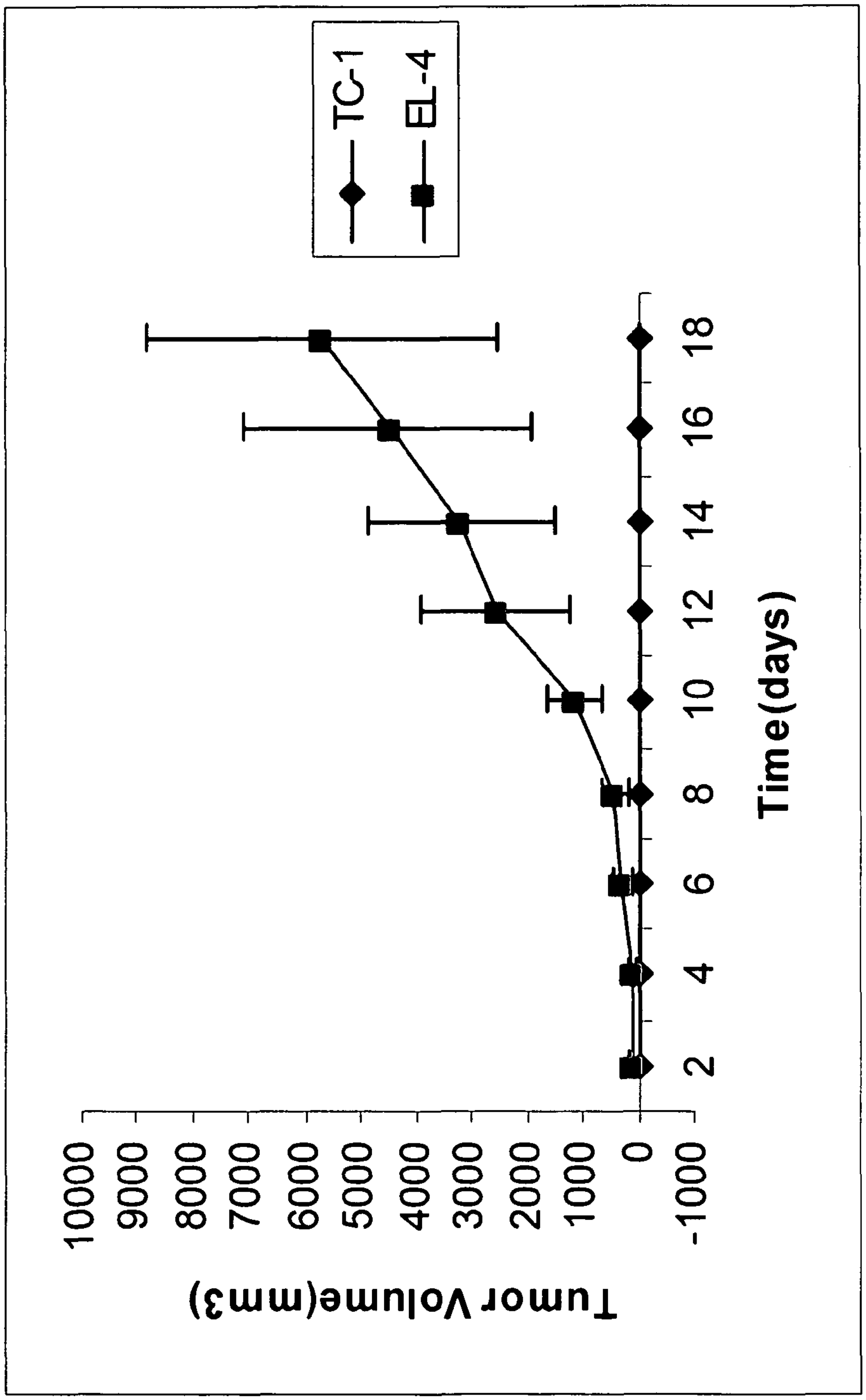
FIG. 7 depicts growth of E7-positive TC-1 cells versus E7-negative EL-4 cells in mice injected with splenic T lymphocytes from donor mice vaccinated with Ad-sig-E7/ecdCD40L vector.

6. Ad-sig-E7/ecdCD40L Vector Induced Immunity in Young (Two Month Old) Mice is CD8 Dependent To test if the Ad-sig-E7/ecdCD40L vector injections in 2 month old mice induced immunological memory cells, splenic T lymphocytes were collected from C57BL/6J mice which had survived for a full year after vaccination with the Ad-sig-E7/ecdCD40L vector and challenge with the E7 positive TC-1 cells. The test C57BL/6 nude mice (n=7) were injected sc with 500,000 TC-1 cells and then injected intraperitoneally five days later with $10\times10^6$ splenic lymphocytes from mice which had been vaccinated with the Ad-sig-E7/ecdCD40L vector one year earlier. As shown in FIG. 7, only transient growth of the TC-1 cells (solid diamonds) occurred in the C57BL/6 nu/nu mice which had received intraperitoneal injections of the T cells from the Ad-sig-E7/ecdCD40L vaccinated mice (♦). In contrast, the TC-1 cells grew well (line defined by the solid squares (■)) in control C57BL/6 nu/nu mice which were injected intraperitoneally with $10\times10^6$ splenic T cells from unsensitized donor C57BL/6 mice five days after injection of TC-1 cells. These results show that the immunity induced by the vector injections involves memory cells.

Figure 8:
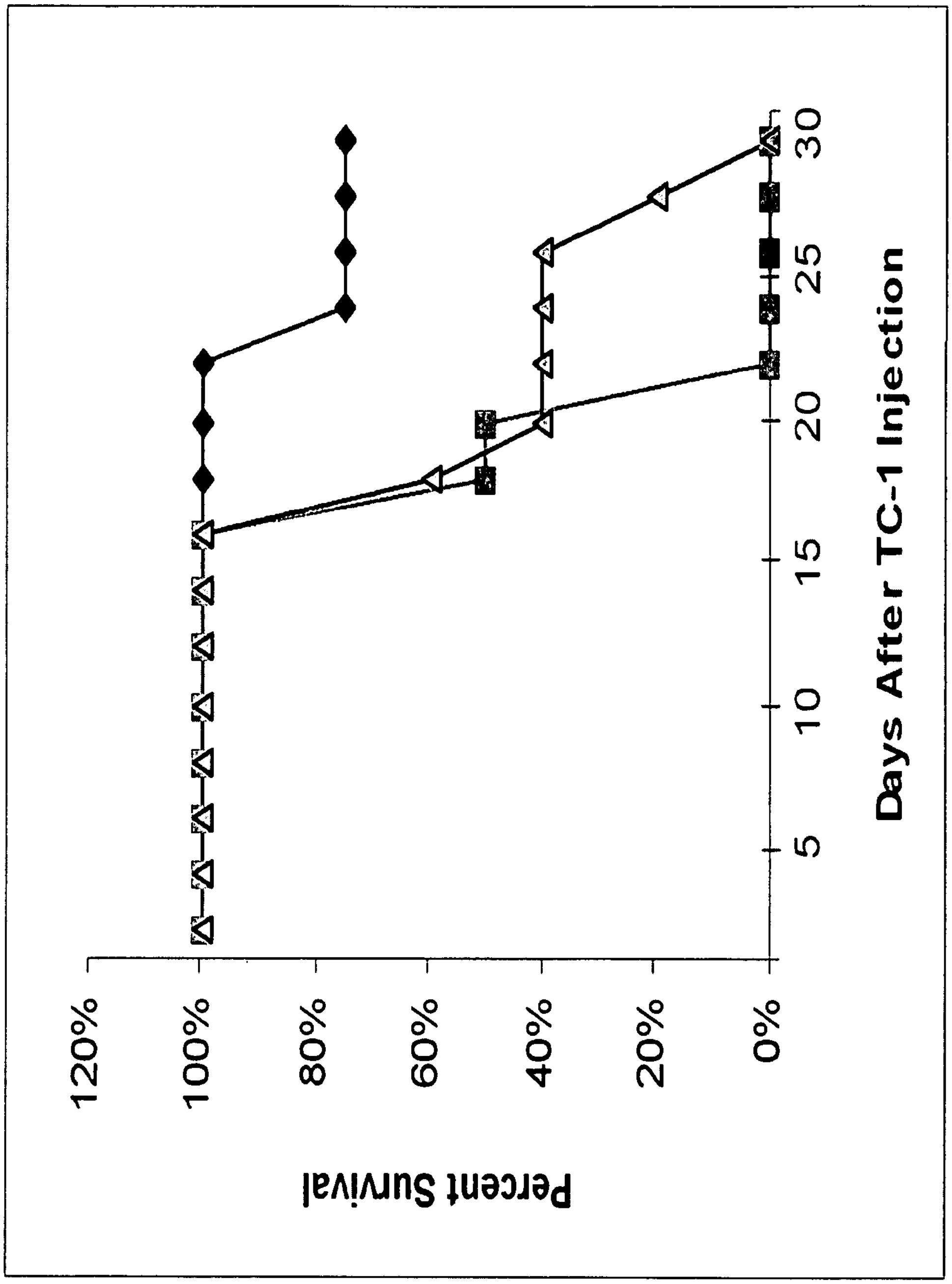
FIG. 8 depicts percent survival days after injection of test mice. The test mice were first injected with CD8+ cells (black diamonds), CD4 cells (triangles) or no cells (squares) from Ad-sig-E7/ecdCD40L vector vaccinated mice. Seven days later the test mice were injected with E7-positive Tc-1 cells.

To test whether this immune resistance was dependent on CD8+ or CD4+ T cell lymphocytes, donor immunocompetent C57BL/6 mice were injected sc with the Ad-sig-E7/ecdCD40L vector at days zero and seven. Seven days later (day 14), the mice were injected se with 100,000 E7 positive TC-1 cells. As shown below in FIG. 8, the C57BL/6 donor mice were treated in vivo with antibodies which were cytolytic and specific for CD4 (solid diamonds) or CD8 (solid triangles) positive cells to deplete the respective T cell population 5, 3, and 1 days prior to the vector injection, and every six days after the sc injection of the Ad-sig-E7/ecdCD40L vector, and also on days 6, 7, 8, 10, 12, and 14 days following the injection of the TC-1 cells. Then the sensitized CD8+ T cells from the CD4 depleted vaccinated mice (see solid diamonds in FIG. 8) or CD4+ T cell lymphocytes from the CD8 depleted vaccinated mice (see solid triangles in FIG. 8) from sensitized C57BL/6 donors were injected intraperitoneally into C57BL nude mice 7 days after subcutaneous injection of $1\times10^5$ TC-1 cells. A third group of C57BL/6 nude mice, which were control mice, did not receive passive transfer of T cells (see solid squares in FIG. 8) 7 days following subcutaneous injection of TC-1 cells. The C57BL/6 nu/nu mice injected with CD8+T cells from the Ad-sig-E7/ecdCD40L injected donor animals survived statistically significantly longer than did the other groups, Thus, the induction of immunity to TAA positive tumor cells by the injection of the Ad-sig-TAA/ecdCD40L vector was dependent on CD8+ T cell lymphocytes and not dependent on CD4 cells. This vaccine is therefore useful for circumventing the CD4 defects in old people for influenza vaccines.

7. Ad-sig-E7/ecdCD40L Vector Increases E7 Viral Antigen Specific Cytotoxic T Lymphocytes in Young (Two Month Old) Mice Spleen cells were isolated from C57Bl/6 mice (from Harlan) before and 7 days after two injections with $1\times10^8$PFU of the Ad-sig-E7lecdCD40L vector. The level of the E7-specific T cells was determined by tetramer assay as described above.

Figure 9:
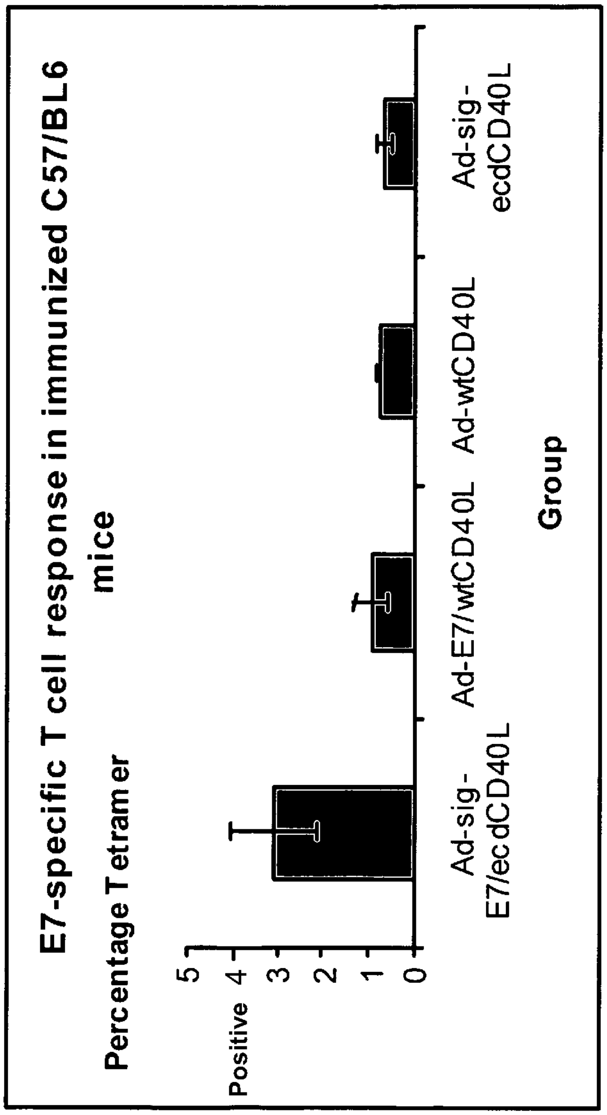
FIG. 9 depicts the level of E7-specific T cell response after injection of different vector constructs.

T cells increased three fold in the spleen following the Ad-sig-E7/ecdCD40L vector injection, whereas no significant increases occurred with the other control vectors (Ad-E7/wtCD40L; ad-wtCD40L, Ad-sig-ecdCD40L) including the Ad-E7/wtCD40L, in which the E7/CD40L protein was not secretable from the infected cells. FIG. 9.

8. Ad-sig-E7/ecdCD40L Vector Induces Viral Antigen Immunity in Old (18 Month Old) Mice The ability to elicit viral antigen immunity in old (18 month old) mice using The Ad-sig-E7/ecdCD40L vector was evaluated. The Ad-sig-E7/ecdCD40L vector was injected once sc with $1\times10^8$ IU. At days 7, 14 and 21 after the vector injection, an sc injection of the E7/ecdCD40L protein (10 micrograms/injection) was given as a booster. Seven days later, mice were sacrificed and the level of E7 specific T cells in the spleen determined by ELISPOT assay.

Figure 10:
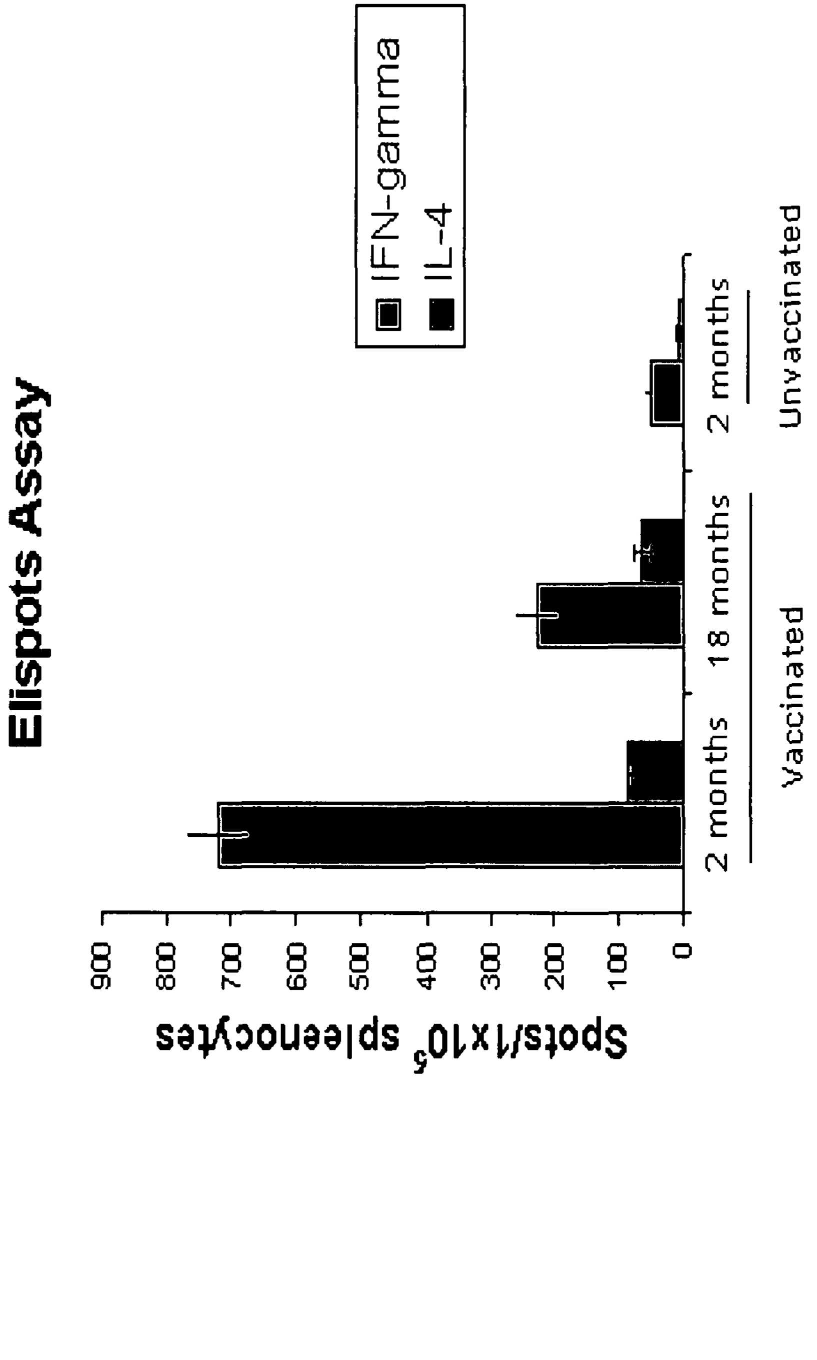
FIG. 10 shows the levels of splenocytes producing interferon-gamma and IL4 in Ad-sig-E7lecdCD40L vector vaccinated and unvaccinated young and old mice.

The levels of interferon-gamma positive cells/100,000 splenocytes was increased to 225 in the old mice and 725 in young mice, while IL-4 cell numbers increased to over 100 antigen specific T cells/100,000 splenocytes. FIG. 10 Although the magnitude of the induction of antigen specific T cells in the 18 month old mice was less than that seen in the 2 month old mice, the absolute magnitude of the response in the 18 month old mice is in the range induced by most other vaccines in young mice and is clearly sufficient to produce'a robust immune response.

Figure 11:
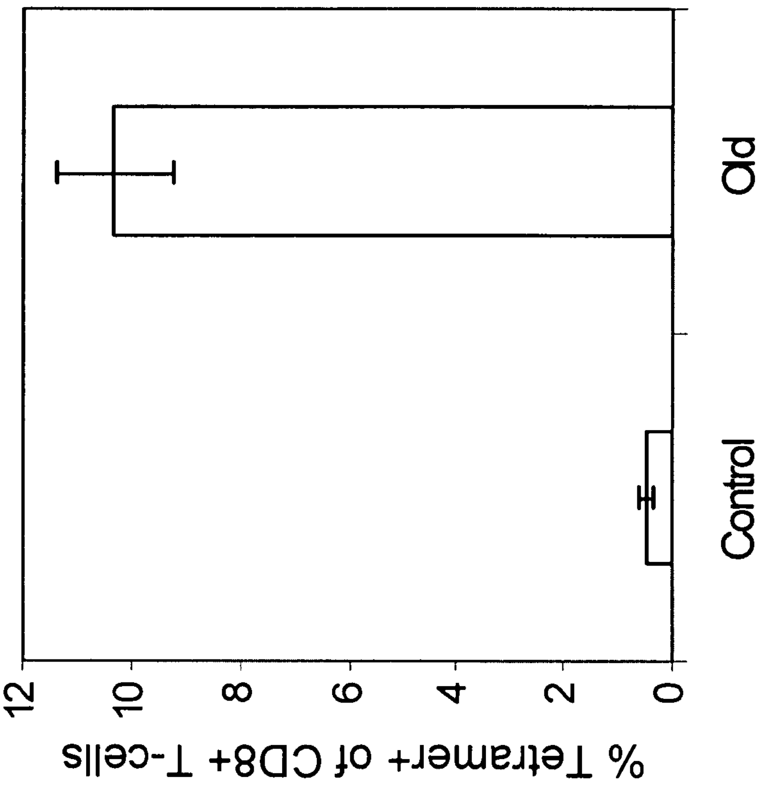
FIG. 11 shows the percentage of antigen specific T cells in the CD8 population antigen positive tumor of old animals unimmunized (control) and immunized with Ad-sig-E7/ecdCD40L vector.

The increase in the percentage of antigen specific T cells to total CD8 T cells in the tumor tissue in old mice was measured via E7 tetramers before and after vaccination. The Ad-sig-E7/ecdCD40L vaccine induced the level of antigen specific T cells in the tumor tissue by 10 fold (FIG. 11).

Figure 12:
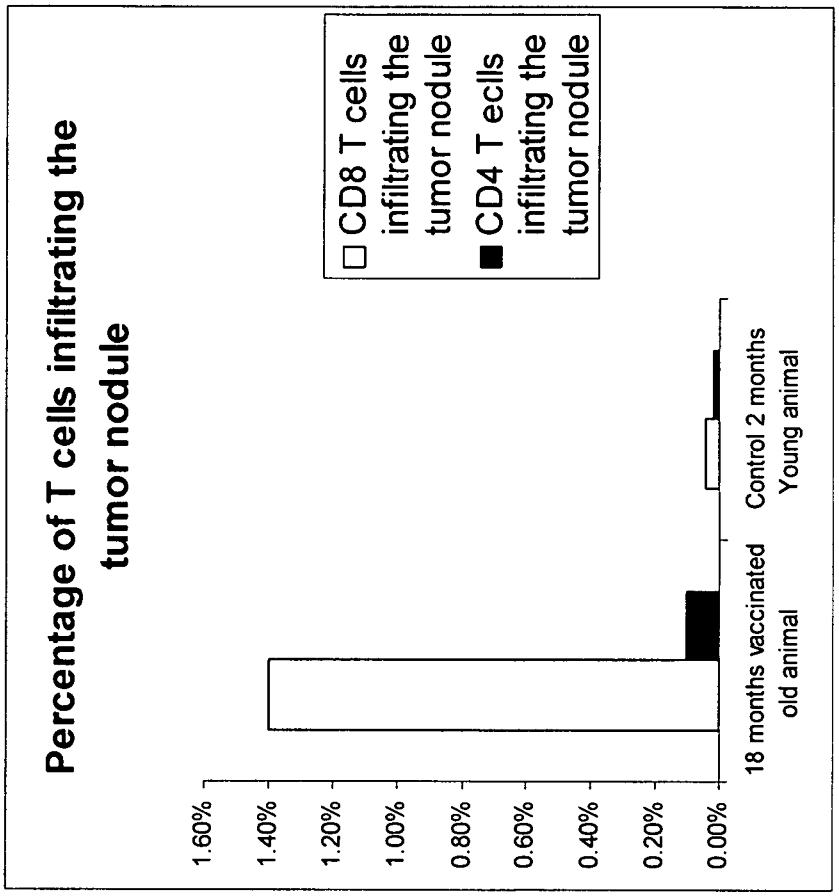
FIG. 12 shows the percentage of CD4 and CD8 T cells infiltrating tumor nodules in old animals vaccinated with Ad-sig-E7/ecdCD40L vector and in young animals unvaccinated.

The increase in the number of T cells as a percentage of the total number of cells in the tumor tissue following vaccination in the old mice was also measured. The increase of the percentage of T cells increased over 10 fold after the vaccination in the old mice (FIG. 12).

Figure 13:
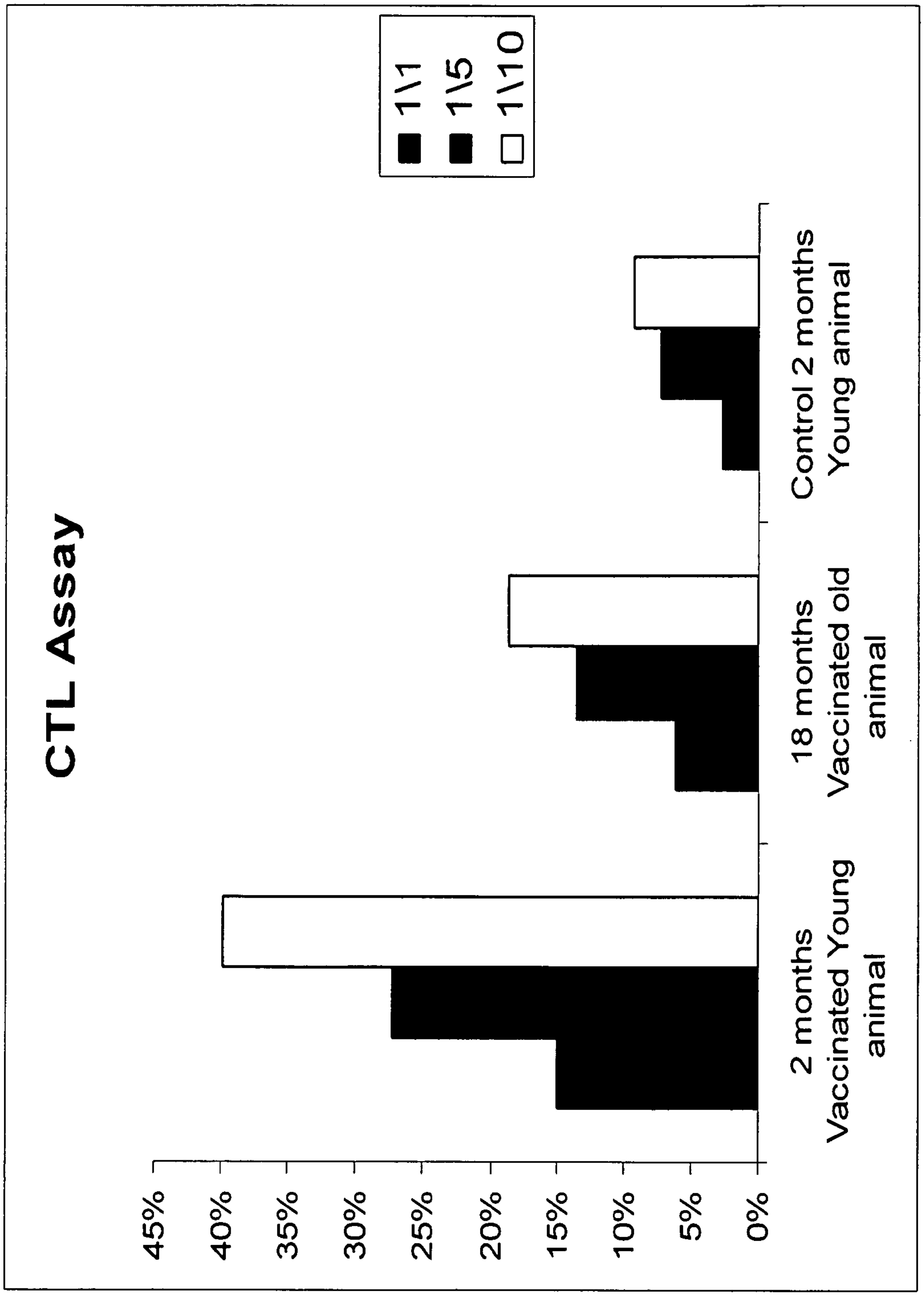
FIG. 13 depicts cytotoxic T cell activity at various effector to target ratios induced by Ad-sig-E7/ecdCD40L vector vaccination of young and old mice.

The level of increase of antigen specific cytotoxic T lymphocytes ("CTLs") induced by vaccination in 2 month and 18 month old mice was also evaluated using the protein boost immunization scheme. Increases in antigen specific CTLs following vaccination in the old as well as the young animals is shown in FIG. 13. Again, the level of the increase of the CTLs seen in the 18 month old mice was less than that seen in the 2 month old mice, but the absolute magnitude of the induction was impressive in the 18 month old mice.

9. Immune Response Induced by the V, VP, VPP, and VPPP Vaccination Regimens with the Ad-sig-E7/ecdC40L Vector Prime in 2 Month Old ("Young") Mice.

Figure 27:
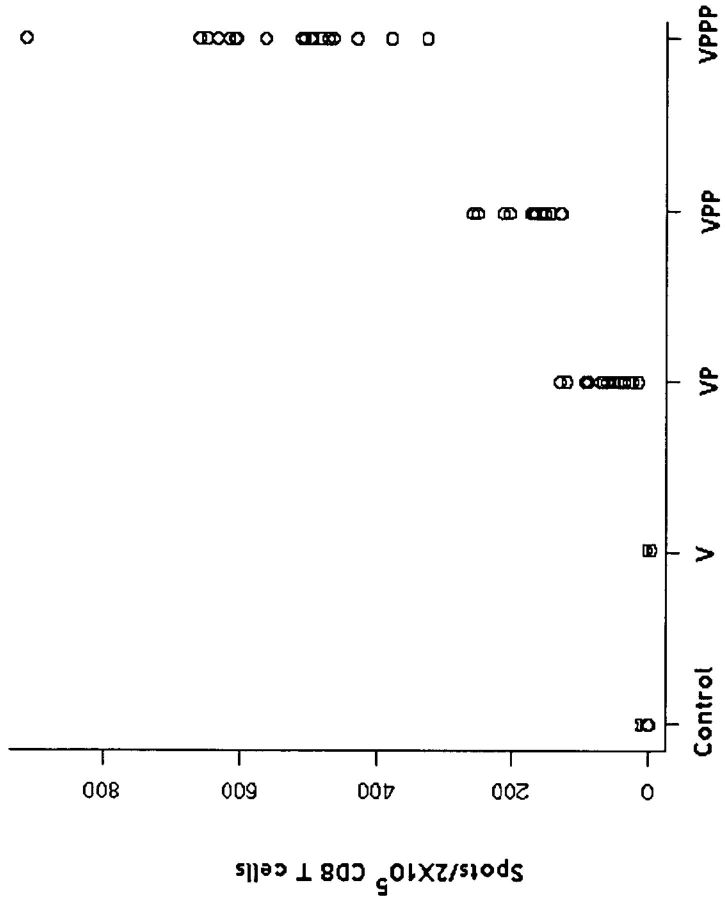
FIG. 27 depicts the level of E7-specific CD8 T cells in a preparation of splenocytes from 2 month old mice ("Young") vaccinated according to the V, VP, VPP, or VPPP vaccination regimens wherein "V" means to administer the Ad-sig-E7/ecdC40L and "P" means to administer the E7/ecdCD40L protein.
Figure 28:
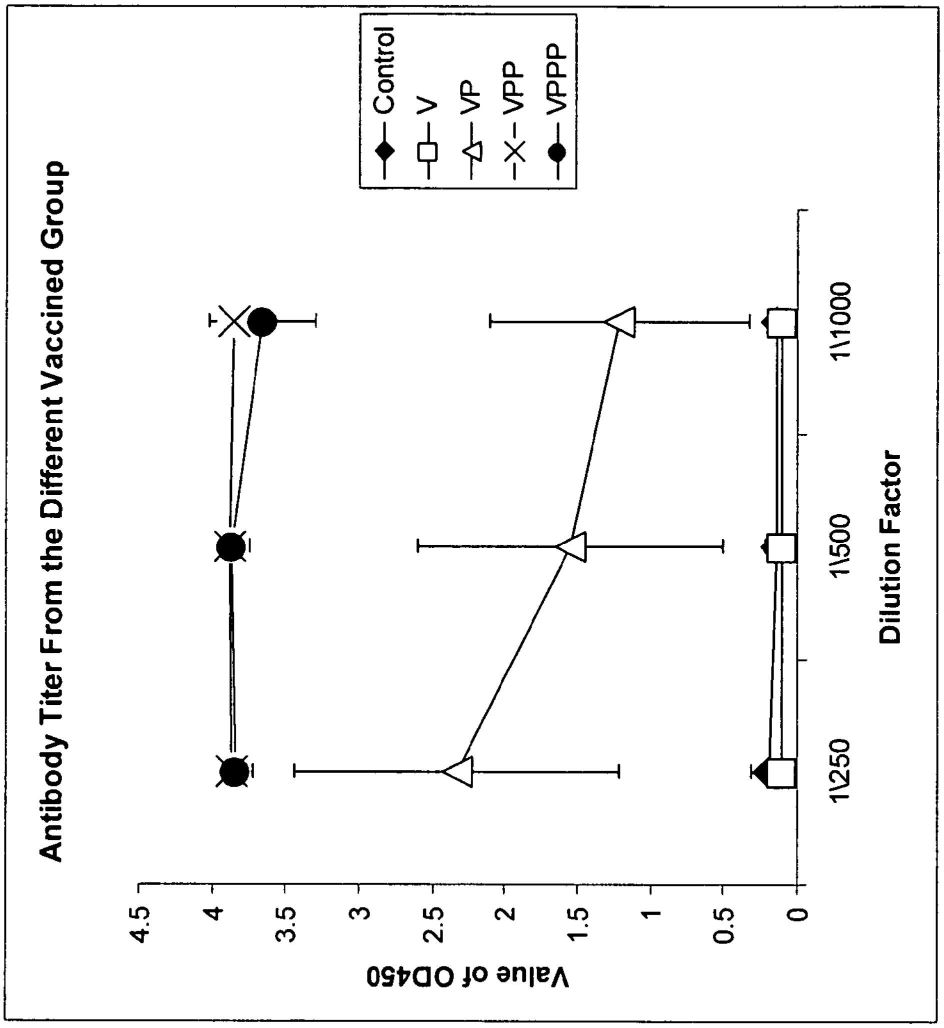
FIG. 28 depicts the level of E7-specific antibody in serum from 2 month old mice vaccinated according to the V, VP, VPP, or VPPP vaccination regimens wherein "V" means to administer the Ad-sig-E7/ecdC40L and "P" means to administer the E7/ecdCD40L protein.

Two month old C57BL6 mice were vaccinated using one of the following four vaccination regimens: a single subcutaneous injection of Ad-sig-E7/ecdCD40L ("V"), or a single subcutaneous vector injection followed by one boost with fusion protein ("VP"), two boosts with fusion protein ("VPP"), or three boosts with fusion protein ("VPPP"), in which each boost is a weekly subcutaneous injections of the E7/ecdCD40L fusion protein. The levels of E7-specific splenic CD8 T cells and E7-specific antibody levels in serum were determined. As shown in FIG. 27, the levels of the E7-specific splenic CD8 T cells of the vaccinated mice increased going from V to VP to VPP and to VPPP. VP, VPP and VPPP are significantly different from each other ($p<0.05$). As shown in FIG. 28, the levels of the E7 specific serum antibodies against the E7 B cell epitope ElDGPAGQAEPDRAHYNIVTFCCI(CD of the vaccinated mice increased significantly with the number of fusion protein boosts after the initial vector injection (VP<VPP<VPPP). At a dilution factor of 1/1000, the difference of the serum antibody levels in the vaccinated versus the unvaccinated control group was statistically significant for VP mice ($p=0.004$); VPP mice($p<0.001$); and VPPP mice($p<0.0001$).

10. Immune Response Induced by the V, VP, VPP, and VPPP Vaccination Regimens with the Ad-sig-E7/ecdC40L Vector Prime in 18 Month Old ("Old") Mice.

Figure 29:
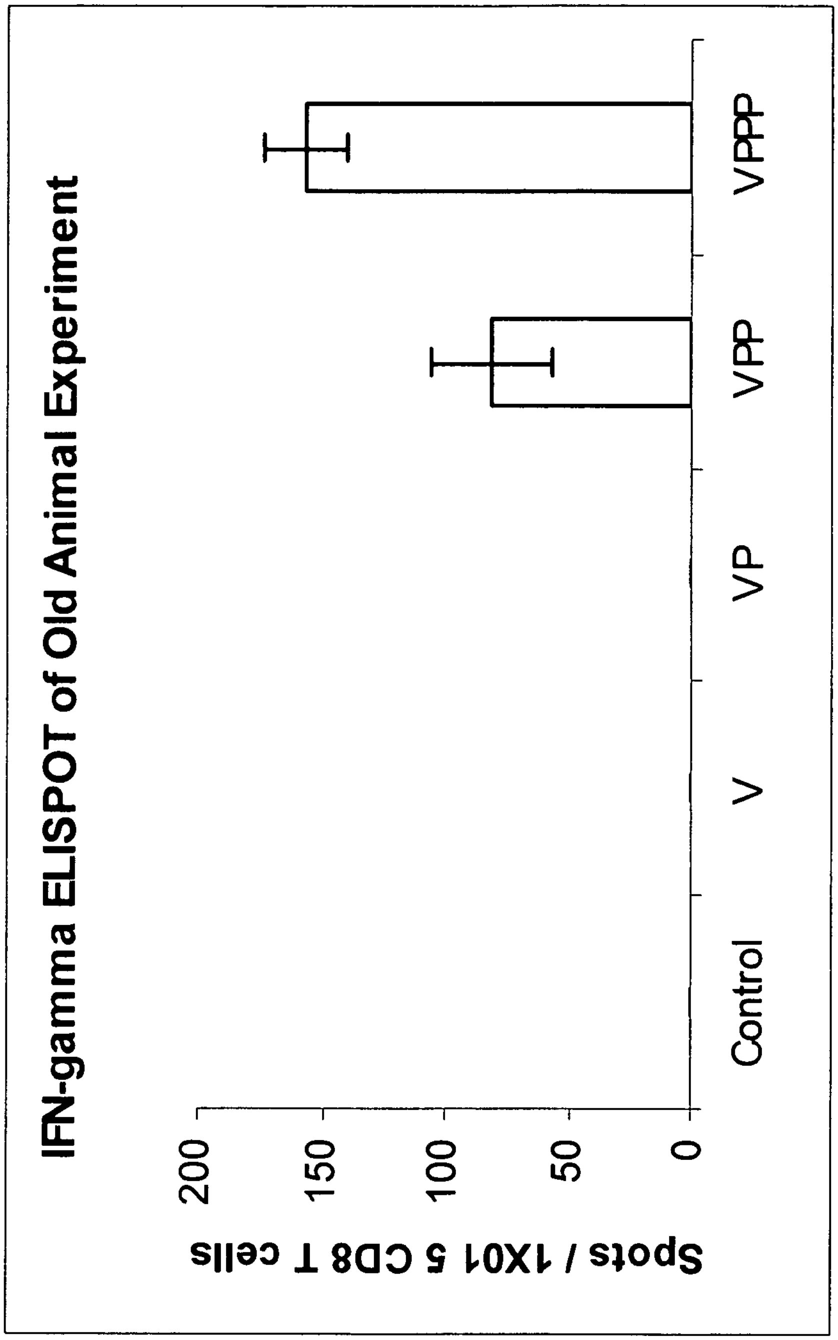
FIG. 29 depicts the level of E7-specific CD8 T cells in a preparation of splenocytes from 18 month old mice ("Old") vaccinated according to the V, VP, VPP, or VPPP vaccination regimens wherein "V" means to administer the Ad-sig-E7/ecdC40L and "P" means to administer the E7/ecdCD40L protein.
Figure 30:
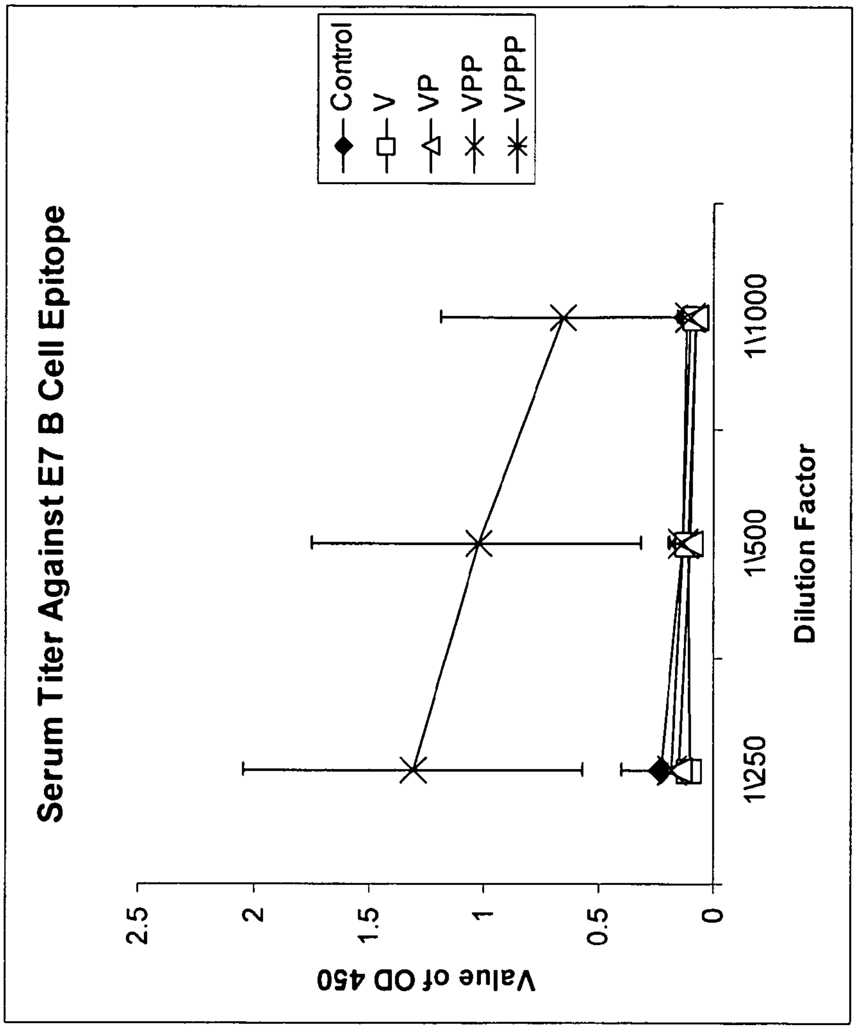
FIG. 30 depicts the level of E7-specific antibody in serum from 18 month old mice ("Old") vaccinated according to the V, VP, VPP, or VPPP vaccination regimens wherein "V" means to administer the Ad-sig-E7/ecdC40L and "P" means to administer the E7/ecdCD40L protein.
Figure 31:
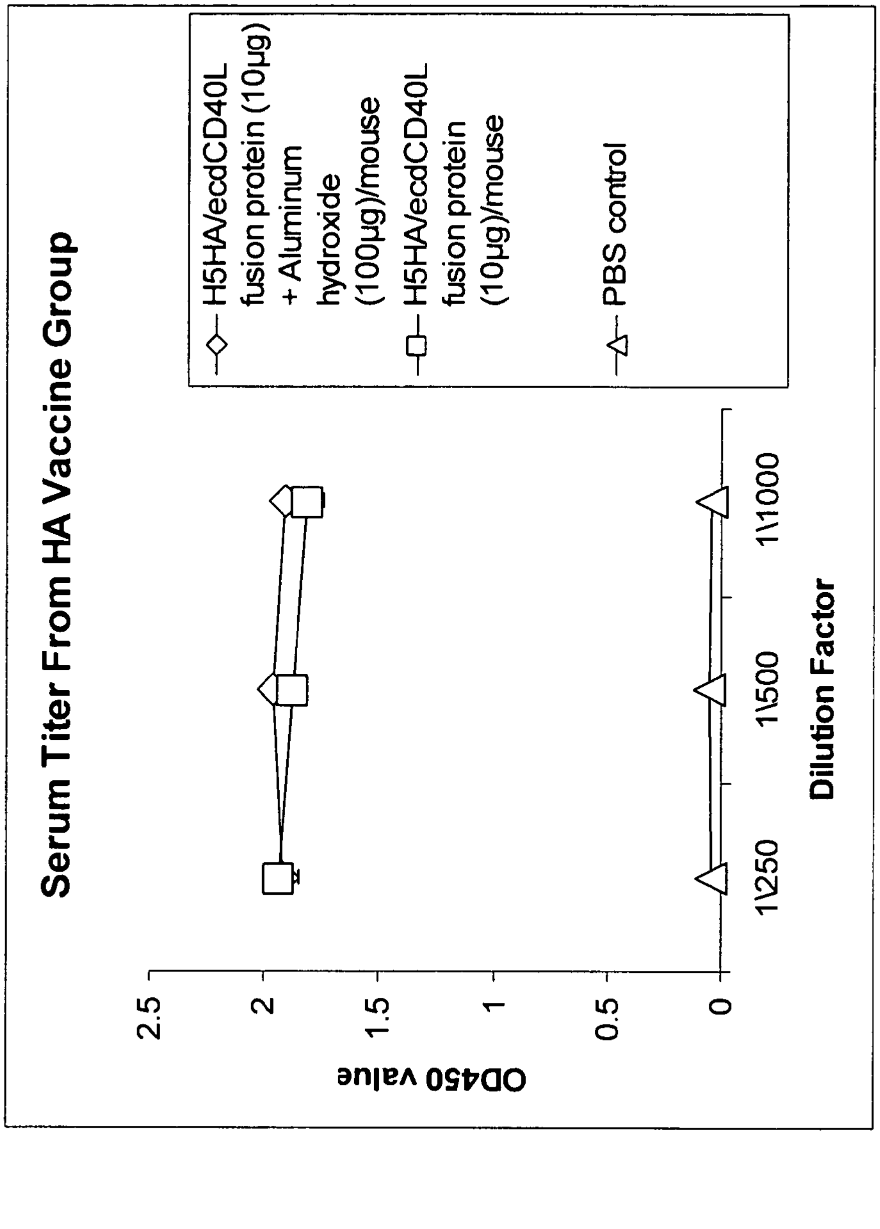
FIG. 31 demonstrates the presence of antibodies against HA in serum of mice following a vaccination by three administrations of HA/ecdCD40L fusion protein.
Figure 32:
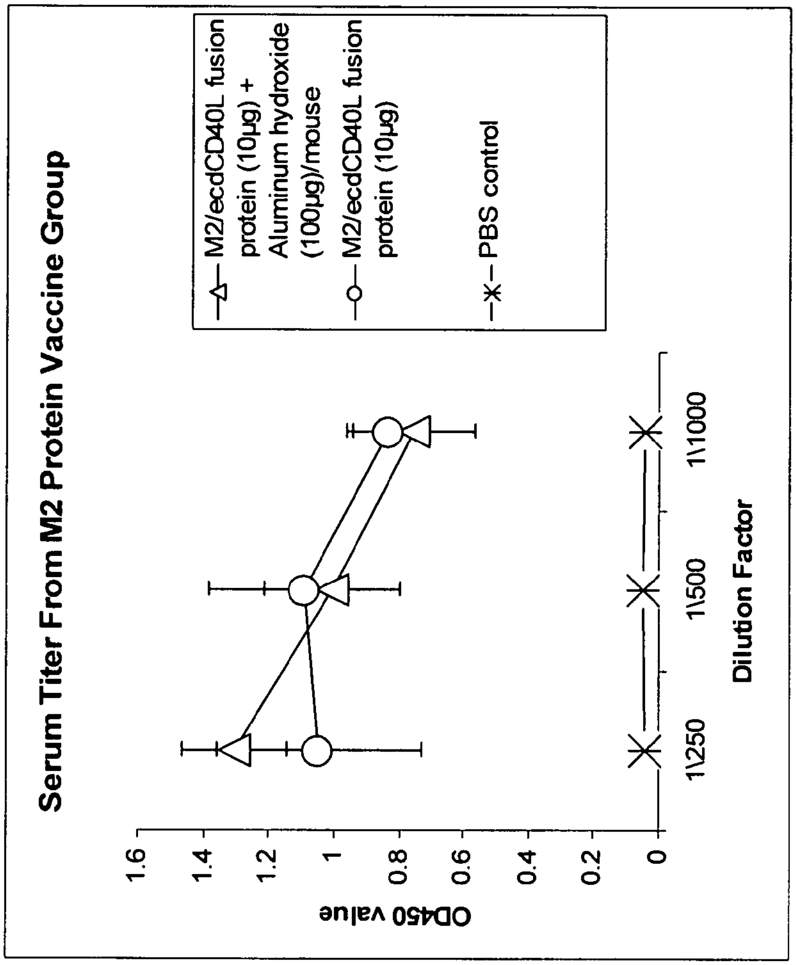
FIG. 32 demonstrates the presence of antibodies against M2 in serum of mice following vaccination by three administrations of M2/ecdCD40L fusion protein.

18 month old C57BL6 mice were vaccinated using one of the following four vaccination regimens: a single subcutaneous injection of Ad-sig-E7/ecdCD40L (V), or a single subcutaneous vector injection followed by one (VP), two (VPP) or three (VPPP) weekly subcutaneous injections of the E7/ecdCD40L protein boost. The levels of E7-specific splenic CD8 T cells and E7-specific antibody levels in serum were determined. As shown in FIG. 29, increases in the levels of the E7-specific splenic CDR T cells of the vaccinated mice were detectable only at the VPP and VPPP level. As shown in FIG. 30, the levels of the E7-specific serum antibodies against the E7 B cell epitope EIDGPAGQAEPDRAHYNIVTFCCKCD of the vaccinated mice increased significantly only with three protein boost injections after the initial vector injection (VPPP).

Figure 14:
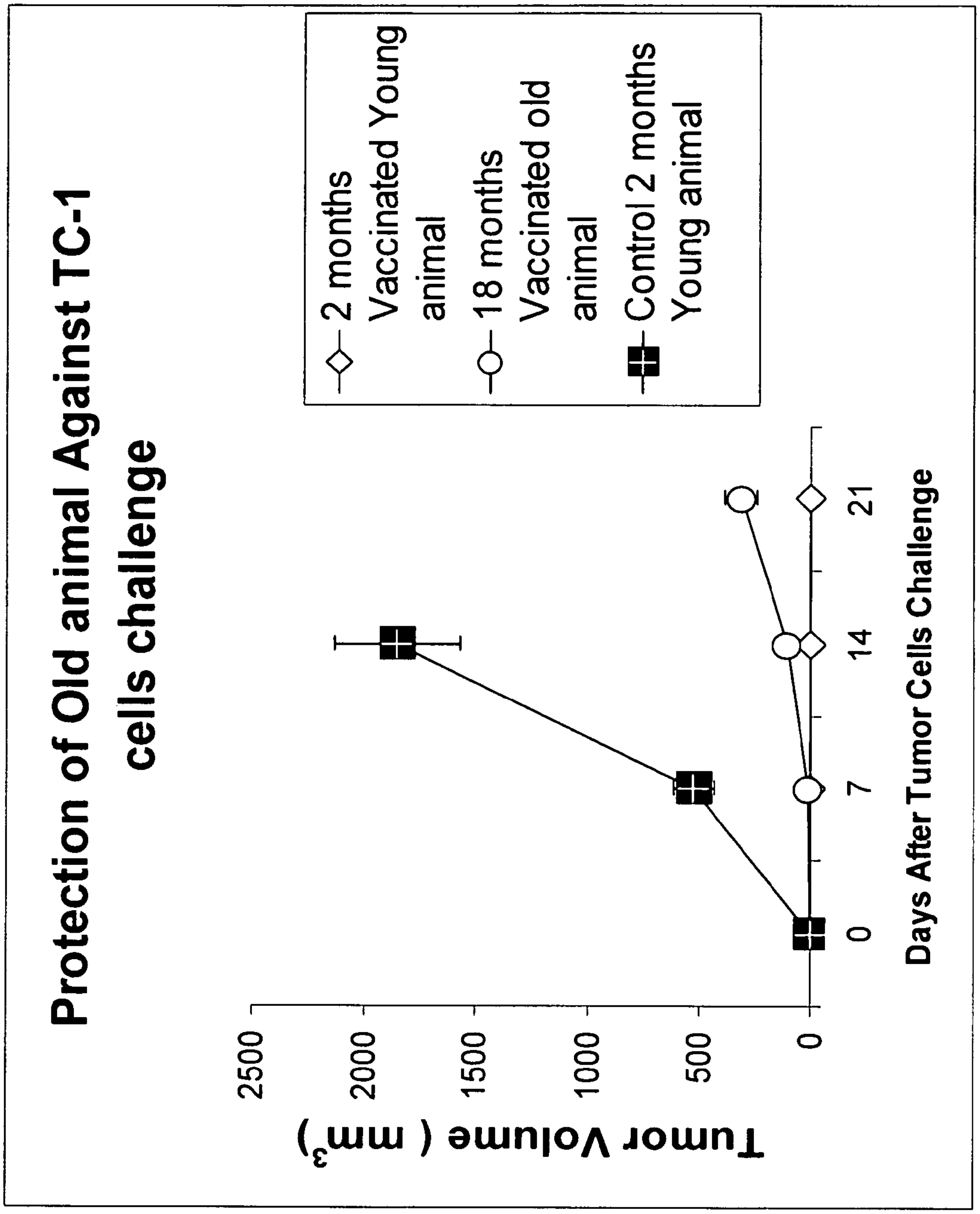
FIG. 14 depicts the suppression of E7 tumor growth in old and young Ad-sig-E7/ecdCD40L vector vaccinated mice.

11. Effect of the Ad-sig-TAA/ecdCD401, Vector Vaccine and Protein Boost Against Viral Antigen in Old (18 Month Old) Mice on Growth of Cells Positive for Viral Antigen The suppression of E7 positive tumor growth in 18 month old mice was almost equal to the level of suppression of the tumor growth in 2 month old mice with the vector vaccination alone. FIG. 14. The effect of the protein boosts on the induction of the immune response induced by the Ad-sig-E7/ecdCD40L vector was tested. Test C57B1/6J mice were injected first with $1\times10^8$ PFU Ad-sig-E7/ecdCD40I, vector followed by 3 protein boosts (10 μg protein per injection) given at 7, 14 and 21 days after the vector injection.

Figure 15:
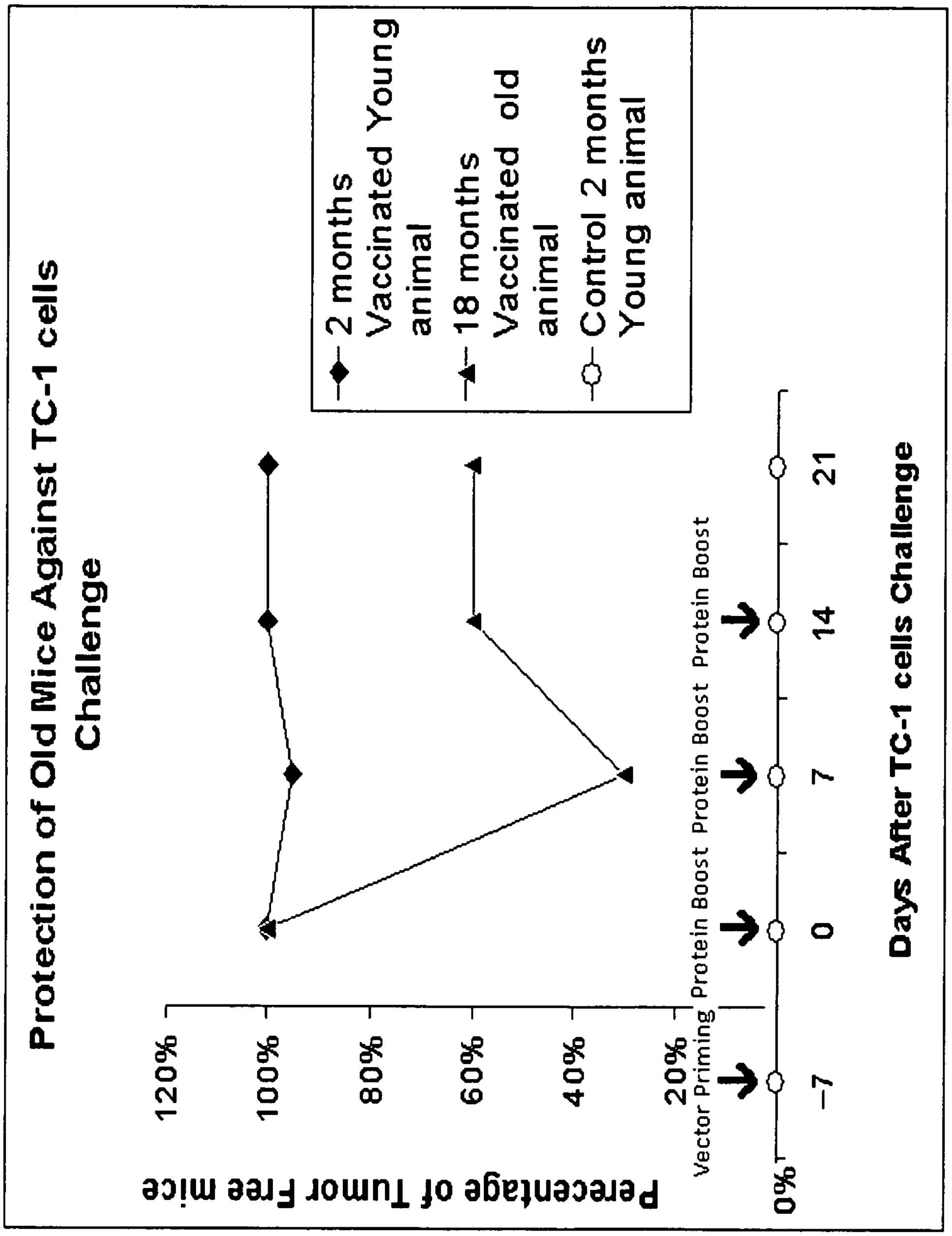
FIG. 15 depicts the percentage of E7 tumor free mice after vaccination with the Ad-sig-E7/ecdCD40L vector and protein boost in old and young mice.

The endpoint of these studies was in vivo suppression of the E7 tumor growth in C57Bl/6J mice, as measured by the percentage of mice which remained tumor free. As shown in FIG. 15, the sc injection of the E7/ecdCD40L protein induced regressions of existing tumor and converted tumor positive mice to tumor negative mice. These data suggested that Ad-sig-TAA/ecdCD40L by se vector and protein boost could induce complete regressions in existing tumor which was progressive in 18 month old mice.

Figure 16:
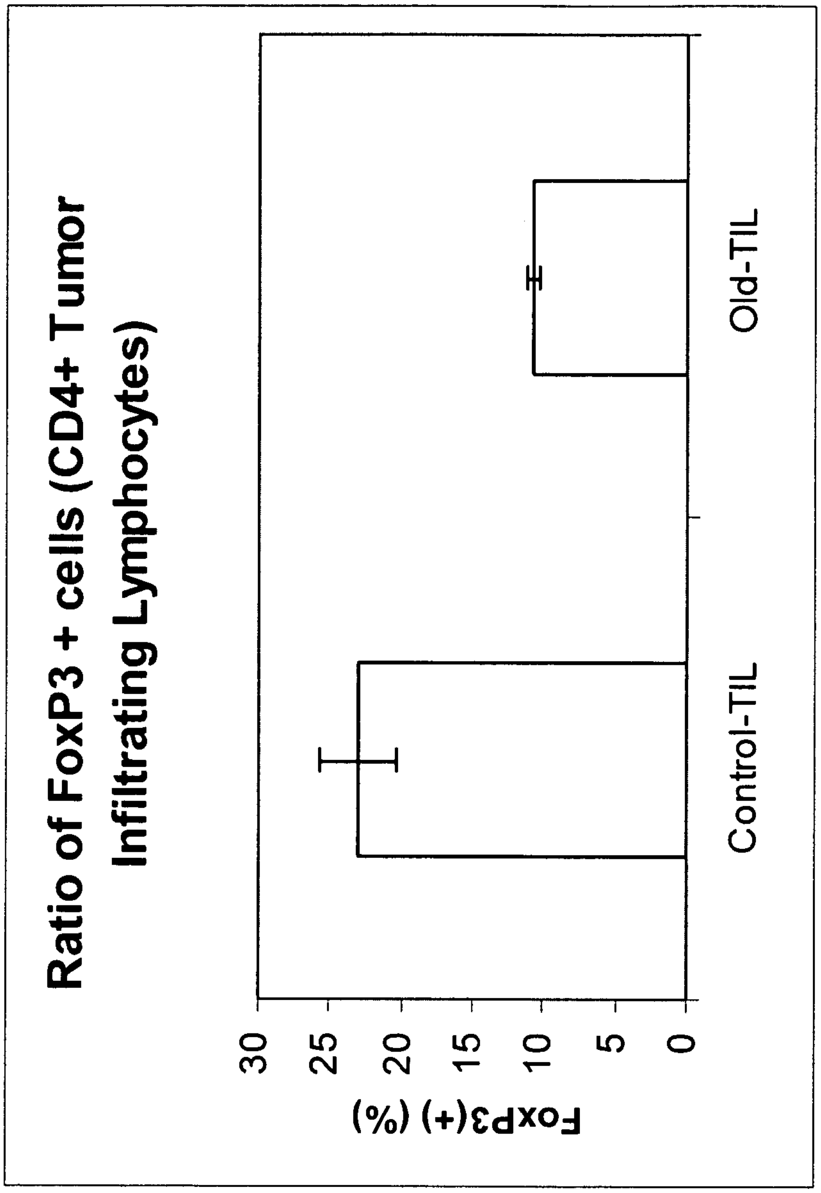
FIG. 16 shows the percentage of FoxP3 regulatory CD4+ cells among tumor infiltrating lymphocytes in the tumor before (control) and after vaccination (old) of old (18 month) mice with Ad-sig-E7/ecdCD40L vector.

12. Effect of the Ad-sig-TAA/ecdCD40L Vector Vaccination in Old Mice on the Levels of CD4 FOXP3 Negative Regulatory T Cells in Tumor Tissue Increases CD4 FOXP3 negative regulatory T cells have been reported to limit the degree to which vaccines suppress the degree of immune response to vaccination. Decreases in the level of FOXP3 negative regulatory CD4 T cells have been reported with vaccination. Therefore the level of FOXP3 CD4 T cells in the tumor tissue before and after $1\times10^8$ PFU Ad-sig-E7/ecdCD40L vector (including the protein boosting) was measured by FACS analysis. As shown in FIG. 16, vaccination in old animals decreased the CD4 FOXP3 negative regulatory T cells in the tumor tissue by 2 fold.

Figure 17:
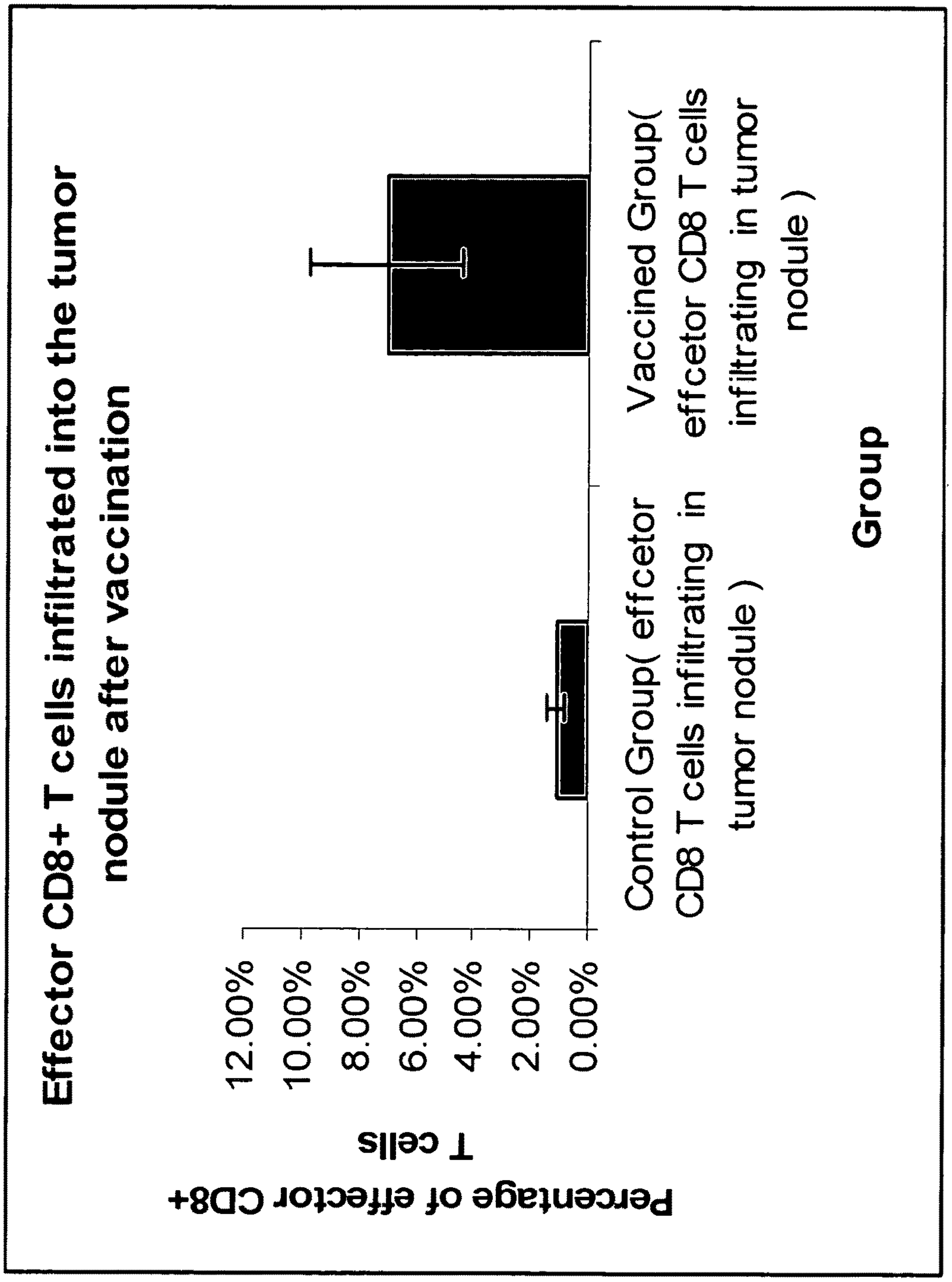
FIG. 17 shows the percentage of effector CD8+ cells in tumor nodules of rH2n.Tg (i.e., HER2 transgenic) mice injected with Ad-sig-rH2N/ecdΔCtΔTmCD40L vector.

13. Levels of CD8 Effector and CD4 Negative Regulatory T Cells in Tumor Tissue Following Ad-sig-rH2N/ecdCD40L Vector Vaccination in Young (2 Month Old) Mice The levels of antigen specific CD8 effector T cells in tumor tissue was determined after vaccination with the Ad-sig-rH2N/ecdCD40L vector, the preparation of which is described in U.S. Patent Application Publication US 2005-0226888 (application Ser. No. 11/009,533) titled “Methods for Generating Immunity to Antigen,” filed Dec. 10, 2004. Subcutaneous tumor nodules of rH2N.Tg mice were minced before and after two sc injections of the Ad-sig-rH2N/ecdCD40L vector. $1\times10^8$PFU vector were administered per injection; injections were given 7 days apart, and tumor nodules were isolated 10 days after the last injection. Single cell suspensions were generated from the tumor tissue after mincing, treated with 0.03% DNAse and then 0.14% collagenase I, and filtered through Nylon mesh. The number of effector T cells isolated from the tumor tissue after vaccination (CD8+, CD44+, LY6C+ and CD62L−) was increased roughly 5-7 fold. FIG. 17. This data suggests that the suppression of the growth of the rH2N positive tumor cells in the rH2N.Tg mice following Ad-sig-rH2N/ecdCD40L vaccination is mediated in part by the trafficking of rH2N specific CD8 effector T cells into the tumor tissue.

RNA was isolated from the tumor infiltrating CD8 effector T cells and the pattern of gene expression was compared before and after vaccination using the Affymetrix gene expression system. The expression level of the 21 known chemokine receptors and ligands in the effector T cells which were infiltrating the tumor tissue was also examined. The levels of the CCL3 (2.8 fold increase) and the CCR5 (16 fold increase), which are involved in the targeting of I cells to the extravascular sites of tissue inflammation, were increased in the rH2N specific CD8 effector T cells in the tumor tissue. The chemokine pathway plays a major role in the trafficking of effector and memory T cells from the lymph nodes draining sites of vaccination or infection to the tissue sites harboring inflammation or infection (Current Opinion 2003 15:343-348; Cell Adhesion and Communication 1998 6:105-110).

14. Induction of Immunity with the Ad-sig-H5N1HA/ecdCD40L Vector Against the Hemagglutinin Protein of the H5N1 Avian Influenza Virus in 2 Month Old Mice and 18 Month Old Mice A portion of the HA sequence from an H5N1 influenza virus was used as an antigen in the Ad-sig-TAA-ecdCD40L vector, creating an Ad-sig-H5 HA-ecdCD40L expression vector. As described below, this vector induced an immune response in mice; a significant increase in the level of H5 HA specific CD8 T cells was detected.

a) Construction of the Ad-sig-H5HA-ecdCD40L Expression Vector i) H5HA-ecdCD40L(mouse)

DNA (SEQ ID NO: 69) encoding a portion of a receptor binding region corresponding to amino acid residues 135-175 connected to residues 230-250 (see FIG. 2, underlined) of the hemagglutinin (HA) protein of the H5N1 avian influenza strain (H5HA), first isolated in 1997 in Hong Kong from a child with a fatal respiratory illness (see, e.g., Science 1998 279:393-96; J. Virology 1998 73: 2094-98; Emerging Infectious Disease 2002.8(8):1-12) is shown below.

```
                                          (SEQ ID NO: 69)
5'AAAAGTTCTTGGTCCAATCATGATGCCTCATCAGGGGTGAGCTCAGCA

TGTCCATACCTTGGGAGGTCCTCCTTTTTCAGAAATGTGGTATGGCTTAT

CAAAAAGAACAGTGCATACCCAACAGCTACTAGACCCAAAGTAAACGGGC

AAAGTGGAAGAATGGAGTTCTTCTGGACAATTTTAAAG-3'.
```

The above HA construct was generated using the following two primers:

```
forward primer:
                                          (SEQ ID NO: 70)
5'AAAAGTTCTTGGTCCAATCATGATGCCTCATCAGGGGTGAGCTCAGC

ATGTCCATACCTTGGGAGGTCCTCCTTTTTCAGAAATGTGGTATGGCTT

ATCAAAAAGAACAGTGC-3'
and

reverse primer:
                                          (SEQ ID NO: 71)
5'CTTTAAAATTGTCCAGAAGAACTCCATTCTTCCACTTTGCCCGTTTAC

TTTGGGTCTAGTAGCTGTTGGGTATGCACTGTTCTTTTTGATAAGCCAT

ACCAC-3'.
```

Double-stranded nucleic acid encoding e HA region was generated as follows. The oligos were dissolved in 50 μl $H_2O$ (about 3 mg/ml), 1 μl from each oligo (forward and reverse primers) was added to 48 μl annealing buffer plus 7 μL $ddH_2O$ (100 m M Tris-HCl , 1M NaCl, 10 mM EDTA) incubated for 4 minutes at 95° C., 10 minutes at 70° C. and slowly cooled to about 4° C.

A transcription unit that included DNA encoding the signal sequence of the mouse IgG kappa chain gene upstream of DNA encoding the Avian HA antigen epitope was generated by PCR using the double-stranded HA generated in the previous paragraph and the following primers:

(SEQ ID NO: 72)
5'-CCACC ATG GAG ACA GAC ACA *CTC CTG CTA TGG GTA CTG CTG*-3';

(SEQ ID NO: 73)
5'-TC CTG CTA TGG GTA CTG CTG CTC *TGG GTT CCA GGT TC*-3';

(SEQ ID NO: 74)
5'-TG CTC TGG GTT CCA *GGT TCC ACT GGT GAC ATG CAT G*-3';

(SEQ ID NO: 75)
5'-TGG GTT CCA GGT TCC ACT GGT GAC ATG AAAAGTTCTTGGTCCAATCATGATGC-3';
and (SEQ ID NO: 76)
5'-CCG CTCGAG GCTTTAAAATTGTCCAGAAGAACTCC-3'.

K/Avian FluHA (i.e., kappa signal-H5 fragment) was generated by four rounds of PCR amplification (1st round: primers 4 +5; 2nd round: add primer 3; 3rd round: add primer 2; 4th round: add primer 1), under the following conditions: hold 3 min at 94° C.; cycle 94° C. for 30 sec, 55° C. for 30 sec, 72° C. for 30 sec (30 cycles); hold 7 min at 72° C.; and hold at 4° C. The KIAvian FIuHA encoding DNA was cloned into the pcDNA™ 3.1 TOPO vector (Invitrogen, San Diego, Calif.) forming pcDNA-K/Avian FluHA.

Primers for amplifying mouse ΔCtΔTmCD40L+ spacer using a mouse CD40 ligand cDNA template are set forth below.

Mouse ΔCtΔTmCD40L+ spacer forward primer (MCD40LSPF):

(SEQ ID NO: 50)
5'-CCG CTCGAG *AAC GAC GCA CAA GCA CCA AAA TCA* AAG GTCGAAGAGGAAGTAAAC-3';

Mouse CD40L reverse primer (MCD40LR):

(SEQ ID NO: 51)
5'-CCC TCTAGA ATCAGAGTTTCACTAAGCCAA-3'.

These primers will amplify a ΔCtΔTmCD40L+spacer which encodes 52-260 of mouse CD40L. The forward primer MCD40LSPF encodes a 10 residue spacer (LENDAQAPKS) (SEQ ID NO:48) to be located between the antigen and the CD40 ligand (MCD40L) of the transcription unit. PCR was performed using the forward and reverse primers (SEQ ID NOs 50 and 51) and plasmid pDC406-mCD40L as the template under the following conditions: hold 3 min at 94° C.; cycle 94° C. for 45 sec, 55° C. for 45 sec, 72° C. for 70 sec (30 cycles); hold 7 min at 72° C.; and hold at 4° C. This PCR resulted in a fragment "spacer+ΔCtΔTmCD40L"which was subcloned into pcDNA3TOPO. The "spacer+ΔCtΔTmCD40L" fragment was then inserted into the plasmid pcDNA-sig-AfluHA after restriction endonuclease digestion with XbaI (TCTAGA) and Xho I (CTCGAG). The sig-AfluHA/ΔCtΔTmCD40L (mouse) encoding DNA was cut from the pCDNA3TOPO using HindIII-XbaI restriction and inserted into pShuttle-CMV (see Murphy et al., *Prostate* 38: 73-78, 1999) downstream of the CMV promoter. This vector is designated pShuttle sig-AfluHA/ΔCtΔTmCD40L(mouse). Thus, the transcription unit sig-AfluHA-ΔCtΔTmCD40L(mouse) encodes the kappa secretory signal followed by the extracellular domain of Avian flue HA followed by a 10 amino acid linker (LI NDAQAPKS; SEQ ID NO:48) followed by mouse CD40 ligand residues 52-260.

This amplified H5 HA sequence is cloned so that it is located between a secretory mouse Ig kappa sequence (sig) and a linker (sp), which linker connects to the gene encoding the ecdhCD40L (extracellular domain of the human CD40L) in an AdEasy shuttle vector. Vector and soluble fusion protein expressed therefrom will be prepared as described above.

ii) H5HA-ecdCD40L(human)

The construction of a vector encoding an HA/human CD40 ligand fusion protein (pShuttle-K/FIA-sp-ΔCtΔTmCD40L(human)) is described as follows. Primers for amplifying human ΔCtΔTMCD40L+ spacer using a human CD40 ligand cDNA template are set forth below.

Human ΔCtΔTmCD40L+ spacer forward primer (HCD40LSPF) (CD40L sequence italicized):

(SEQ ID NO: 66)
5'-CCGCTC GAG AAC GAC GCA CAA GCA CCA AAA TCA *GTG TAT CTT CAT AGA AGG TTG GAC*-3';

Human CD40L reverse primer (HCD40LR)

(SEQ ID NO: 67)
5'-CCC TCTAGA TCAGAGTTTGAGTAAGCCAAAGGAC-3'.

PCR is performed using the above primers and the plasmid pDC406-hCD40L as template under the following conditions: hold 3 min at 94° C.; cycle 94° C. for 45 sec, 52° C. for 45 sec, 72° C. for 70 sec (30 cycles); hold 7 min at 72° C.; and hold at 4° C. This amplification results in the "-sp-ΔCtΔTmCD40L(human)" fragment, which encodes 44-261 of human CD40L and an amino terminal 10 aa spacer. The forward primer HCD40LSPF encodes a 10 residue spacer (LENDAQAPKS; single letter code; SEQ ID NO:48) to be located between the tumor antigen and the CD40 ligand (hCD40L) of the transcription unit. The "sp-ΔCtΔTmCD40L(human)" fragment is subcloned into pcDNA3TOPO. The "spacer+ΔCtΔTmCD40L(human)" fragment is then inserted into the plasmid pcDNA-sig-AfluHA after restriction endonuclease digestion with XbaI (TCTAGA) and Xho I (CTCGAG). The sig-AfluHA/ΔCtΔTmCD40L(human) encoding DNA is cut from the pCDNA3TOPO using KpnI-XbaI restriction and inserted into pShuttle-CMV (see Murphy et al., *Prostate* 38: 73-78, 1999) downstream of the CMV promoter. This vector is designated pShuttle sig-AfluHA/ΔCtΔTmCD40L(human). Thus, the transcription unit sig-AfluHA-ΔCtΔTmCD40L (human) encodes the kappa secretory signal followed by the extracellular domain of Avian flue HA followed by a 10 amino acid linker (LENDAQAPKS; SEQ ID NO:48) followed by human CD40 ligand residues 44-261.

This amplified H5 HA sequence is cloned so that it is located between a secretory mouse Ig kappa sequence (sig) and a linker (sp), which linker connects to the gene encoding the ecdhCD40L (extracellular domain of the human CD40L) in an AdEasy shuttle vector. Recombinant adenoviral vectors were generated using the AdEasy vector system (Stratagene, San Diego, Calif.) as described above, resulting in the Ad-K/HA/ecdCD40L vector. Fusion protein were prepared as described below.

b) Induction of Immunity in Mice

Figure 18:
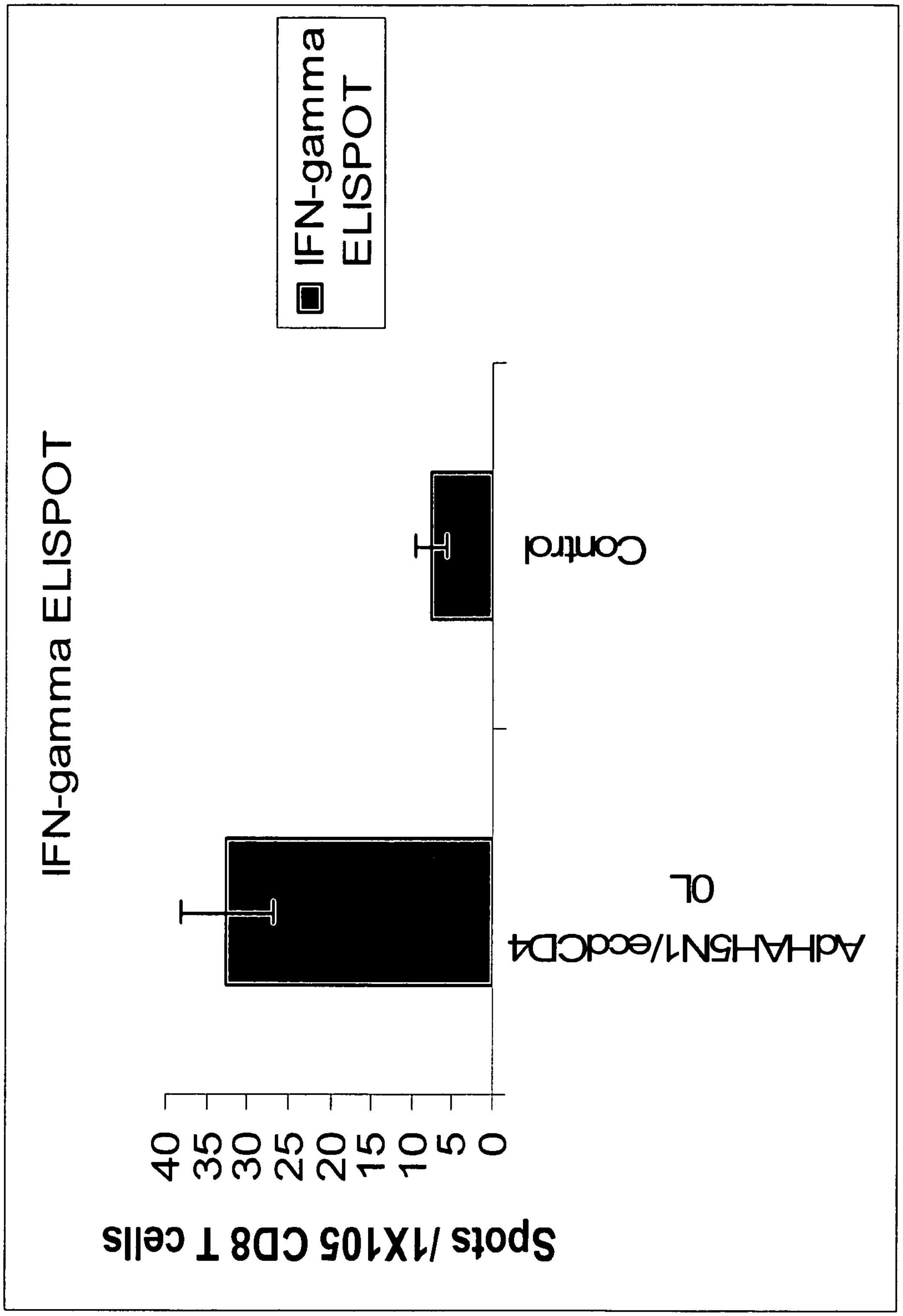
FIG. 18 depicts the level of H5HA-specific CD8 T cells in the spleen of Ad-sig-H5HA/ecdCD40L vaccinated mice compared to unvaccinated mice via ELISA spot assay interferon gamma detection.

The Ad-sig-H5HA/ecdhCD40L vector was processed for administration in accordance with the methods of reference *PNAS* 2003 100:15101-15106; *Blood* 2004 104:2704-2713, was injected twice (at a 7 day interval) sc into immunocompetent mice (2 months old). Seven days following the immunization, the CD8 cells were isolated, and incubated for 2 days in the presence of the H5HA epitope (cultured with syngeneic gamma-irradiated spleen cells pulsed with HA peptides and cultured for 48 hours, and developed according to the ELISPOT protocol (see *PNAS* 2003 100: 15101-15106; *Blood* 2004 104:2704-2713), and then the spleen cells were tested by ELISPOT assay for the level of H5HA specific CD8 T cells before and after vaccination. As shown in FIG. 18, the level of H5HA specific CD8 T cells increased significantly in the spleen of the vaccinated mice (N=4) compared to the unvaccinated mice (N-4), $p<0.05$.

c) Induction of Immunity in Old and Young Mice

Figure 23:
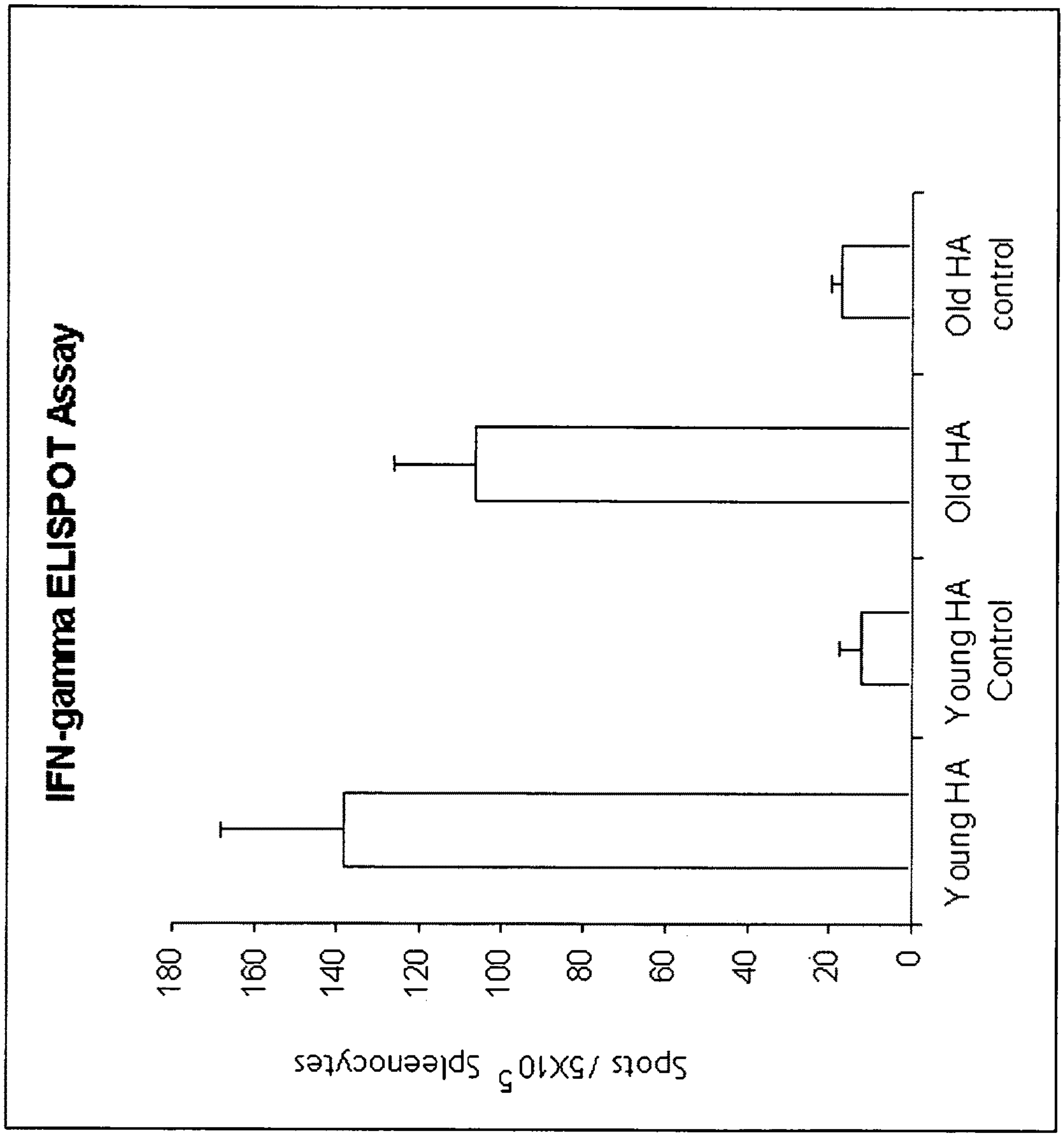
FIG. 23 depicts the level of CD8 T cells in a preparation of splenocytes from Ad-sig-H5HA/ecdCD40L vaccinated old and young mice compared to unvaccinated mice, as determined by via ELISpot assay interferon gamma detection.
Figure 24:
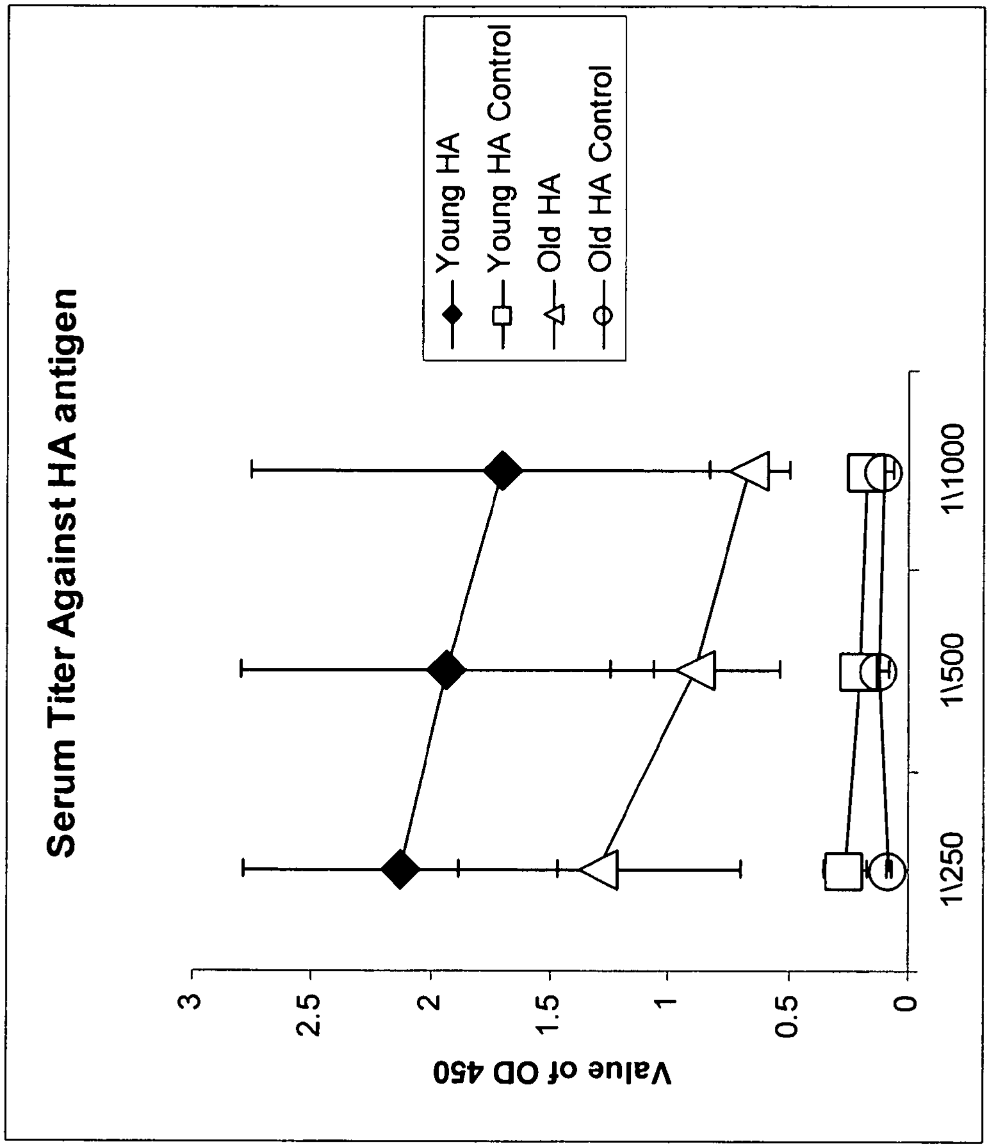
FIG. 24 demonstrates the presence of antibodies against HA in serum of old and young mice following vaccination with Ad-sig-H5HA/ecdCD40L vector followed by three protein boosts of HA/ecdCD40L fusion protein.

Two month old ("Young") C57BL6 mice (n=4) and in 18 month old ("Old") C57BL6 mice (n=4) were administered with one subcutaneous injection of Ad-sig-HA/ecdCD40L vector followed by 3 separate injections of HA/ecdCD40L fusion protein at 7 day intervals starting 7 days after the initial vector injection. Age-matched unvaccinated mice served as controls. The levels of HA specific splenic CD8 T cells were determined by ELISPOT assay and the levels of the HA specific serum antibodies were determined by ELISA assay for all groups. As shown in FIG. 23, the levels of HA specific splenic CD8 T cells of the vaccinated mice were statistically significantly increased in the vaccinated groups as compared to an age-matched unvaccinated control group for the 2 month old mice (p=0.0004) and the 18 month old mice (p=0.0001). FIG. 24 shows that the level of serum antibodies specific for the H5N1 HA antigen was statistically significantly increased in the vaccinated groups as compared to an age-matched unvaccinated control group for 2 month old mice (p=0.004) and 18 month old mice (p=0.015) (determined at a 1/250 dilution).

15. Induction of Immunity with the Ad-sig-H5N1M2/ecdCD40L Vector Against the M2 Protein of the H5N1 Avian Influenza Virus in 2 Month Old Mice and 18 Month Old Mice The H5N1 M2 protein does not change in strains with influenza viral strains harboring transitions of sequence in the HA antigens. However, it is a weak antigen during vaccination. Thus, a portion of the coding sequence of the M2 gene was linked to the extracellular domain of CD40 ligand in the Ad-sig-M2/ecdCD40L to increase its immunogenicity.

a) Construction of Ad-sig-H5N1M2/ecdCD40L Vectors

As discussed, the M2 protein is not normally immunogenic, but can be made so by including it in a chimeric protein with another immunogenic protein sequence. The amino terminal end or an internal "immunodominant loop" from the extracellular domain of the M2 was used in such chimeric structures.

An Ad-K-M2/ecdCD40L vector where the M2 is from an H5N1 influenza virus is constructed to generate an immune response to the M2.

The amino acid sequence of a portion of an M2 protein corresponding to amino acid residues 1-24 of the M2 protein of an H5N1 Influenza A virus (A/Hong Kong/156/97), wherein the cysteine residues at positions 17 and 19 in the native protein have been mutated to serine residues as reported by De Fillette et al. (Virology 337:149-61, 2005) is shown below.

```
                                        (SEQ ID NO: 77)
            MSLLTEVDTLTRNGWGSRSSDSSD
```

Oligonucleotides corresponding to the sense and antisense strands of the DNA encoding SEQ ID NO:77 are as follows:

```
M2 sense oligonucleotide:
                                        (SEQ ID NO: 78)
5'-ATGA GCCTTCTAAC CGAGGTTGAC ACGCTTACCAGA

AACGGATGGG GGTCCAGATC CAGCGATTCA AGTGAT-3'

M2 antisense oligonucleotide:
                                        (SEQ ID NO: 79)
5'-ATCACTTGAATCGCTGGATCTGGACCCCCATCCGTTTCTGGTAAGC

GTGTC AACCTCGGTTAGAAGGCTCAT-3'
```

The oligonucleotides were dissolved in STE buffer at high concentration (about 1-10 $OD_{260}$ units/100 μL). The two strands were mixed together in equal molar amounts and heated to 94° C. and slowly cooled to about 4° C. The annealed DNA was phosphorylated using T4 PNK (polynucleotide kinase) under standard conditions. The resulting double stranded DNA was amplified by PCR using the following primers:

```
Primer 1:
                                        (SEQ ID NO: 80)
5'-ACG ATG GAG ACA GAC ACA CTC CTG CTA TGG GTA

CTG CTG-3'

Primer 2
                                        (SEQ ID NO: 81)
5'-TC CTG CTA TGG GTA CTG CTG CTC TGG GTT CCA GGT

TC-3'

Primer 3:
                                        (SEQ ID NO: 82)
5'-TG CTC TGG GTT CCA GGT TCC ACT GGT GAC ATG-3';

Primer 4:
                                        (SEQ ID NO: 83)
5'-TGG GTT CCA GGT TCC ACT GGT GAC ATG ATGA

GCCTTCTAAC CGAGGTTGAC-3';
```

-continued and

Primer 5:

(SEQ ID NO: 84)

5'-CCG CTCGAG ATCACTTGAATCGCTGCATCTGCACC-3'.

The K/Avian FluM2 fragment having an upstream kappa signal sequence was generated by four rounds of PCR amplification ($1^{5}$ round: primers 4 +5; $2^{nd}$ round: add primer 3; $3^{rd}$ round: add primer 2; $4^{th}$ round: add primer 1). The K/Avian FluM2 encoding DNA was subcloned into the pcDNA™ 3.1 TOPO vector (Invitrogen, San Diego, Calif.) resulting in plasmid pcDNA-K/Avian FluM2.

The "spacer+ΔCtΔTmCD40L(mouse)" fragment was cut from the pcDNA3TOPO-sp-ΔCtΔTmCD40L using Xho I and Xba I and was inserted into the plasmid pcDNA-K/Avian FluM2 after restriction endonuclease digestion with XbaI (TCTAGA) and Xho I (CTCGAG). The K/Avian-FluM2/ΔCtΔTmCD40L (mouse) encoding DNA was cut from the pCDNA3TOPO using HindIII-XbaI restriction and inserted into pShuttle-CMV downstream of the CMV promoter. This vector is designated pShuttle sig AfluM2/ΔCtΔTmCD40L(mouse).

Recombinant adenoviral vectors were generated using the AdEasy vector system (Stratagene, San Diego, Calif.) as described above, resulting in the Ad-K/AvianFluM2/ecdCD40L vector. Fusion protein was prepared as described below.

b) Induction of Immunity in Old and Young Mice

Figure 25:
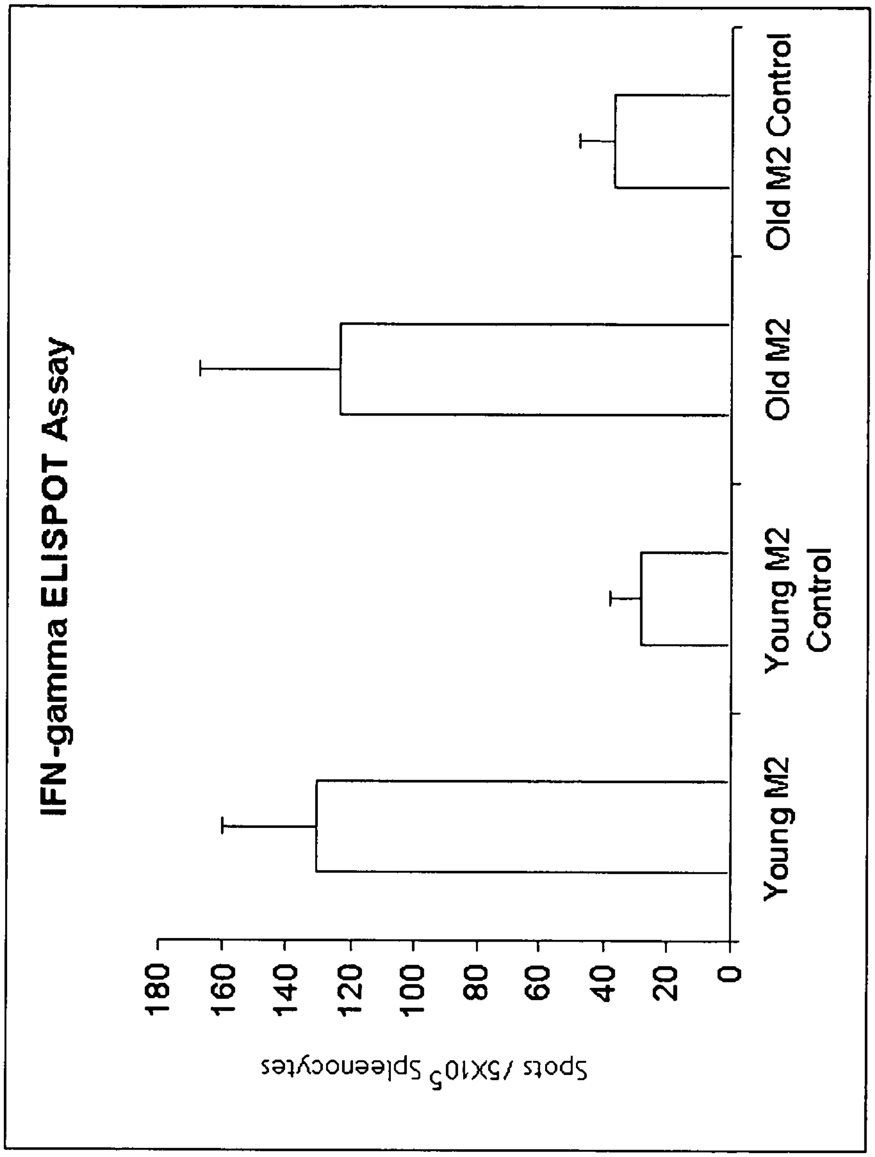
FIG. 25 depicts the level of M2-specific CD8 T cells in a preparation of splenocytes from Ad-sig-H5M2/ecdCD40L vaccinated old and young mice compared to unvaccinated mice, as determined by via ELISpot assay interferon gamma detection.
Figure 26:
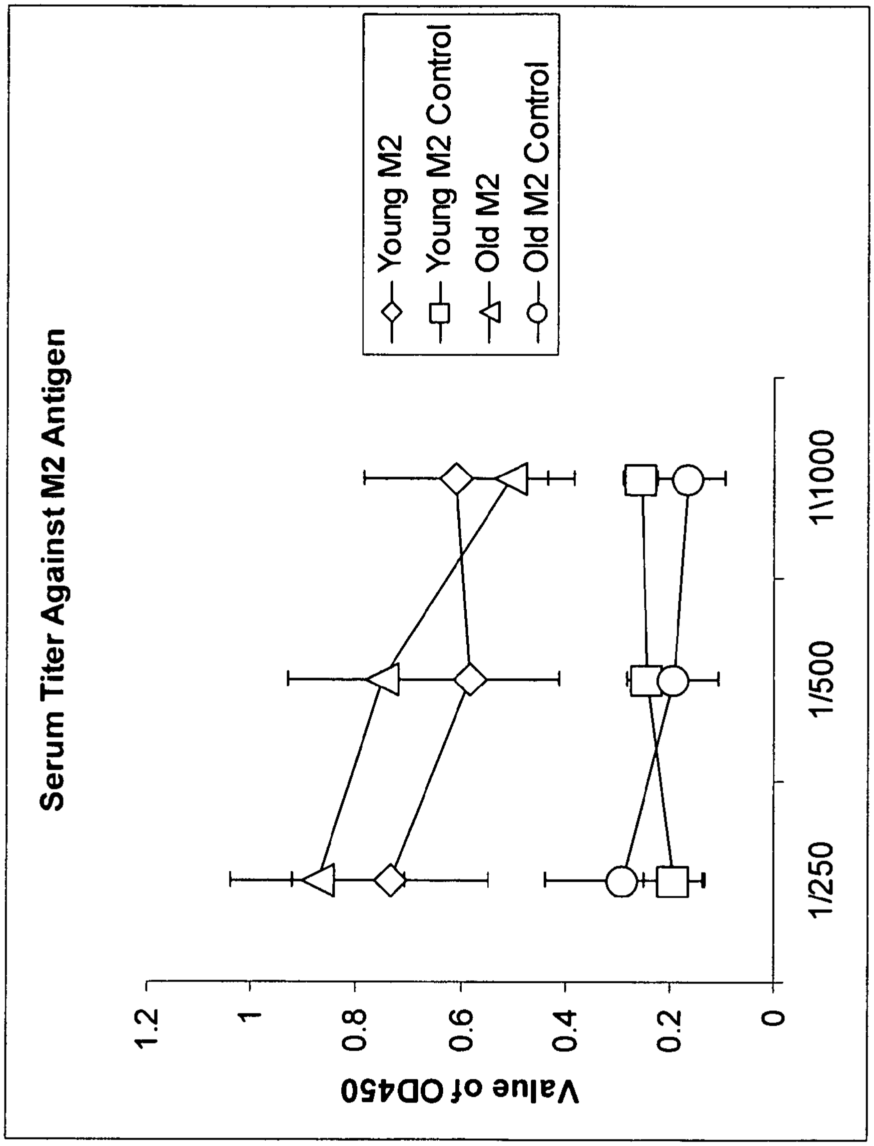
FIG. 26 demonstrates the presence of antibodies against M2 in serum of old and young mice following vaccination with Ad-sig-H5M2/ecdCD40L vector followed by two protein boosts of M2/ecdCD40L fusion protein.

Two month old C57BL6 mice (n=5) and in 18 month old C57BL6 mice were administered with one subcutaneous injection of Ad-sig-M2/ecdCD40L vector followed by injections of M2/ecdCD40L fusion protein 7 and 21 days after the initial vector injection. Age-matched unvaccinated mice served as controls. The levels of M2 specific splenic CD8 T cells were determined by ELISPOT assay and the levels of the M2 specific serum antibodies were determined by ELISA assay for all groups. As shown in FIG. 25, the levels of M2 specific splenic CD8 T cells of the vaccinated mice were statistically significantly increased in the vaccinated groups as compared to an age-matched unvaccinated control group for both the 2 month old ( )0.0006), as well as the 18 month old mice (p=0.0009). FIG. 26 shows that the level of serum antibodies specific for the H5N1 M2 antigen was statistically significantly increased in the vaccinated groups as compared to an age-matched unvaccinated control group for 2 month old mice (p=0.0028) and 18 month old mice (p=0.0025) (determined at a 1/250 dilution). These data shows that the linkage of the CD40L to the M2 protein in the Ad-sig-M2/ecdCD40L vaccine prime-M2/ecdCD40L protein boost vaccine induces a significant immune response.

16. Construction of Ad-sig-H5HA-M2/ecdCD40L chimeric vectors

An Ad-sig-TAA/ecdCD40L vectors carrying an antigen which is a chimeric fusion of the HA and the M2 proteins is constructed as follows. The H5N1 HA and M2 sequences are synthesized by PCR amplification from an H5N1 template. An exemplary DNA sequence encoding an H5N1 HA antigen is as follows.

(SEQ ID NO: 69)

5'-

AAAAGTTCTTGGTCCAATCATGATGCCTCATCAGGGGTGAGCTCAGCA

TGTCCATACCTTGGGAGGTCCTCCTTTTTCAGAAATGTGGTATGGCTTA

-continued

TCAAAAAGAACAGTGCATACCCAACAGCTACTAGACCCAAAGTAAAC

GGGCAAAGTGGAAGAATGGAGTTCTTCTGGACAATTTTAAAG-3'.

DNA sequence encoding a chimera HA-M2 is shown below with the H5N1 HA sequence 5' to the M2 sequence. The underlined segment is added sequence between the above two segments.

(SEQ ID NO: 43)

5'-AAAAGTTCTTGGTCCAATCATGATGCCTCATCAGGGGTGAGCTCAG

CATGTCCATACCTTGGGAGGTCCTCCTTTTTCAGAAATGTGGTATGGCT

TATCAAAAAGAACAGTGCATACCCAACAGCTACTAGACCCAAAGTAA

ACGGGCAAAGTGGAAGAATGGAGTTCTTCTGGACAATTTTAAAGGAT

ATCATGAGCCTTCTAACCGAGGTTGACACGCTTACCAGAAACGGATGG

GGGTGCAGATGCAGCGATTCAAGTGAT-3'.

The above DNA encodes the following chimeric HA-M2 protein:

(SEQ ID NO: 85)

KSSWSNHDASSGVSSACPYLGRSSFFRNVVWLIKKNSAYPTATRPKVNG

QSGRMEFFWTILKDIMSLLTEVDTLTRNGWGCRCSDSSD.

The above HA-M2 chimeric sequence is cloned downstream of a secretory signal sequence (e.g., mouse 1gG kappa chain signal or secretory sequence) (sig). This sig HA-M2 molecule is then linked via a 30 nucleotide linker sequence to DNA for ecdhCD40L. The TAA/ecdCD40L transcription unit is inserted into the Ad-sig-TAA/ecdCD40L vector by methods previously described and reported (see e.g., PNAS 2003 100:15101-15106; Blood 2004 104:2704-2713). The vector is then isolated from 293 cells, plaque purified, and the TAA/ecdCD40L insert sequenced and tested for replication competent adenovirus by PCR assay for EIA.

17. Testing and use of the Adenovirus Expression Constructs

HA, NA, or M2 from H5N1, H3N2 or other Type A viral strains such as H2N2 or H1N1 are cloned into the TAA/ecdCD40L vector. The influenza fusion protein is expressed and used as a protein boost. Generally, the vector is administered two times (7 days apart), or a vector is injection followed by 2 protein boosts at 7 and 21 days. Subjects are vaccinated with the Ad-sig-TAA/ecdCD40L vector where the TAA is replaced with an influenza antigen.

a) In Vitro Stability of TAA/ccdCD40L and Activation of DCs

The stability of the expressed influenza antigen proteins is evaluated as follows. The TAA/ecdCD40L protein is generated with a hexhis tag and once released from 293 infected cells, it is purified by a nickel column. The protein is studied by reducing and non-reducing SDS-PAGE gels to determine if the trimeric structure is stable with the HA, M2 or HAM2 as antigen. Western blotting is used with a flag antibody to test the relative stability of the HA/ecdCD40L, M2/ecdCD40L and the HAM2/ecdCD40L proteins by methods reported previously (see Blood 2004 104:2704-2713). The recombinant protein is added to mouse bone marrow derived dendritic cells (DCs) by methods reported previously (Deisseroth et al., DC Vector Vaccine and Chemotherapy in Breast Cancer, Submitted 2006). The endpoint of these studies is: FACS analysis of the DCs for appearance of CD 86 and PCR assay for expression of the CCR7 gene (PNAS 2004 100:15101-15106; Blood 2004 104:2704-2713), b) In Vivo Induction of Immune Response with each Ad-sig-TAA/ecdCD40L Induction of immune response is evaluated for each influenza vaccine vector as follows, Two sc injections at 7 day intervals are administered to 2 month and 18 month old BalbC mice. Seven, 14 and 21 days following the last injection, the animal is sacrificed and the following assays carried out.

a. ELISA for AG specific antibodies in serum (see *Blood* 2004 104: 2704-2713 for method).
b. ELISPOT and CTL assays for level of AG specific CD8 effector cells in spleen (see *Blood* 2004 104: 2704-2713 for method).
c. Determine the levels of CD8 Effector T cells and CD4 T negative regulatory cells at the site of AGG inflammation.

The levels of CD8 and CD4 cells are evaluated. Two and 18 month old BAC mice are injected sc with a syngeneic tumor cell line carrying the HA or M2 or HAM2 transcription unit. When the tumor nodule reaches the size of 150 cu mm, the test mouse is injected sc with the Ad-sig-TAA/ecdCD4011, vector (2 injections 7 days apart). Seven days following the last vaccination, the animal is sacrificed. The tumor is minced, treated with DNAase and collagenase, filtered through nylon mesh and the frequency of CD8 effector cells and CD4CD25FOXP3 T neeative regulatory cells is measured by FACS before and after vaccination.

d) Suppression of Growth of TAA Positive Syngeneic Tumor Cell Line

Suppression of growth of influenza antigen positive cell-lines is also evaluated. The syngeneic HA positive or M2 positive or HAM2 positive syngeneic cell line (500,000 cells) are injected sc into 2 month or 18 month old mice. A growth curve is followed in mice that were vaccinated with two Ad-sig-TAA/ecdCD40L injections (7 days apart) prior to the injection of the tumor cell line. The growth curve is the endpoint of the experiment.

e) Effect of Vaccination Based on One Ad-sig-TAA/ecdCD40L sc Injection Followed by Two TAAJecdCD40L Protein Injections as Boost In the above Examples, it was shown that a single Ad-sig-TAA/ecdCD40L sc injection followed by two sc injections of 10 microgram of the TAA/ecdCD40L protein at 7 and 21 days produced dramatic increases in the levels of both antigen specific antibodies in the serum and TAA specific CD8 effector T cells in test mice. Influenza antigen Ad-sig-TAA/ecdCD40L single vector injection followed by two sc (10 microgram) TAAJecdCD40L protein boost injections at 7 and 21 days is used.

The number of boosts, the route of administration of the vaccine, and the addition of adjuvant are modified to illicit an adequate increase in antigenic specific CD8 cells as determined by ELISPOT (200 positive cells/100,000 spleen cells) or antibodies (6-fold increase).

18. Induction of Immunity with Influenza Antigen/CD40 Ligand Fusion Protein Against the Hemagglutinin Protein of an H5N1 Influenza A Virus in 2 Month Old Mice SEQ ID NO:21 represents a portion of the HA sequence from an H5N1 Influenza A virus (A/Hong Kong/156/97) was used as an antigen in the HA-CD40L fusion protein. As described below, this fusion protein induced an immune response in mice; as shown by the level of anti-E15 HA antibody in the serum of vaccinated animals.

SEQ ID NO:21 is present in the receptor binding region corresponding to amino acid residues 135-175 connected to residues 230-250 (see FIG. 2, underlined) of the hemagglutinin (HA) protein of the H5N1 avian influenza strain (HSHA). This strain was first isolated in 1997 in Hong Kong from a child with a fatal respiratory illness (see, e.g., Science 1998 279:393-96; J. Virology 1998 73: 2094-98; Emerging Infectious Disease 2002 8(8):1-12).

```
                                        (SEQ ID NO: 21)
KSSWSNHDASSGVSSACPYLGRSSFFRNVVWLIKKNSAYPTATRPKVNG

QSGRMEFFWTILK.
```

The HA-CD40L fusion was prepared as follows. A CD40L plasmid was generated by PCR amplifying HSF1/ΔCtΔTmCD40L using plasmid pcDNA-sig-hMUC-1/HSF1/ΔCtΔTmCD40L as template (the construction of this plasmid is described in U.S. Patent Application Publication US 2005-0226888). The PCR primers and conditions for PCR are as follows:

Primer 1 (forward) (XcmI restriction site underlined; EcoRV restriction site underlined and italicized):

(SEQ ID NO: 86)

5'-AA <u>CCA TCA CTC TTC TGG</u> T <u>*GAGCTC*</u> AAA GATATC

AACGA CGCACAAGC-3';

Primer 2 (forward) (EcoRV restriction site underlined and italicized):

(SEQ ID NO: 87)

5'-GCTCAAA <u>*GATATC*</u> AACGACGCACAAGCACCAAAATCA

AAGGTC-3';

and

Primer 3 (reverse) (EcoRI restriction site underlined and bold):

(SEQ ID NO: 88)

5'-AT CTCGAG CG <u>GAATTC</u> CAGAGTTTGAGTAAGCCAAAAGA

TGAGAAGCC-3'.

HSF1/ΔCtΔTm CD40L was amplified by two rounds of PCR amplification (1st round: primers 2+3; 2nd round: primer 1+3). PCR was conducted using the GC-RICH PCR kit (Roche, Inc) under the following conditions:

| Cycles | Temperature | Time |
|---|---|---|
| 1 | 95° C. | 3 min. |
| 30 | 95° C. | 45 sec. |
| | 55° C. | 45 sec. |
| | 72° C. | 1 min. |
| 1 | 72° C. | 7 min. |

The HSF1/ΔCtΔTm CD40L encoding DNA was subcloned into pTriEx-2 restriction sites XcinI (CCA TCA CTC TTC TGG) and EcoRt (GAATTC). The final vector was named pTriEx-2 HSF1/ΔCtΔTm CD40L.

The cDNA encoding the HA antigen above (SEQ ID NO:21) was amplified from plasmid pcDNA-K/Avian FluHA (described above) using the following PCR primers:

HA forward primer (XcmI restriction site underlined):

(SEQ ID NO: 89)

5'-AA <u>CCATCACTCTTCTGG</u>

TAGATCTAAAAGTTCTTGGTCCAATC-3'

-continued

```
and

HA reverse primer (XhoI restriction site
underlined):
                                    (SEQ ID NO: 90)
5'-AAA CTCGAG TCT GATATC

CTTTAAAATTGTCCAGAAGAACTC-3'.
```

PCR was conducted under the following conditions:

| Cycles | Temperature | Time |
|---|---|---|
| 1 | 95° C. | 3 min. |
| 30 | 95° C. | 30 sec. |
| | 58° C. | 30 sec. |
| | 72° C. | 30 sec. |
| 1 | 72° C. | 7 min. |

The PCR amplification product was ligated into pcDNA3.1/V5-His TOPO TA vector and named as pcDNA3.1/HA then subcloned into the expression plasmid pTriEx-2 HSF1/ΔCtΔTmCD40L using the XcmI and EcoRV sites to produce the plasmid pTriEx-2HA/mCD40L. Competent cells (Rosetta DE3 pLace were transformed with pTriEx-2HAmCD40L and single colony of transformed cells was selected. His-tagged HA/mCD40L fusion protein was produced from the transformed cells using the Overnight Express™ Autoinduction System (Novagen, Following protein expression, the resulting media containing the cells was centrifuged at 5000 g for 10 minutes and the resulting supernatant discarded. Cells were lysed using the CelLytic B Plus Kit (Sigma, Inc.) as follows: 10 mL Lytic Buffer was added for each gram of pelleted cells; the Lytic Buffer was prepared by adding 10 mL CelLytic B reagent, 0.2 mL lysozyme, 0.1 mL protease inhibitor and 500 U benzonase; cells were resuspended in Lytic Buffer and incubated with shaking at RT for 10-15 minutes; and lysed cells were centrifuged 16,000g for 10 minutes. Fusion protein was purified by HIS-Select Nickel Affinity Gel (Sigma, Inc.) as follows: 1 mL of His-Select Nickel Affinity Gel was prepared for each 10 mL of cell lysate supernatant and the fusion protein isolated using the "Batch Method" protocol from the manufacturer and performing 3 wash steps before the final elution of the His-tagged fusion protein; and the eluted protein (in 3 mL buffer) was applied to a 10DG desalting column and extracted from the column using 4 mL PBS. The eluted protein was concentrated using a Vivaspin column.

The H5HA/ecdCD40L fusion protein (10 μg) was injected subcutaneously into immunocompetent mice (2 months old) on days 0, 7, and 21 with or without 100 μg aluminum hydroxide hydrogel. Seven days following the third immunization, serum samples were collected and assayed by ELISA for antibody to HA. As shown in FIG. 25, the level of H5HA specific antibodies in both groups (i.e., with and without aluminum hydroxide) are significantly higher in the sera of vaccinated mice (N=4) compared to the control mice injected only with PBS (N=4).

The neutralizing dose ($ND_{50}$) of the antibody to HA was determined using the following method.

MDCK cells were harvested and the cell suspension diluted to $3\times10^5$ cells/mL (or other appropriate concentration so that the cells are at least 90% confluent at the initiation of theassay). 200 μL of the diluted cell suspension was transferred into each well of a 96-well microplate and incubated at 37±2° C. and 5.0±2% $CO_2$ for a minimum of 16 hours in a humidified incubator until the wells were at least 90% confluent. Serum samples were obtained from the above-described mice vaccinated with HA/ecdCD40L, 7 days after the third immunization. 300 μL aliquots of serum were serially diluted in inoculation medium (dilutions of 1:5 to 1:2560). The virus challenge solution was prepared by diluting the challenge virus to 200 $TCID_{50}$/100 μl (or $2\times10^3$ $TCID_{50}$/mL) in inoculation media. 300 μL of virus challenge solution was added to each serum dilution to produce inoculating solutions having a final serum dilution of 1:10 to 1:5120 and incubated at 37±2° C. and 5.0±2% $CO_2$ in a humidified incubator for 1 hour±5 minutes. Each well of the plate containing the MDCK cells was washed once with 200 μL Hank's Balanced Salt Solution (HBSS), inoculated with 100 μL of inoculating solution and incubated at 37±2° C. and 5.0±2% $CO_2$ in a humidified incubator for a minimum of 16 hours or until cytopathological effects (CPE) are evident in comparison to control (no virus) wells. The $ND_{50}$ is the dilution that results in the absence of CPE in 50% of the wells inoculated was calculated using the Spearman Kärber method.

At a targeted challenge concentration of virus of 20 ($TC_{50}$/mL), the serum from HA immunized animals showed a neutralizing titer of $4.56\times10^3$. At a ten-fold higher dilution of challenge virus (i.e., 200 ($TC_{50}$/mL)) no neutralizing effect of the serum from HA immunized animals was observed.

19. Induction of Immunity with Influenza Antigen/CD40 Ligand Fusion Protein Against the M2 Protein of an HSM Influenza A virus in 2 Month Old Mice A portion of the M2 amino acid sequence from an H5N1 Influenza A virus (A/Hong Kong/156/97) was used as an antigen in the M2/ecdCD40L fusion protein. As described below, this fusion protein induced an immune response in mice; that is, a significant level of anti-M2 antibody was detected in the serum of vaccinated animals.

The amino acid sequence of a portion of an M2 protein corresponding to amino acid residues 1-24 of the M2 protein of an H5N1 Influenza A virus (A/Hong Kong/156/97), wherein the cysteine residues at positions 17 and 19 in the native protein have been mutated to serine residues as reported by De Fillette et al. (Virology 337:149-61, 2005) is shown below.

```
                                    (SEQ ID NO: 77)
          MSLLTEVDTLTRNGWGSRSSDSSD
```

Oligonucleotides corresponding to the sense and antisense strands of the DNA encoding SEQ ID NO:77 are as follows:

```
M2 sense oligonucleotide:
                                    (SEQ ID NO: 78)
5'-ATGA GCCTTCTAAC CGAGGTTGAC ACGCTTACCAGA

AACGGATGGG GGTCCAGATC CAGCGATTCA AGTGAT-3'

M2 antisense oligonucleotide:
                                    (SEQ ID NO: 79)
5'-ATCACTTGAATCGCTGGATCTGGACCCCCATCCGTTTCTGGTAAGC

GTGTC AACCTCGGTTAGAAGGCTCAT-3'
```

The oligonucleotides were dissolved in STE buffer at high concentration (about 1-10 $OD_{260}$ units/100 μL). The two strands were mixed together in equal molar amounts and heated to 94° C. and slowly cooled to about 4° C. The annealed DNA was phosphorylated using T4 PNK (polynucleotide kinase) under standard conditions. The resulting double stranded DNA was amplified by PCR using the following primers:

```
M2 forward primer (XcmI restriction site
underlined):
                                  (SEQ ID NO: 91)
5'-AA CCATCACTCTTCTGG T AGATCT ATGA GCCTTCTAAC
CGAGGTTGAC-3

M2 reverse primer (XhoI restriction site
underlined):
                                  (SEQ ID NO: 92)
5'-AAA CTCGAG TCT GATATC

ATCACTTGAATCGCTGGATCTGG-3'
```

PCR was conducted under the following conditions:

| Cycles | Temperature | Time |
|---|---|---|
| 1 | 95° C. | 3 min. |
| 30 | 95° C. | 30 sec. |
| | 58° C. | 30 sec. |
| | 72° C. | 20 sec. |
| 1 | 72° C. | 7 min. |

The PCR amplification product was ligated into pcDNA3.1/V5-His TOPO TA vector and named as pcDNA3.1/M2 then subcloned into the expression plasmid pTriEx-2 HSF1/ΔCtΔTmCD40L using the XcmI and EcoRV sites to produce the plasmid pTriEx-2M2/mCD40L. Competent cells (Rosetta DE3 pLacI) were transformed with pTriEx-2 M2mCD40L and single colony of transformed cells was selected. His-tagged M2/mCD40L fusion protein was produced from the transformed cells using the Overnight Express™ Autoinduction System (Novagen, Inc.). Following protein expression, the resulting media containing the cells was centrifuged at 5000 g for 10 minutes and the resulting supernatant discarded. Cells were lysed using the CelLytic B Plus Kit (Sigma, Inc.) as follows: 10 mL Lytic Buffer was added for each gram of pelleted cells; the Lytic Buffer was prepared by adding 10 mL CelLytic B reagent, 0.2 mL lysozyme, 0.1 mL protease inhibitor and 500 U benzonase, cells were resuspended in Lytic Buffer and incubated with shaking at RT for 10-15 minutes; and lysed cells were centrifuged 16,000 g for 10 minutes. The fusion protein was purified by HIS-Select Nickel Affinity Gel (Sigma, Inc.) as follows: 1 mL of His-Select Nickel Affinity Gel was prepared for each 10 mL of cell lysate supernatant and the fusion protein isolated using the "Batch Method" protocol from the manufacturer and performing 3 wash steps before the final elution of the His-tagged fusion protein; and the eluted protein (in 3 mL buffer) was applied to a 10DG desalting column and extracted from the column using 4 mL PBS. The eluted protein was concentrated using a Vivaspin column.

The M2/ecdCD40L fusion protein (10 μg) was injected subcutaneously into immunocompetent mice (2 months old) on days 0, 7, and 21 with or without 100 μg aluminum hydroxide hydrogel. Seven days following the third immunization, serum samples were collected and assayed by ELISA for antibody to M2. As shown in FIG. 26, the level of M2 specific antibodies in both groups (i.e., with and without aluminum hydroxide) are significantly higher in the sera of vaccinated mice (N=4) compared to the control mice injected only with PBS (N=4).

The neutralizing dose ($ND_{50}$) of the sera from M2 immunized mice was determined using the method as described in the preceding example. At a targeted challenge concentration of virus of 20 ($TC_{50}$/mL), the serum from M2 immunized animals showed a neutralizing titer of $1.27\times10^2$. At a ten-fold higher dilution of challenge virus (i.e., 200 ($TC_{50}$/mL)) no neutralizing effect of the serum from M2 immunized animals was observed.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A vaccine composition for generating in an individual an immune response against one or more influenza antigens resulting from an infectious influenza virus, comprising:

an effective amount of an expression vector, said expression vector comprising a transcription unit encoding a secretable fusion protein comprising at least first and second influenza antigen fragments, each influenza antigen fragment from an extracellular region of the influenza virus, and each of said first and second influenza antigen fragments comprising at least first and second epitopes wherein the first and second influenza antigen fragments are linked to the amino terminus of an extracellular domain of a CD40 ligand, for generating both a cellular and antibody immune response, said first influenza antigen fragment comprising, the first epitope that is recognized and bound by Class II MHC for eliciting antigen specific antibodies, and the second epitope that is recognized and bound by Class I MHC for eliciting antigen specific $CD8^+$ effector T cells, and said second influenza antigen fragment comprising the first epitope that is recognized and bound by Class II MHC for eliciting antigen specific antibodies, and the second epitope that is recognized and bound by Class I MHC for eliciting antigen specific $CD8^+$ effector T cells, wherein each of said epitopes in both the first and second influenza antigen fragments has a distinct amino acid sequence from each of the other epitopes.

2. The composition of claim 1 wherein said influenza antigen fragments are from an influenza virus belonging to at least one or both of classes H3N2 or H5N1.

3. The composition of claim 1 wherein each of said influenza antigen fragments is from a different viral influenza protein.

4. The composition of claim 1 wherein at least one of said first and second influenza antigen fragments is from the extracellular domain of hemagglutinin or neuraminidase or Matrix protein 2.

5. The composition of claim 1 wherein said expression vector is a viral vector or a plasmid vector.

6. The composition of claim 5 wherein said viral vector is an adenoviral vector.

7. The composition of claim 1 wherein said antibodies are neutralizing antibodies.

8. The composition of claim 1 wherein the transcription unit encodes a secretory signal sequence linked to the first and second influenza antigen fragments connected to a linker connected to the extracellular domain of the CD40 ligand.

9. A vaccine composition for increasing the immune responsiveness in an individual against one or more foreign antigens on an infectious agent, comprising:

an expression vector comprising a transcription unit encoding a secretable fusion protein comprising two or more foreign antigen fragments each from the extracellular domain of the one or more foreign antigens on the infectious agent, and an extracellular domain of a CD40L ligand, wherein the two or more foreign antigen fragments are linked to an amino terminus of the extracellular domain of the CD40L ligand, a first one of said foreign antigen fragments comprising a first epitope that contains a binding site that is recognized and bound by Class II MHC for eliciting foreign antigen specific antibodies, and further comprising a second epitope that contains a binding site that is recognized and bound by Class I MHC for eliciting foreign antigen specific $CD8^+$ T cells, and a second one of said foreign antigen fragments comprising a first epitope and a second epitope, each of said first and second epitopes in the second foreign antigen fragment having a distinct amino acid sequence from each of the amino acid sequence epitopes in the first foreign antigen fragment, and said first and second epitopes of said second foreign antigen each having a binding site respectively recognized and bound by Class II MHC and Class I MHC.

10. The composition of claim 9 wherein said infectious agent comprises one or more proteins of the same strain or different strains and said foreign antigen fragments are from said one or more proteins.

11. The composition of claim 9 wherein said infectious agent is one of bacterial, fungal, viral or protozoan.

12. The composition of claim 9 wherein said foreign antigen specific antibodies are neutralizing antibodies.

13. A vaccine composition employing an expression vector comprising a transcription unit encoding a secretable fusion protein comprising first and second connected and distinct foreign antigen fragments, each fragment from a different protein of an infectious agent, and an extracellular domain of a CD40 ligand, said first foreign antigen fragment from a first protein comprising at least first and second epitopes linked to the amino terminus of the extracellular domain of said CD40 ligand, wherein:

the first one of said epitopes that contains antigenic determinant that includes a binding site that is recognized and bound by Class II MHC for eliciting foreign antigen specific antibodies, and the second one of said epitopes that contains antigenic determinant that includes a binding site that is recognized and bound by Class I MHC for eliciting foreign antigen specific $CD8^+$effector T cells, and said second foreign antigen fragment from a second protein, and comprising at least a first epitope and a second epitope, said second fragment first epitope and second epitope each containing a binding site that is respectively recognized and bound by Class II MHC and Class I MHC.

14. The composition of claim 13 wherein said foreign antigen specific antibodies are neutralizing antibodies.

15. The composition of claim 13 wherein the first and second foreign antigen fragments are each from proteins of the same strain or different strains.

16. The composition of claim 13, wherein said foreign antigen fragments are one of bacterial, fungal, viral or protozoan.

17. A composition for generating an immune response in an individual against one or more influenza antigens on an infectious agent for limiting progression of the infectious agent for multiple strains of the influenza virus, comprising, an expression vector comprising a transcription unit encoding a secretable fusion protein comprising the extracellular domain of the CD40 ligand and an extracellular portion of the Matrix protein 2 influenza antigen SEQ ID NO 77, wherein said Matrix protein 2 is connected at the amino terminus of the CD40 ligand and functions to increase the immunogenicity of said Matrix protein 2 so as to increase both the level of Matrix protein 2 specific $CD8^+$ effector T cells and neutralizing antibodies, against the infectious agent.

* * * * *

SEQUENCE LISTING

```
<160> NUMBER OF SEQ ID NOS: 94

<210> SEQ ID NO 1
<211> LENGTH: 97
<212> TYPE: PRT
<213> ORGANISM: Influenza A virus

<400> SEQUENCE: 1

Met Ser Leu Leu Thr Glu Val Glu Thr Leu Thr Arg Asn Gly Trp Gly
1               5                   10                  15

Cys Arg Cys Ser Asp Ser Ser Asp Pro Leu Val Val Ala Ala Ser Ile
```

-continued

```
            20                  25                  30

Ile Gly Ile Leu His Leu Ile Leu Trp Ile Leu Asp Arg Leu Phe Phe
        35                  40                  45

Lys Cys Ile Tyr Arg Arg Phe Lys Tyr Gly Leu Lys Arg Gly Pro Ser
    50                  55                  60

Thr Glu Gly Val Pro Glu Ser Met Arg Glu Glu Tyr Arg Gln Glu Gln
65                  70                  75                  80

Gln Asn Ala Val Asp Val Asp Asp Gly His Phe Val Asn Ile Glu Leu
                85                  90                  95

Glu


<210> SEQ ID NO 2
<211> LENGTH: 552
<212> TYPE: PRT
<213> ORGANISM: Influenza A virus

<400> SEQUENCE: 2

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Arg Thr His Asn Gly Lys Leu Cys Asp Leu Asn Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Ser Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asn His Asp Ala Ser
        115                 120                 125

Ser Gly Val Ser Ser Ala Cys Pro Tyr Leu Gly Arg Ser Ser Phe Phe
    130                 135                 140

Arg Asn Val Val Trp Leu Ile Lys Lys Asn Ser Ala Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Glu Ile Ala Thr Arg Pro Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
```

-continued

```
    290                 295                 300

Tyr Val Lys Ser Asn Arg Leu Val Leu Ala Thr Gly Leu Arg Asn Thr
305                 310                 315                 320

Pro Gln Arg Glu Arg Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365

Glu Ser Thr Gln Lys Ala Ile Asp Gly Val Thr Asn Lys Val Asn Ser
    370                 375                 380

Ile Ile Asn Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Lys Cys Asp Asn Glu Cys Met Glu
465                 470                 475                 480

Ser Val Lys Asn Gly Thr Tyr Asp Tyr Pro Gln Tyr Ser Glu Glu Ala
                485                 490                 495

Arg Leu Asn Arg Glu Glu Ile Ser Gly Val Lys Leu Glu Ser Met Gly
            500                 505                 510

Thr Tyr Gln Ile Leu Ser Ile Tyr Ser Thr Val Ala Ser Ser Leu Ala
        515                 520                 525

Leu Ala Ile Met Val Ala Gly Leu Ser Leu Trp Met Cys Ser Asn Gly
    530                 535                 540

Ser Leu Gln Cys Arg Ile Cys Ile
545                 550


<210> SEQ ID NO 3
<211> LENGTH: 97
<212> TYPE: PRT
<213> ORGANISM: Influenza A virus

<400> SEQUENCE: 3

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Leu His Leu Ile Leu Trp Ile Leu Asp Arg Leu Phe Phe
        35                  40                  45

Lys Cys Ile Tyr Arg Phe Phe Glu His Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Ser Ala Val Asp Ala Asp Asp Ser His Phe Val Ser Ile Glu Leu
                85                  90                  95

Glu
```

```
<210> SEQ ID NO 4
<211> LENGTH: 566
<212> TYPE: PRT
<213> ORGANISM: Influenza A virus

<400> SEQUENCE: 4

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Ile His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380
```

-continued

```
Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Glu Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Ile
                565
```

<210> SEQ ID NO 5
<211> LENGTH: 186
<212> TYPE: DNA
<213> ORGANISM: Influenza A virus

<400> SEQUENCE: 5

```
aaaagttctt ggtccaatca tgatgcctca tcaggggtga gctcagcatg tccatacctt     60

gggaggtcct cctttttcag aaatgtggta tggcttatca aaaagaacag tgcataccca    120

acagctacta gacccaaagt aaacgggcaa agtggaagaa tggagttctt ctggacaatt    180

ttaaag                                                               186
```

<210> SEQ ID NO 6
<211> LENGTH: 71
<212> TYPE: DNA
<213> ORGANISM: Influenza A virus

<400> SEQUENCE: 6

```
atgagccttc taaccgaggt tgacacgctt accagaaacg gatgggggtg cgatgcagcg     60

attcaagtga t                                                          71
```

<210> SEQ ID NO 7
<211> LENGTH: 450
<212> TYPE: PRT
<213> ORGANISM: Influenza A virus
<220> FEATURE:
<221> NAME/KEY: MOD_RES
<222> LOCATION: (370)
<223> OTHER INFORMATION: variable amino acid

<400> SEQUENCE: 7

```
Met Asn Pro Asn Gln Lys Ile Ile Thr Ile Gly Ser Ile Cys Met Val
1               5                   10                  15
```

-continued

```
Val Gly Ile Ile Ser Leu Met Leu Gln Ile Gly Asn Ile Ile Ser Val
            20                  25                  30

Trp Val Ser His Ile Ile Gln Thr Trp His Pro Asn Gln Pro Glu Pro
        35                  40                  45

Cys Asn Gln Ser Ile Asn Phe Tyr Thr Glu Gln Ala Ala Ala Ser Val
    50                  55                  60

Thr Leu Ala Gly Asn Ser Ser Leu Cys Pro Ile Ser Gly Trp Ala Ile
65                  70                  75                  80

Tyr Ser Lys Asp Asn Ser Ile Arg Ile Gly Ser Lys Gly Asp Val Phe
                85                  90                  95

Val Ile Arg Glu Pro Phe Ile Ser Cys Ser His Leu Glu Cys Arg Thr
            100                 105                 110

Phe Phe Leu Thr Gln Gly Ala Leu Leu Asn Asp Lys His Ser Asn Gly
        115                 120                 125

Thr Val Lys Asp Arg Ser Pro Tyr Arg Thr Leu Met Ser Cys Pro Val
    130                 135                 140

Gly Glu Ala Pro Ser Pro Tyr Asn Ser Arg Phe Glu Ser Val Ala Trp
145                 150                 155                 160

Ser Ala Ser Ala Cys His Asp Gly Ile Ser Trp Leu Thr Ile Gly Ile
                165                 170                 175

Ser Gly Pro Asp Asn Gly Ala Val Ala Val Leu Lys Tyr Asn Gly Ile
            180                 185                 190

Ile Thr Asp Thr Ile Lys Ser Trp Arg Asn Asn Ile Leu Arg Thr Gln
        195                 200                 205

Glu Ser Glu Cys Ala Cys Val Asn Gly Ser Cys Phe Thr Val Met Thr
    210                 215                 220

Asp Gly Pro Ser Asn Glu Gln Ala Ser Tyr Lys Ile Phe Lys Ile Glu
225                 230                 235                 240

Lys Gly Arg Val Val Lys Ser Val Glu Leu Asn Ala Pro Asn Tyr His
                245                 250                 255

Tyr Glu Glu Cys Ser Cys Tyr Pro Asp Ala Gly Glu Ile Thr Cys Val
            260                 265                 270

Cys Arg Asp Asn Trp His Gly Ser Asn Arg Pro Trp Val Ser Phe Asn
        275                 280                 285

Gln Asn Leu Glu Tyr Gln Ile Gly Tyr Ile Cys Ser Gly Val Phe Gly
    290                 295                 300

Asp Ser Pro Arg Pro Asn Asp Gly Thr Gly Ser Cys Gly Pro Val Ser
305                 310                 315                 320

Leu Asn Gly Ala Tyr Gly Val Lys Gly Phe Ser Phe Lys Tyr Gly Asn
                325                 330                 335

Gly Val Trp Ile Gly Arg Thr Lys Ser Thr Ser Ser Arg Ser Gly Phe
            340                 345                 350

Glu Met Ile Trp Asp Pro Asn Gly Trp Thr Glu Thr Asp Ser Ser Phe
        355                 360                 365

Ser Xaa Lys Gln Asp Ile Ile Ala Ile Thr Asp Trp Ser Gly Tyr Ser
    370                 375                 380

Gly Ser Phe Ile Gln His Pro Glu Leu Thr Gly Leu Asn Cys Met Arg
385                 390                 395                 400

Pro Cys Phe Trp Val Glu Leu Ile Arg Gly Arg Pro Lys Glu Lys Thr
                405                 410                 415

Ile Trp Thr Ser Gly Ser Ser Ile Ser Phe Cys Gly Val Asn Ser Asp
            420                 425                 430

Thr Val Gly Trp Ser Trp Pro Asp Gly Ala Asp Leu Pro Phe Thr Ile
```

-continued 435 440 445

Asp Lys
450

<210> SEQ ID NO 8
<211> LENGTH: 1388
<212> TYPE: DNA
<213> ORGANISM: Influenza A virus
<220> FEATURE:
<221> NAME/KEY: modified_base
<222> LOCATION: (1128)
<223> OTHER INFORMATION: a, c, g, t, unknown or other

<400> SEQUENCE: 8
agcaaaagca ggagtttaaa atgaatccaa atcagaagat aataaccatt ggatcaatct 60
gtatggtagt tgggataatc agcttgatgt tacaaattgg aaacataata tcagtatggg 120
tcagccacat aattcaaact tggcacccaa accagcctga accatgcaat caaagcatca 180
atttttacac tgagcaggct gcagcttcag tgacattagc gggcaattcc tctctctgcc 240
ctattagtgg atgggctata tacagcaagg acaatagtat aagaattggt tccaaagggg 300
atgtgtttgt tataagagaa ccattcatct catgttccca tttggaatgc agaacctttt 360
tcttgaccca aggagcccta ttgaatgaca agcattctaa tgggaccgtc aaagacagga 420
gcccctatag aactttaatg agctgtcctg ttggtgaggc tccttcccca tacaactcaa 480
ggtttgagtc tgttgcttgg tcggcaagtg cttgccatga tggcattagt tggctaacaa 540
ttggaatttc cggtccggat aatggggctg tggctgtgtt gaaatacaat ggcataataa 600
cagacaccat caagagttgg aggaacaaca tactgaggac gcaagagtct gaatgtgcat 660
gtgtgaatgg ttcttgtttt actgtaatga cagatggacc gagtaatgaa caggcctcat 720
acaagatttt caagatagaa aaggggaggg tagtcaaatc agttgagttg aacgccccta 780
attatcatta cgaggaatgc tcctgttatc ctgatgctgg cgaaatcaca tgtgtgtgca 840
gggataattg gcatggctcg aaccgaccat gggtgtcttt caatcagaat ctggagtatc 900
aaataggata tatatgcagt ggggttttcg gagacagtcc acgccccaat gatgggacag 960
gcagttgtgg tccagtgtct cttaacggag cgtatggagt aaaagggttt tcatttaaat 1020
acggcaatgg tgtttggatc gggagaacca aaagcactag ttccaggagc ggttttgaaa 1080
tgatttggga tccaaatggg tggaccgaaa cagacagtag cttctcgntg aagcaagaca 1140
tcatagcaat aactgattgg tcaggataca gcgggagttt tattcaacat ccagaactga 1200
caggattaaa ttgcatgaga ccttgcttct gggttgaact aatcagaggg aggcccaaag 1260
agaaaacaat ctggactagt gggagcagta tatctttctg tggtgtaaat agtgacactg 1320
tgggttggtc ttggccagac ggtgctgatt tgccattcac cattgacaag tagttsgttc 1380
aaaaaact 1388

<210> SEQ ID NO 9
<211> LENGTH: 568
<212> TYPE: PRT
<213> ORGANISM: Influenza A virus

<400> SEQUENCE: 9

Met Glu Arg Thr Val Leu Leu Leu Ala Thr Val Ser Leu Val Lys Ser
1 5 10 15

Asp Gln Ile Cys Ile Gly Tyr His Ala Asn Asn Ser Thr Glu Gln Val
20 25 30

-continued

```
Asp Thr Ile Met Glu Lys Asn Val Thr Val Thr His Ala Gln Asp Ile
        35                  40                  45

Leu Glu Arg Thr His Asn Gly Lys Leu Cys Asp Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Ser Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asn His Asp Ala Ser
    130                 135                 140

Ser Gly Val Ser Ser Ala Cys Pro Tyr Leu Gly Arg Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
            180                 185                 190

Gly Val His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Thr
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Cys Tyr Ser Ala Asp Lys
    370                 375                 380

Glu Ser Thr Gln Lys Ala Ile Asp Gly Val Thr Asn Lys Val Asn Ser
385                 390                 395                 400

Ile Ile Asn Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
```

```
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Lys Asn Gly Thr Tyr Asp Tyr Pro Gln Tyr Ser Glu Glu Ala
            500                 505                 510

Arg Leu Asn Arg Glu Glu Ile Ser Gly Val Lys Leu Glu Ser Met Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565


<210> SEQ ID NO 10
<211> LENGTH: 566
<212> TYPE: PRT
<213> ORGANISM: Influenza A virus

<400> SEQUENCE: 10

Met Lys Thr Ile Ile Ala Leu Ser Tyr Ile Phe Cys Leu Val Phe Ala
1               5                   10                  15

Gln Asp Leu Pro Gly Asn Asp Asn Asn Ser Thr Ala Thr Leu Cys Leu
            20                  25                  30

Gly His His Ala Val Pro Asn Gly Thr Leu Val Lys Thr Ile Thr Asn
        35                  40                  45

Asp Gln Ile Glu Val Thr Asn Ala Thr Glu Leu Val Gln Ser Ser Ser
    50                  55                  60

Thr Gly Lys Ile Cys Asn Asn Pro His Arg Ile Leu Asp Gly Ile Asn
65                  70                  75                  80

Cys Thr Leu Ile Asp Ala Leu Leu Gly Asp Pro His Cys Asp Gly Phe
                85                  90                  95

Gln Asn Glu Lys Trp Asp Leu Phe Val Glu Arg Ser Lys Ala Phe Ser
            100                 105                 110

Asn Cys Tyr Pro Tyr Asp Val Pro Asp Tyr Ala Ser Leu Arg Ser Leu
        115                 120                 125

Val Ala Ser Ser Gly Thr Leu Glu Phe Ile Asn Glu Gly Phe Asn Trp
    130                 135                 140

Thr Gly Val Thr Gln Asn Gly Gly Ser Ser Ala Cys Lys Arg Gly Pro
145                 150                 155                 160

Asp Ser Gly Phe Phe Ser Arg Leu Asn Trp Leu Tyr Lys Ser Gly Ser
                165                 170                 175

Thr Tyr Pro Val Gln Asn Val Thr Met Pro Asn Asn Asp Asn Ser Asp
            180                 185                 190

Lys Leu Tyr Ile Trp Gly Val His His Pro Ser Thr Asp Lys Glu Gln
        195                 200                 205

Thr Asn Leu Tyr Val Gln Ala Ser Gly Lys Val Thr Val Ser Thr Lys
    210                 215                 220

Arg Ser Gln Gln Thr Ile Ile Pro Asn Val Gly Ser Arg Pro Trp Val
225                 230                 235                 240

Arg Gly Leu Ser Ser Arg Ile Ser Ile Tyr Trp Thr Ile Val Lys Pro
                245                 250                 255
```

-continued

```
Gly Asp Ile Leu Val Ile Asn Ser Asn Gly Asn Leu Ile Ala Pro Arg
            260                 265                 270

Gly Tyr Phe Lys Met Arg Thr Gly Lys Ser Ser Ile Met Arg Ser Asp
        275                 280                 285

Ala Pro Ile Gly Thr Cys Ser Ser Glu Cys Ile Thr Pro Asn Gly Ser
    290                 295                 300

Ile Pro Asn Asp Lys Pro Phe Gln Asn Val Asn Lys Ile Thr Tyr Gly
305                 310                 315                 320

Ala Cys Pro Lys Tyr Val Lys Gln Asn Thr Leu Lys Leu Ala Thr Gly
                325                 330                 335

Met Arg Asn Val Pro Glu Lys Gln Thr Arg Gly Ile Phe Gly Ala Ile
            340                 345                 350

Ala Gly Phe Ile Glu Asn Gly Trp Glu Gly Met Ile Asp Gly Trp Tyr
        355                 360                 365

Gly Phe Arg His Gln Asn Ser Glu Gly Thr Gly Gln Ala Ala Asp Leu
    370                 375                 380

Lys Ser Thr Gln Ala Ala Ile Asp Gln Ile Asn Gly Lys Leu Asn Arg
385                 390                 395                 400

Val Ile Glu Lys Thr Asn Glu Lys Phe His Gln Ile Glu Lys Glu Phe
                405                 410                 415

Ser Glu Val Glu Gly Arg Ile Gln Asp Leu Glu Lys Tyr Val Glu Asp
            420                 425                 430

Thr Lys Ile Asp Leu Trp Ser Tyr Asn Ala Glu Leu Leu Val Ala Leu
        435                 440                 445

Glu Asn Gln His Thr Ile Asp Leu Thr Asp Ser Glu Met Asn Lys Leu
    450                 455                 460

Phe Glu Lys Thr Arg Arg Gln Leu Arg Glu Asn Ala Glu Asp Met Gly
465                 470                 475                 480

Asn Gly Cys Phe Lys Ile Tyr His Lys Cys Asp Asn Ala Cys Ile Gly
                485                 490                 495

Ser Ile Arg Asn Gly Thr Tyr Asp His Asp Val Tyr Arg Asp Glu Ala
            500                 505                 510

Leu Asn Asn Arg Phe Gln Ile Lys Gly Val Glu Leu Lys Ser Gly Tyr
        515                 520                 525

Lys Asp Trp Ile Leu Trp Ile Ser Phe Ala Ile Ser Cys Phe Leu Leu
    530                 535                 540

Cys Val Val Leu Leu Gly Phe Ile Met Trp Ala Cys Gln Lys Gly Asn
545                 550                 555                 560

Ile Arg Cys Asn Ile Cys
                565


<210> SEQ ID NO 11
<211> LENGTH: 469
<212> TYPE: PRT
<213> ORGANISM: Influenza A virus

<400> SEQUENCE: 11

Met Asn Pro Asn Gln Lys Ile Ile Thr Ile Gly Ser Val Ser Leu Thr
1               5                   10                  15

Ile Ala Thr Ile Cys Phe Leu Met Gln Ile Ala Ile Leu Val Thr Thr
            20                  25                  30

Val Thr Leu His Phe Lys Gln Tyr Glu Cys Ser Ser Pro Pro Asn Asn
        35                  40                  45

Gln Val Met Leu Cys Glu Pro Thr Ile Ile Glu Arg Asn Ile Thr Glu
    50                  55                  60
```

-continued

```
Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Lys Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Arg His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly His Asp Glu Asn Ala Thr Ala Ser Phe Ile Tyr Asp
        195                 200                 205

Gly Arg Leu Val Asp Ser Ile Gly Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Lys Ile Leu Phe
                245                 250                 255

Ile Glu Glu Gly Lys Ile Val His Ile Ser Pro Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asn Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Phe Arg Ser Gly Tyr Glu Thr Phe Lys Val Ile Glu Gly Trp Ser
    370                 375                 380

Lys Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Glu Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465
```

-continued

<210> SEQ ID NO 12
<211> LENGTH: 136
<212> TYPE: PRT
<213> ORGANISM: Influenza A virus

<400> SEQUENCE: 12

```
Asn His Phe Glu Lys Ile Gln Ile Ile Pro Lys Ser Ser Trp Ser Asn
1               5                   10                  15

His Asp Ala Ser Ser Gly Val Ser Ser Ala Cys Pro Tyr Leu Gly Arg
            20                  25                  30

Ser Ser Phe Phe Arg Asn Val Val Trp Leu Ile Lys Lys Asn Ser Ala
        35                  40                  45

Tyr Pro Thr Ile Lys Arg Ser Tyr Asn Asn Thr Asn Gln Glu Asp Leu
    50                  55                  60

Leu Val Leu Trp Gly Val His His Pro Asn Asp Ala Ala Glu Gln Thr
65                  70                  75                  80

Lys Leu Tyr Gln Asn Pro Thr Thr Tyr Ile Ser Val Gly Thr Ser Thr
                85                  90                  95

Leu Asn Gln Arg Leu Val Pro Glu Ile Ala Thr Arg Pro Lys Val Asn
            100                 105                 110

Gly Gln Ser Gly Arg Met Glu Phe Phe Trp Thr Ile Leu Lys Pro Asn
        115                 120                 125

Asp Ala Ile Asn Phe Glu Ser Asn
    130                 135
```

<210> SEQ ID NO 13
<211> LENGTH: 61
<212> TYPE: PRT
<213> ORGANISM: Influenza A virus

<400> SEQUENCE: 13

```
Asn His Phe Glu Lys Ile Gln Ile Ile Pro Lys Ser Ser Trp Ser Asn
1               5                   10                  15

His Asp Ala Ser Ser Gly Val Ser Ser Ala Cys Pro Tyr Leu Gly Arg
            20                  25                  30

Ser Ser Phe Phe Arg Asn Val Val Trp Leu Ile Lys Lys Asn Ser Ala
        35                  40                  45

Tyr Pro Thr Ile Lys Arg Ser Tyr Asn Asn Thr Asn Gln
    50                  55                  60
```

<210> SEQ ID NO 14
<211> LENGTH: 51
<212> TYPE: PRT
<213> ORGANISM: Influenza A virus

<400> SEQUENCE: 14

```
Ile Gln Ile Ile Pro Lys Ser Ser Trp Ser Asn His Asp Ala Ser Ser
1               5                   10                  15

Gly Val Ser Ser Ala Cys Pro Tyr Leu Gly Arg Ser Ser Phe Phe Arg
            20                  25                  30

Asn Val Val Trp Leu Ile Lys Lys Asn Ser Ala Tyr Pro Thr Ile Lys
        35                  40                  45

Arg Ser Tyr
    50
```

<210> SEQ ID NO 15
<211> LENGTH: 41
<212> TYPE: PRT

-continued

<213> ORGANISM: Influenza A virus

<400> SEQUENCE: 15

Lys Ser Ser Trp Ser Asn His Asp Ala Ser Ser Gly Val Ser Ser Ala
1 5 10 15

Cys Pro Tyr Leu Gly Arg Ser Ser Phe Phe Arg Asn Val Val Trp Leu
20 25 30

Ile Lys Lys Asn Ser Ala Tyr Pro Thr
35 40

<210> SEQ ID NO 16
<211> LENGTH: 41
<212> TYPE: PRT
<213> ORGANISM: Influenza A virus

<400> SEQUENCE: 16

Thr Leu Asn Gln Arg Leu Val Pro Glu Ile Ala Thr Arg Pro Lys Val
1 5 10 15

Asn Gly Gln Ser Gly Arg Met Glu Phe Phe Trp Thr Ile Leu Lys Pro
20 25 30

Asn Asp Ala Ile Asn Phe Glu Ser Asn
35 40

<210> SEQ ID NO 17
<211> LENGTH: 31
<212> TYPE: PRT
<213> ORGANISM: Influenza A virus

<400> SEQUENCE: 17

Leu Val Pro Glu Ile Ala Thr Arg Pro Lys Val Asn Gly Gln Ser Gly
1 5 10 15

Arg Met Glu Phe Phe Trp Thr Ile Leu Lys Pro Asn Asp Ala Ile
20 25 30

<210> SEQ ID NO 18
<211> LENGTH: 21
<212> TYPE: PRT
<213> ORGANISM: Influenza A virus

<400> SEQUENCE: 18

Ala Thr Arg Pro Lys Val Asn Gly Gln Ser Gly Arg Met Glu Phe Phe
1 5 10 15

Trp Thr Ile Leu Lys
20

<210> SEQ ID NO 19
<211> LENGTH: 5
<212> TYPE: PRT
<213> ORGANISM: Influenza A virus

<400> SEQUENCE: 19

Ser Gly Val Ser Ser
1 5

<210> SEQ ID NO 20
<211> LENGTH: 5
<212> TYPE: PRT
<213> ORGANISM: Influenza A virus

<400> SEQUENCE: 20

Asn Gly Gln Ser Gly
1 5

```
<210> SEQ ID NO 21
<211> LENGTH: 62
<212> TYPE: PRT
<213> ORGANISM: Influenza A virus

<400> SEQUENCE: 21

Lys Ser Ser Trp Ser Asn His Asp Ala Ser Ser Gly Val Ser Ser Ala
1               5                   10                  15

Cys Pro Tyr Leu Gly Arg Ser Ser Phe Phe Arg Asn Val Val Trp Leu
            20                  25                  30

Ile Lys Lys Asn Ser Ala Tyr Pro Thr Ala Thr Arg Pro Lys Val Asn
        35                  40                  45

Gly Gln Ser Gly Arg Met Glu Phe Phe Trp Thr Ile Leu Lys
    50                  55                  60


<210> SEQ ID NO 22
<211> LENGTH: 232
<212> TYPE: PRT
<213> ORGANISM: Influenza A virus

<400> SEQUENCE: 22

Thr Ile Thr Asn Asp Gln Ile Glu Val Thr Asn Ala Thr Glu Leu Val
1               5                   10                  15

Gln Ser Ser Ser Thr Gly Lys Ile Cys Asn Asn Pro His Arg Ile Leu
            20                  25                  30

Asp Gly Ile Asn Cys Thr Leu Ile Asp Ala Leu Leu Gly Asp Pro His
        35                  40                  45

Cys Asp Gly Phe Gln Asn Glu Lys Trp Asp Leu Phe Val Glu Arg Ser
    50                  55                  60

Lys Ala Phe Ser Asn Cys Tyr Pro Tyr Asp Val Pro Asp Tyr Ala Ser
65                  70                  75                  80

Leu Arg Ser Leu Val Ala Ser Ser Gly Thr Leu Glu Phe Ile Asn Glu
                85                  90                  95

Gly Phe Asn Trp Thr Gly Val Thr Gln Asn Gly Gly Ser Ser Ala Cys
            100                 105                 110

Lys Arg Gly Pro Asp Ser Gly Phe Phe Ser Arg Leu Asn Trp Leu Tyr
        115                 120                 125

Lys Ser Gly Ser Thr Tyr Pro Val Gln Asn Val Thr Met Pro Asn Asn
    130                 135                 140

Asp Asn Ser Asp Lys Leu Tyr Ile Trp Gly Val His His Pro Ser Thr
145                 150                 155                 160

Asp Lys Glu Gln Thr Asn Leu Tyr Val Gln Ala Ser Gly Lys Val Thr
                165                 170                 175

Val Ser Thr Lys Arg Ser Gln Gln Thr Ile Ile Pro Asn Val Gly Ser
            180                 185                 190

Arg Pro Trp Val Arg Gly Leu Ser Ser Arg Ile Ser Ile Tyr Trp Thr
        195                 200                 205

Ile Val Lys Pro Gly Asp Ile Leu Val Ile Asn Ser Asn Gly Asn Leu
    210                 215                 220

Ile Ala Pro Arg Gly Tyr Phe Lys
225                 230


<210> SEQ ID NO 23
<211> LENGTH: 9
<212> TYPE: PRT
<213> ORGANISM: Influenza A virus
```

<400> SEQUENCE: 23

Thr Ile Thr Asn Asp Gln Ile Glu Val
1 5

<210> SEQ ID NO 24
<211> LENGTH: 12
<212> TYPE: PRT
<213> ORGANISM: Influenza A virus

<400> SEQUENCE: 24

Ile Leu Asp Gly Ile Asn Cys Thr Leu Ile Asp Ala
1 5 10

<210> SEQ ID NO 25
<211> LENGTH: 9
<212> TYPE: PRT
<213> ORGANISM: Influenza A virus

<400> SEQUENCE: 25

Leu Phe Val Glu Arg Ser Lys Ala Phe
1 5

<210> SEQ ID NO 26
<211> LENGTH: 18
<212> TYPE: PRT
<213> ORGANISM: Influenza A virus

<400> SEQUENCE: 26

Pro Tyr Asp Val Pro Asp Tyr Ala Ser Leu Arg Ser Leu Val Ala Ser
1 5 10 15

Ser Gly

<210> SEQ ID NO 27
<211> LENGTH: 9
<212> TYPE: PRT
<213> ORGANISM: Influenza A virus

<400> SEQUENCE: 27

Trp Leu Tyr Lys Ser Gly Ser Thr Tyr
1 5

<210> SEQ ID NO 28
<211> LENGTH: 9
<212> TYPE: PRT
<213> ORGANISM: Influenza A virus

<400> SEQUENCE: 28

Asn Asn Asp Asn Ser Asp Lys Leu Tyr
1 5

<210> SEQ ID NO 29
<211> LENGTH: 10
<212> TYPE: PRT
<213> ORGANISM: Influenza A virus

<400> SEQUENCE: 29

Ser Thr Asp Lys Glu Gln Thr Asn Leu Tyr
1 5 10

<210> SEQ ID NO 30
<211> LENGTH: 15
<212> TYPE: PRT
<213> ORGANISM: Influenza A virus

<400> SEQUENCE: 30

Thr Glu Leu Val Gln Ser Ser Ser Thr Gly Lys Ile Cys Asn Asn
1               5                   10                  15

<210> SEQ ID NO 31
<211> LENGTH: 15
<212> TYPE: PRT
<213> ORGANISM: Influenza A virus

<400> SEQUENCE: 31

Pro His Arg Ile Leu Asp Gly Ile Asn Cys Thr Leu Ile Asp Ala
1               5                   10                  15

<210> SEQ ID NO 32
<211> LENGTH: 15
<212> TYPE: PRT
<213> ORGANISM: Influenza A virus

<400> SEQUENCE: 32

Val Pro Asp Tyr Ala Ser Leu Arg Ser Leu Val Ala Ser Ser Gly
1               5                   10                  15

<210> SEQ ID NO 33
<211> LENGTH: 6
<212> TYPE: PRT
<213> ORGANISM: Influenza A virus

<400> SEQUENCE: 33

Glu Phe Ile Asn Glu Gly
1               5

<210> SEQ ID NO 34
<211> LENGTH: 14
<212> TYPE: PRT
<213> ORGANISM: Influenza A virus

<400> SEQUENCE: 34

Lys Ala Phe Ser Asn Cys Tyr Pro Tyr Asp Val Pro Asp Tyr
1               5                   10

<210> SEQ ID NO 35
<211> LENGTH: 379
<212> TYPE: PRT
<213> ORGANISM: Influenza A virus

<400> SEQUENCE: 35

Gln Cys Lys Ile Thr Gly Phe Ala Pro Phe Ser Lys Asp Asn Ser Ile
1               5                   10                  15

Arg Leu Ser Ala Gly Gly Asp Ile Trp Val Thr Arg Glu Pro Tyr Val
            20                  25                  30

Ser Cys Asp Pro Asp Lys Cys Tyr Gln Phe Ala Leu Gly Gln Gly Thr
        35                  40                  45

Thr Leu Asn Asn Arg His Ser Asn Asp Thr Val His Asp Arg Thr Pro
    50                  55                  60

Tyr Arg Thr Leu Leu Met Asn Glu Leu Gly Val Pro Phe His Leu Gly
65                  70                  75                  80

Thr Lys Gln Val Cys Ile Ala Trp Ser Ser Ser Ser Cys His Asp Gly
                85                  90                  95

Lys Ala Trp Leu His Val Cys Val Thr Gly His Asp Glu Asn Ala Thr
            100                 105                 110

```
Ala Ser Phe Ile Tyr Asp Gly Arg Leu Val Asp Ser Ile Gly Ser Trp
        115                 120                 125

Ser Lys Lys Ile Leu Arg Thr Gln Glu Ser Glu Cys Val Cys Ile Asn
    130                 135                 140

Gly Thr Cys Thr Val Val Met Thr Asp Gly Ser Ala Ser Gly Arg Ala
145                 150                 155                 160

Asp Thr Lys Ile Leu Phe Ile Glu Glu Gly Lys Ile Val His Ile Ser
                165                 170                 175

Pro Leu Ser Gly Ser Ala Gln His Val Glu Glu Cys Ser Cys Tyr Pro
            180                 185                 190

Arg Tyr Pro Gly Val Arg Cys Val Cys Arg Asp Asn Trp Lys Gly Ser
        195                 200                 205

Asn Arg Pro Ile Val Asp Ile Asn Val Lys Asp Tyr Ser Ile Val Ser
    210                 215                 220

Ser Tyr Val Cys Ser Gly Leu Val Gly Asp Thr Pro Arg Lys Asn Asp
225                 230                 235                 240

Ser Ser Ser Ser Ser His Cys Leu Asn Pro Asn Asn Glu Glu Gly Gly
                245                 250                 255

His Gly Val Lys Gly Trp Ala Phe Asp Asp Gly Asn Asp Val Trp Met
            260                 265                 270

Gly Arg Thr Ile Ser Glu Lys Phe Arg Ser Gly Tyr Glu Thr Phe Lys
        275                 280                 285

Val Ile Glu Gly Trp Ser Lys Pro Asn Ser Lys Leu Gln Ile Asn Arg
    290                 295                 300

Gln Val Ile Val Asp Arg Gly Asn Arg Ser Gly Tyr Ser Gly Ile Phe
305                 310                 315                 320

Ser Val Glu Gly Lys Ser Cys Ile Asn Arg Cys Phe Tyr Val Glu Leu
                325                 330                 335

Ile Arg Gly Arg Lys Gln Glu Thr Glu Val Trp Trp Thr Ser Asn Ser
            340                 345                 350

Ile Val Val Phe Cys Gly Thr Ser Gly Thr Tyr Gly Thr Gly Ser Trp
        355                 360                 365

Pro Asp Gly Ala Asp Ile Asn Leu Met Pro Ile
    370                 375


<210> SEQ ID NO 36
<211> LENGTH: 44
<212> TYPE: PRT
<213> ORGANISM: Influenza A virus

<400> SEQUENCE: 36

Ala Trp Leu His Val Cys Val Thr Gly His Asp Glu Asn Ala Thr Ala
1               5                   10                  15

Ser Phe Ile Tyr Asp Gly Arg Leu Val Asp Ser Ile Gly Ser Trp Ser
            20                  25                  30

Lys Lys Ile Leu Arg Thr Gln Glu Ser Glu Cys Val
        35                  40


<210> SEQ ID NO 37
<211> LENGTH: 34
<212> TYPE: PRT
<213> ORGANISM: Influenza A virus

<400> SEQUENCE: 37

Cys Val Thr Gly His Asp Glu Asn Ala Thr Ala Ser Phe Ile Tyr Asp
1               5                   10                  15
```

-continued

```
Gly Arg Leu Val Asp Ser Ile Gly Ser Trp Ser Lys Lys Ile Leu Arg
            20                  25                  30

Thr Gln


<210> SEQ ID NO 38
<211> LENGTH: 24
<212> TYPE: PRT
<213> ORGANISM: Influenza A virus

<400> SEQUENCE: 38

Asp Glu Asn Ala Thr Ala Ser Phe Ile Tyr Asp Gly Arg Leu Val Asp
1               5                   10                  15

Ser Ile Gly Ser Trp Ser Lys Lys
            20


<210> SEQ ID NO 39
<211> LENGTH: 24
<212> TYPE: PRT
<213> ORGANISM: Influenza A virus

<400> SEQUENCE: 39

Met Ser Leu Leu Thr Glu Val Asp Thr Leu Thr Arg Asn Gly Trp Gly
1               5                   10                  15

Cys Arg Cys Ser Asp Ser Ser Asp
            20


<210> SEQ ID NO 40
<211> LENGTH: 72
<212> TYPE: DNA
<213> ORGANISM: Influenza A virus

<400> SEQUENCE: 40

atgagccttc taaccgaggt tgacacgctt accagaaacg gatgggggtg cagatgcagc     60

gattcaagtg at                                                         72


<210> SEQ ID NO 41
<211> LENGTH: 72
<212> TYPE: DNA
<213> ORGANISM: Influenza A virus

<400> SEQUENCE: 41

atgagccttc taaccgaggt cgaaacacct atcagaaacg aatgggggtg cagatgcaac     60

gattcaagtg ac                                                         72


<210> SEQ ID NO 42
<211> LENGTH: 24
<212> TYPE: PRT
<213> ORGANISM: Influenza A virus

<400> SEQUENCE: 42

Met Ser Leu Leu Thr Glu Val Glu Thr Pro Ile Arg Asn Glu Trp Gly
1               5                   10                  15

Cys Arg Cys Asn Asp Ser Ser Asp
            20


<210> SEQ ID NO 43
<211> LENGTH: 264
<212> TYPE: DNA
<213> ORGANISM: Artificial Sequence
<220> FEATURE:
<223> OTHER INFORMATION: Description of Artificial Sequence: Synthetic
      construct
```

<400> SEQUENCE: 43
aaaagttctt ggtccaatca tgatgcctca tcaggggtga gctcagcatg tccatacctt 60
gggaggtcct cctttttcag aaatgtggta tggcttatca aaaagaacag tgcataccca 120
acagctacta gacccaaagt aaacgggcaa agtggaagaa tggagttctt ctggacaatt 180
ttaaaggata tcatgagcct tctaaccgag gttgacacgc ttaccagaaa cggatggggg 240
tgcagatgca gcgattcaag tgat 264

<210> SEQ ID NO 44
<211> LENGTH: 258
<212> TYPE: DNA
<213> ORGANISM: Artificial Sequence
<220> FEATURE:
<223> OTHER INFORMATION: Description of Artificial Sequence: Synthetic construct

<400> SEQUENCE: 44
atgagccttc taaccgaggt tgacacgctt accagaaacg gatgggggtg cagatgcagc 60
gattcaagtg ataaaagttc ttggtccaat catgatgcct catcaggggt gagctcagca 120
tgtccatacc ttgggaggtc ctcctttttc agaaatgtgg tatggcttat caaaaagaac 180
agtgcatacc caacagctac tagacccaaa gtaaacgggc aaagtggaag aatggagttc 240
ttctggacaa ttttaaag 258

<210> SEQ ID NO 45
<211> LENGTH: 256
<212> TYPE: PRT
<213> ORGANISM: Artificial Sequence
<220> FEATURE:
<223> OTHER INFORMATION: Description of Artificial Sequence: Synthetic construct

<400> SEQUENCE: 45

Thr Ile Thr Asn Asp Gln Ile Glu Val Thr Asn Ala Thr Glu Leu Val
1 5 10 15

Gln Ser Ser Ser Thr Gly Lys Ile Cys Asn Asn Pro His Arg Ile Leu
20 25 30

Asp Gly Ile Asn Cys Thr Leu Ile Asp Ala Leu Leu Gly Asp Pro His
35 40 45

Cys Asp Gly Phe Gln Asn Glu Lys Trp Asp Leu Phe Val Glu Arg Ser
50 55 60

Lys Ala Phe Ser Asn Cys Tyr Pro Tyr Asp Val Pro Asp Tyr Ala Ser
65 70 75 80

Leu Arg Ser Leu Val Ala Ser Ser Gly Thr Leu Glu Phe Ile Asn Glu
85 90 95

Gly Phe Asn Trp Thr Gly Val Thr Gln Asn Gly Gly Ser Ser Ala Cys
100 105 110

Lys Arg Gly Pro Asp Ser Gly Phe Phe Ser Arg Leu Asn Trp Leu Tyr
115 120 125

Lys Ser Gly Ser Thr Tyr Pro Val Gln Asn Val Thr Met Pro Asn Asn
130 135 140

Asp Asn Ser Asp Lys Leu Tyr Ile Trp Gly Val His His Pro Ser Thr
145 150 155 160

Asp Lys Glu Gln Thr Asn Leu Tyr Val Gln Ala Ser Gly Lys Val Thr
165 170 175

Val Ser Thr Lys Arg Ser Gln Gln Thr Ile Ile Pro Asn Val Gly Ser

-continued

```
            180                 185                 190

Arg Pro Trp Val Arg Gly Leu Ser Ser Arg Ile Ser Ile Tyr Trp Thr
        195                 200                 205

Ile Val Lys Pro Gly Asp Ile Leu Val Ile Asn Ser Asn Gly Asn Leu
    210                 215                 220

Ile Ala Pro Arg Gly Tyr Phe Lys Met Ser Leu Leu Thr Glu Val Glu
225                 230                 235                 240

Thr Pro Ile Arg Asn Glu Trp Gly Cys Arg Cys Asn Asp Ser Ser Asp
                245                 250                 255


<210> SEQ ID NO 46
<211> LENGTH: 403
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 46

Gln Cys Lys Ile Thr Gly Phe Ala Pro Phe Ser Lys Asp Asn Ser Ile
1               5                   10                  15

Arg Leu Ser Ala Gly Gly Asp Ile Trp Val Thr Arg Glu Pro Tyr Val
            20                  25                  30

Ser Cys Asp Pro Asp Lys Cys Tyr Gln Phe Ala Leu Gly Gln Gly Thr
        35                  40                  45

Thr Leu Asn Asn Arg His Ser Asn Asp Thr Val His Asp Arg Thr Pro
    50                  55                  60

Tyr Arg Thr Leu Leu Met Asn Glu Leu Gly Val Pro Phe His Leu Gly
65                  70                  75                  80

Thr Lys Gln Val Cys Ile Ala Trp Ser Ser Ser Ser Cys His Asp Gly
                85                  90                  95

Lys Ala Trp Leu His Val Cys Val Thr Gly His Asp Glu Asn Ala Thr
            100                 105                 110

Ala Ser Phe Ile Tyr Asp Gly Arg Leu Val Asp Ser Ile Gly Ser Trp
        115                 120                 125

Ser Lys Lys Ile Leu Arg Thr Gln Glu Ser Glu Cys Val Cys Ile Asn
    130                 135                 140

Gly Thr Cys Thr Val Val Met Thr Asp Gly Ser Ala Ser Gly Arg Ala
145                 150                 155                 160

Asp Thr Lys Ile Leu Phe Ile Glu Glu Gly Lys Ile Val His Ile Ser
                165                 170                 175

Pro Leu Ser Gly Ser Ala Gln His Val Glu Glu Cys Ser Cys Tyr Pro
            180                 185                 190

Arg Tyr Pro Gly Val Arg Cys Val Cys Arg Asp Asn Trp Lys Gly Ser
        195                 200                 205

Asn Arg Pro Ile Val Asp Ile Asn Val Lys Asp Tyr Ser Ile Val Ser
    210                 215                 220

Ser Tyr Val Cys Ser Gly Leu Val Gly Asp Thr Pro Arg Lys Asn Asp
225                 230                 235                 240

Ser Ser Ser Ser Ser His Cys Leu Asn Pro Asn Asn Glu Glu Gly Gly
                245                 250                 255

His Gly Val Lys Gly Trp Ala Phe Asp Asp Gly Asn Asp Val Trp Met
            260                 265                 270

Gly Arg Thr Ile Ser Glu Lys Phe Arg Ser Gly Tyr Glu Thr Phe Lys
        275                 280                 285
```

Val Ile Glu Gly Trp Ser Lys Pro Asn Ser Lys Leu Gln Ile Asn Arg
    290                 295                 300

Gln Val Ile Val Asp Arg Gly Asn Arg Ser Gly Tyr Ser Gly Ile Phe
305                 310                 315                 320

Ser Val Glu Gly Lys Ser Cys Ile Asn Arg Cys Phe Tyr Val Glu Leu
                325                 330                 335

Ile Arg Gly Arg Lys Gln Glu Thr Glu Val Trp Trp Thr Ser Asn Ser
            340                 345                 350

Ile Val Val Phe Cys Gly Thr Ser Gly Thr Tyr Gly Thr Gly Ser Trp
        355                 360                 365

Pro Asp Gly Ala Asp Ile Asn Leu Met Pro Ile Met Ser Leu Leu Thr
    370                 375                 380

Glu Val Glu Thr Pro Ile Arg Asn Glu Trp Gly Cys Arg Cys Asn Asp
385                 390                 395                 400

Ser Ser Asp

<210> SEQ ID NO 47
<211> LENGTH: 86
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 47

Lys Ser Ser Trp Ser Asn His Asp Ala Ser Ser Gly Val Ser Ser Ala
1               5                   10                  15

Cys Pro Tyr Leu Gly Arg Ser Ser Phe Phe Arg Asn Val Val Trp Leu
            20                  25                  30

Ile Lys Lys Asn Ser Ala Tyr Pro Thr Ala Thr Arg Pro Lys Val Asn
        35                  40                  45

Gly Gln Ser Gly Arg Met Glu Phe Phe Trp Thr Ile Leu Lys Met Ser
    50                  55                  60

Leu Leu Thr Glu Val Glu Thr Pro Ile Arg Asn Glu Trp Gly Cys Arg
65                  70                  75                  80

Cys Asn Asp Ser Ser Asp
                85

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Glu Asn Asp Ala Gln Ala Pro Lys Ser
1               5                   10

<210> SEQ ID NO 49
<211> LENGTH: 98
<212> TYPE: PRT
<213> ORGANISM: Human papillomavirus

<400> SEQUENCE: 49

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
35 40 45

Arg Ala His Tyr Asn Ile Val Thr Phe Cys Cys Lys Cys Asp Ser Thr
50 55 60

Leu Arg Leu Cys Val Gln Ser Thr His Val Asp Ile Arg Thr Leu Glu
65 70 75 80

Asp Leu Leu Met Gly Thr Leu Gly Ile Val Cys Pro Ile Cys Ser Gln
85 90 95

Lys Pro

<210> SEQ ID NO 50
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
ccgctcgaga acgacgcaca agcaccaaaa tcaaaggtcg aagaggaagt aaac 54

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
ccctctagaa tcagagtttc actaagccaa 30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
atttgcggcc gctgtaatca tgcatggaga 30

<210> SEQ ID NO 53
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
ccctcgagtt atggtttctg agaacagat 29

<210> SEQ ID NO 54
<211> LENGTH: 26
<212> TYPE: PRT
<213> ORGANISM: Homo sapiens

<400> SEQUENCE: 54

Met Ala Thr Gly Ser Arg Thr Ser Leu Leu Leu Ala Phe Gly Leu Leu
1 5 10 15

Cys Leu Pro Trp Leu Gln Glu Gly Ser Ala 20 25

<210> SEQ ID NO 55
<211> LENGTH: 91
<212> TYPE: DNA
<213> ORGANISM: Homo sapiens

<400> SEQUENCE: 55
gatctccacc atggctacag gctcccggac gtccctgctc ctggcttttg gcctgctctg 60
cctgccctgg cttcaagagg gcagtgccgg c 91

<210> SEQ ID NO 56
<211> LENGTH: 91
<212> TYPE: DNA
<213> ORGANISM: Homo sapiens

<400> SEQUENCE: 56
aggtggtacc gatgtccgag ggcctgcagg gacgaggacc gaaaaccgga cgagacggac 60
gggaccgaag ttctcccgtc acggccgccg g 91

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
acgatggaga cagacacact cctgctatgg gtactgctg 39

<210> SEQ ID NO 58
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
tcctgctatg ggtactgctg ctctgggttc caggttc 37

<210> SEQ ID NO 59
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
tgctctgggt tccaggttcc actggtgaca tgcatg 36

<210> SEQ ID NO 60
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
tgggttccag gttccactgg tgacatgcat ggagatacac ctac 44

```
<210> SEQ ID NO 61
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61

ccgctcgagt ggtttctgag aacagatggg gcac                                34


<210> SEQ ID NO 62
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62

ccgctcgaga acgacgcaca agcaccaaaa agcaaggtcg aagaggaagt aaaccttc      58


<210> SEQ ID NO 63
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63

cgcgccgcgc gctagtctag agagtttgag taagccaaaa gatgag                   46


<210> SEQ ID NO 64
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64

gagacctcga gcagtcagca tgatagaaac atacagccaa ccttccc                  47


<210> SEQ ID NO 65
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65

cgcgccgcgc gcccctctag atcagagttt gagtaagcca aaagatgag                49


<210> SEQ ID NO 66
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66

ccgctcgaga acgacgcaca agcaccaaaa tcagtgtatc ttcatagaag gttggac       57


<210> SEQ ID NO 67
```

<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 67
ccctctagat cagagtttga gtaagccaaa ggac 34

<210> SEQ ID NO 68
<211> LENGTH: 9
<212> TYPE: PRT
<213> ORGANISM: Human papillomavirus

<400> SEQUENCE: 68

Arg Ala His Tyr Asn Ile Val Thr Phe
1 5

<210> SEQ ID NO 69
<211> LENGTH: 186
<212> TYPE: DNA
<213> ORGANISM: Artificial Sequence
<220> FEATURE:
<223> OTHER INFORMATION: Description of Artificial Sequence: Synthetic
construct

<400> SEQUENCE: 69
aaaagttctt ggtccaatca tgatgcctca tcaggggtga gctcagcatg tccatacctt 60
gggaggtcct cctttttcag aaatgtggta tggcttatca aaaagaacag tgcataccca 120
acagctacta gacccaaagt aaacgggcaa agtggaagaa tggagttctt ctggacaatt 180
ttaaag 186

<210> SEQ ID NO 70
<211> LENGTH: 113
<212> TYPE: DNA
<213> ORGANISM: Artificial Sequence
<220> FEATURE:
<223> OTHER INFORMATION: Description of Artificial Sequence: Synthetic
primer

<400> SEQUENCE: 70
aaaagttctt ggtccaatca tgatgcctca tcaggggtga gctcagcatg tccatacctt 60
gggaggtcct cctttttcag aaatgtggta tggcttatca aaaagaacag tgc 113

<210> SEQ ID NO 71
<211> LENGTH: 102
<212> TYPE: DNA
<213> ORGANISM: Artificial Sequence
<220> FEATURE:
<223> OTHER INFORMATION: Description of Artificial Sequence: Synthetic
primer

<400> SEQUENCE: 71
ctttaaaatt gtccagaaga actccattct tccactttgc ccgtttactt tgggtctagt 60
agctgttggg tatgcactgt tctttttgat aagccatacc ac 102

<210> SEQ ID NO 72
<211> LENGTH: 41
<212> TYPE: DNA
<213> ORGANISM: Artificial Sequence
<220> FEATURE:
<223> OTHER INFORMATION: Description of Artificial Sequence: Synthetic
primer

<400> SEQUENCE: 72
ccaccatgga gacagacaca ctcctgctat gggtactgct g 41

<210> SEQ ID NO 73
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
tcctgctatg ggtactgctg ctctgggttc caggttc 37

<210> SEQ ID NO 74
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
tgctctgggt tccaggttcc actggtgaca tgcatg 36

<210> SEQ ID NO 75
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
tgggttccag gttccactgg tgacatgaaa agttcttggt ccaatcatga tgc 53

<210> SEQ ID NO 76
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
ccgctcgagg ctttaaaatt gtccagaaga actcc 35

<210> SEQ ID NO 77
<211> LENGTH: 24
<212> TYPE: PRT
<213> ORGANISM: Influenza A virus

<400> SEQUENCE: 77

Met Ser Leu Leu Thr Glu Val Asp Thr Leu Thr Arg Asn Gly Trp Gly
1 5 10 15

Ser Arg Ser Ser Asp Ser Ser Asp
20

<210> SEQ ID NO 78
<211> LENGTH: 72
<212> TYPE: DNA
<213> ORGANISM: Influenza A virus

<400> SEQUENCE: 78

-continued

```
atgagccttc taaccgaggt tgacacgctt accagaaacg gatgggggtc cagatccagc     60

gattcaagtg at                                                          72


<210> SEQ ID NO 79
<211> LENGTH: 72
<212> TYPE: DNA
<213> ORGANISM: Influenza A virus

<400> SEQUENCE: 79

atcacttgaa tcgctggatc tggaccccca tccgtttctg gtaagcgtgt caacctcggt     60

tagaaggctc at                                                          72


<210> SEQ ID NO 80
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80

acgatggaga cagacacact cctgctatgg gtactgctg                             39


<210> SEQ ID NO 81
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81

tcctgctatg ggtactgctg ctctgggttc caggttc                               37


<210> SEQ ID NO 82
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82

tgctctgggt tccaggttcc actggtgaca tg                                    32


<210> SEQ ID NO 83
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83

tgggttccag gttccactgg tgacatgatg agccttctaa ccgaggttga c               51


<210> SEQ ID NO 84
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
```

ccgctcgaga tcacttgaat cgctgcatct gcacc 35

<210> SEQ ID NO 85
<211> LENGTH: 88
<212> TYPE: PRT
<213> ORGANISM: Artificial Sequence
<220> FEATURE:
<223> OTHER INFORMATION: Description of Artificial Sequence: Synthetic construct

<400> SEQUENCE: 85

Lys Ser Ser Trp Ser Asn His Asp Ala Ser Ser Gly Val Ser Ser Ala
1 5 10 15

Cys Pro Tyr Leu Gly Arg Ser Ser Phe Phe Arg Asn Val Val Trp Leu
20 25 30

Ile Lys Lys Asn Ser Ala Tyr Pro Thr Ala Thr Arg Pro Lys Val Asn
35 40 45

Gly Gln Ser Gly Arg Met Glu Phe Phe Trp Thr Ile Leu Lys Asp Ile
50 55 60

Met Ser Leu Leu Thr Glu Val Asp Thr Leu Thr Arg Asn Gly Trp Gly
65 70 75 80

Cys Arg Cys Ser Asp Ser Ser Asp
85

<210> SEQ ID NO 86
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
aaccatcact cttctggtga gctcaaagat atcaacgacg cacaagc 47

<210> SEQ ID NO 87
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
gctcaaagat atcaacgacg cacaagcacc aaaatcaaag gtc 43

<210> SEQ ID NO 88
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
atctcgagcg gaattccaga gtttgagtaa gccaaaagat gagaagcc 48

<210> SEQ ID NO 89
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
aaccatcact cttctggtag atctaaaagt tcttggtcca atc 43

<210> SEQ ID NO 90
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
aaactcgagt ctgatatcct ttaaaattgt ccagaagaac tc 42

<210> SEQ ID NO 91
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
aaccatcact cttctggtag atctatgagc cttctaaccg aggttgac 48

<210> SEQ ID NO 92
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
aaactcgagt ctgatatcat cacttgaatc gctggatctg g 41

<210> SEQ ID NO 93
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Glu Ile Asp Gly Pro Ala Gly Gln Ala Glu Pro Asp Arg Ala His Tyr
1 5 10 15

Asn Ile Val Thr Phe Cys Cys Lys Cys Asp
20 25

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Gly Gly Gly Gly Ser Gly Gly Gly Gly Ser Gly Gly Gly Gly Ser
1 5 10 15